(12) United States Patent
Uesugi et al.

(10) Patent No.: US 11,339,142 B2
(45) Date of Patent: May 24, 2022

(54) DI-SUBSTITUTED PYRAZOLE COMPOUNDS FOR THE TREATMENT OF DISEASES

(71) Applicant: FGH BIOTECH, INC., Houston, TX (US)

(72) Inventors: Motonari Uesugi, Osaka (JP); John Kincaid, Hayward, CA (US); Joel Huff, Spring Branch, TX (US)

(73) Assignee: FGH BIOTECH, INC., Houston, TX (US)

( * ) Notice: Subject to any disclaimer, the term of this patent is extended or adjusted under 35 U.S.C. 154(b) by 0 days.

(21) Appl. No.: 16/331,505

(22) PCT Filed: Sep. 7, 2017

(86) PCT No.: PCT/US2017/050562
§ 371 (c)(1),
(2) Date: Mar. 7, 2019

(87) PCT Pub. No.: WO2018/049080
PCT Pub. Date: Mar. 15, 2018

(65) Prior Publication Data
US 2019/0194167 A1    Jun. 27, 2019

Related U.S. Application Data

(60) Provisional application No. 62/438,944, filed on Dec. 23, 2016, provisional application No. 62/384,661, filed on Sep. 7, 2016.

(51) Int. Cl.
| | | |
|---|---|---|
| *C07D 401/14* | (2006.01) | |
| *C07D 405/14* | (2006.01) | |
| *C07D 401/04* | (2006.01) | |
| *A61P 9/10* | (2006.01) | |
| *A61P 3/04* | (2006.01) | |
| *A61P 3/10* | (2006.01) | |
| *A61P 9/12* | (2006.01) | |
| *A61P 35/00* | (2006.01) | |

(52) U.S. Cl.
CPC .............. *C07D 401/14* (2013.01); *A61P 3/04* (2018.01); *A61P 3/10* (2018.01); *A61P 9/10* (2018.01); *A61P 9/12* (2018.01); *A61P 35/00* (2018.01); *C07D 401/04* (2013.01); *C07D 405/14* (2013.01)

(58) Field of Classification Search
CPC .. C07D 401/14; C07D 401/04; C07D 405/14; A61P 9/10; A61P 3/04; A61P 3/10; A61P 9/12; A61P 35/00
USPC ...................................................... 546/275
See application file for complete search history.

(56) References Cited

U.S. PATENT DOCUMENTS

| | | |
|---|---|---|
| 5,466,823 A | 11/1995 | Talley et al. |
| 5,712,303 A | 1/1998 | Faraci et al. |
| 5,939,462 A | 8/1999 | Connell et al. |
| 6,130,217 A | 10/2000 | Arnold et al. |
| 6,248,363 B1 | 6/2001 | Patel et al. |
| 8,207,196 B2 | 6/2012 | Uesugi et al. |
| 8,778,976 B2 | 7/2014 | Uesugi et al. |
| 8,927,578 B2 | 1/2015 | Uesugi et al. |
| 9,085,566 B2 | 7/2015 | Uesugi et al. |
| 9,187,485 B2 | 11/2015 | Uesugi et al. |
| 9,212,179 B2 | 12/2015 | Uesugi et al. |
| 9,233,941 B2 | 1/2016 | Uesugi et al. |
| 9,713,613 B2 | 7/2017 | Uesugi et al. |
| 9,873,689 B2 | 1/2018 | Cantrell, Jr. |
| 2002/0065289 A1 | 5/2002 | Kordik et al. |
| 2002/0111353 A1 | 8/2002 | Ledeboer et al. |
| 2003/0055085 A1 | 3/2003 | Wagenen et al. |
| 2004/0229927 A1 | 11/2004 | Sircar et al. |
| 2008/0108799 A1 | 5/2008 | Weiss |
| 2008/0280869 A1 | 11/2008 | Almstead et al. |
| 2009/0054491 A1 | 2/2009 | Edwards et al. |
| 2011/0021771 A1 | 1/2011 | Mallais et al. |

(Continued)

FOREIGN PATENT DOCUMENTS

| | | |
|---|---|---|
| AU | 2004200420 A1 | 9/2004 |
| CN | 105294584 A | 2/2016 |

(Continued)

OTHER PUBLICATIONS

The role of Proprotein Convertase Subtilisin/Kexin Type 9(PCSK9) in Cardiovascular Homeostasis; A non-systematic Literature Reiew. by Ahmad Hachem et al. (Year: 2017).*
Gowhar Ali, Input of Isosteric and Bioisosteric Approach in Drug design. (Year: 2013).*
Hitoshi Shimano , SREBPs: pysiology and pathophysiology of the SREBP family. (Year: 2008).*

(Continued)

*Primary Examiner* — Daniel R Carcanague
(74) *Attorney, Agent, or Firm* — Squire Patton Boggs (US) LLP

(57) ABSTRACT

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and nonalcoholic fatty liver disease (NAFLD) wherein the compound is according to Formula (I).

(I)

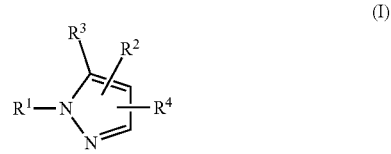

19 Claims, 2 Drawing Sheets

(56) References Cited

U.S. PATENT DOCUMENTS

| | | |
|---|---|---|
| 2011/0046147 A1 | 2/2011 | Hartmann et al. |
| 2011/0112282 A1 | 5/2011 | Roehrig et al. |
| 2012/0252796 A1 | 10/2012 | Pingali et al. |
| 2013/0018053 A1 | 1/2013 | Zhou et al. |
| 2014/0038984 A1 | 2/2014 | Uesugi et al. |
| 2014/0045845 A1 | 2/2014 | Uesugi et al. |
| 2014/0235646 A1 | 8/2014 | Uesugi et al. |
| 2014/0329684 A1 | 11/2014 | Muller et al. |
| 2015/0065519 A1 | 3/2015 | Chakravarty et al. |
| 2015/0210705 A1 | 7/2015 | Jacobsen et al. |
| 2015/0307501 A1 | 10/2015 | Uesugi et al. |
| 2016/0128985 A1 | 5/2016 | Uesugi et al. |
| 2018/0000801 A1 | 1/2018 | Uesugi et al. |
| 2018/0028518 A1 | 2/2018 | Bernales et al. |
| 2018/0051013 A1 | 2/2018 | Pujala et al. |
| 2018/0291013 A1 | 10/2018 | Uesugi et al. |
| 2019/0071434 A1 | 3/2019 | Boxer et al. |
| 2019/0134017 A1 | 5/2019 | Huff et al. |
| 2019/0194167 A1 | 6/2019 | Uesugi et al. |

FOREIGN PATENT DOCUMENTS

| | | | |
|---|---|---|---|
| DE | 3406329 | | 8/1985 |
| EP | 1698626 A1 | | 9/2006 |
| IN | 2816/MUM/2013 | | 5/2016 |
| JP | S61-010557 A | | 1/1986 |
| JP | 1996181009 | | 1/1998 |
| JP | 2006-514095 A | | 4/2006 |
| JP | 2008-528700 A | | 7/2008 |
| WO | WO 2003/087061 A1 | | 10/2003 |
| WO | WO 2003/097335 A1 | | 11/2003 |
| WO | WO 2004/050632 A1 | | 6/2004 |
| WO | WO 2005/044194 A2 | | 5/2005 |
| WO | WO 2005/063737 A1 | | 7/2005 |
| WO | WO 2006/084176 A2 | | 8/2006 |
| WO | WO 2007/052843 | | 5/2007 |
| WO | WO 2008/090382 | | 7/2008 |
| WO | WO 2008/097835 A2 | | 8/2008 |
| WO | WO 2009/083581 A1 | | 7/2009 |
| WO | WO 2011/051961 A1 | | 5/2011 |
| WO | WO-2011109261 A1 * | 9/2011 | ........... C07D 213/69 |
| WO | WO 2013/039988 A1 | | 3/2013 |
| WO | WO 2015/031710 A1 | | 3/2015 |
| WO | WO 2015/067646 A1 | | 5/2015 |
| WO | WO 2016/105331 A1 | | 7/2015 |

OTHER PUBLICATIONS

Gong Zhihong et al , Obesity , Diabetes, and Risk of Prostate Cancer: Results from the Prostrate Cancer Prevention Trial (Year: 2006).*

Input of Isosteric and Bioisosteric Approach in Drug Design , Gowhar Ali et al. (Year: 2013).*

De Barros et al. Anais da Associacao Brasileira de Quimica (2001), 50(4), 162-165.

Bellale, Eknath et al., "Diarylthiazole: an antimycobacterial scaffold potentially targeting PrrB-PrrA two-component system", Journal of Medicinal Chemistry Jun. 26, 2014, vol. 57, No. 15, pp. 6572-6582.

Chen, Y et al., "Copper catalyzed synthesis of 1-aryl-1,2,3-triazoles from aryl iodides, alkynes, and sodium azide," Journal of Organometallic Chemistry 2014, 749(31):215-218.

Compounds comprising pyrazole, STN database accessed on Jan. 18, 2019, 237 pages.

International Search Report and Written Opinion dated Nov. 15, 2017 in International Patent Application No. PCT/US2017/050562, 11 pages.

Krishnan et al., "Synthesis of Aryltriazolyl Derivatives," Indian Journal of Chemistry, vol. 26B, Jul. 1987, pp. 616-619.

Ueda, S. et al. Angew. Chem. Int. Ed. 2011, 38, 8944.

Vachal et al., "Highly selective and potent agonists of sphingosine-l-phosphate 1 ($S1P_1$) receptor," Bioorganic & Medicinal Chemistry Letters, 16:3684-3687, 2006.

Xu et al., "Design, synthesis, and biologic evaluation of some novel N-arylpyrazole derivatives as cytotoxic agents," Medicinal Chemistry Research 2013, vol. 22, 5610-5616.

Zhang et al., "Design, synthesis, and biological evaluation of 5-(4-(pyridin-4-yl)-1H-1,2,3-triazol-1-yl)benzonitrile derivatives as xanthine oxidase inhibitors," Chemical Biology & Drug Design 2018, 91(2), 526-533.

Cheng et al. "Glucose-Mediated N-Glycosylation of SCAP is Essential for SREBP-1 Activation and Tumor Growth," CellPress 2015, 28(5), 569-581.

Du et al. FGFR3 Stimultes Stearoyl CoA Desaturase 1 Activity to Promote Bladder Tumor Growth, Cancer Res Actions 2012, 72(22), 5843-55.

Gabitova et al. "Molecular Pathways: Sterols and Receptor Signaling in Cancer," Clin Cancer Res. 2014, 20(1), 28-34.

Horton et al. "Molecular Biology of PCSK9: Its Role in LDL Metabolism," Trends Biochem Sci. 2007, 32(2), 71-77.

Kamisuki et al. "A Small Molecule that Blocks Fat Synthesis by Inhibiting the Activation of SREBP," Chemistry and Biology 2009, 16, 882-892.

Li et al. "Fatostatin Displays High Antitumor Activity in Prostate Cancer by Blocking SREBP-Regulated Metabolic Pathways and Androgen Receptor Signaling" Mol Cancer Ther. 2014, 13(4), 855.

Li et al. "Anti-cancer efficacy of SREBP inhibitor, alone or in combination with docetaxel, in prostate cancer harboring p53 mutations," Oncotarget. 2015, 6(38), 41018.

Mason et al. "SCD1 Inhibition Causes Cancer Cell Death Depleting Mono-Unsaturated Fatty Acids," PLoS ONE 2012, 7(3), e33823, doi:10.1371/journal.pone.0033823.

Parrales et al. "Unsaturated fatty acids regulate sternness of ovarian cancer cells through NF-κB," Stem Cell Investig. 2017, 4, 49.

Peck et al. "Inhibition of Fatty Acid Desaturation is Detrimental to Cancer Cell Survival in Metabolically Compromised Environments," Cancer and Mtabolism 2016, 4:6, 1-18.

Roongta et al. "Cancer Cell Dependency on Unsaturated Fatty Acids Implicates Stearoyl-CoA Desaturase as a Target for Cancer Therapy," Molecular Cancer Research 2011, 9(11), 1551-61.

Southam et al. "Drug Redeployment to Kill Leukemia and Lymphoma Cells by Disrupting SCD1-mediated Synthesis of Monounsaturated Fatty Acids," Cancer Research 2015, 75(2), 2530-2540.

Sunami et al. "Lipid Metabolism and Lipid Droplets in Pancreatic Cancer and Stellate Cells" Cancers 2018, 10 (3), doi:10.3390/cancers10010003.

Brown et al., "Stearoyl-coenzyme A desaturase 1 inhibition and the metabolic syndrome: considerations for future drug discovery," Current Opinion in Lipidology 2010, 21:192-197; DOI:10.1097/MOL.0b013e32833854ac.

Guo et al. "Targeting SREBP-1-driven lipid metabolism to treat cancer," Curr Pharm Des. 2014, 20(15), 2619-2626.

MacDonald et al. , "Absence ofstearoyl-CoA desaturase-1 ameliorates features of the metabolic syndrome in LDLR-deficient mice", J. Lipid Res. 2008. 49: 217-229. DOI 10.1194/jlr.M700478-JLR200.

Li et al., "Anti-cancer efficacy of SREBP inhibitor, alone or in combination with docetaxel, in prostate cancer harboring p53 mutations", www.impactjournals.com/oncotarget, Oncotarget, vol. 6, No. 38 pp. 41018-41033, published Oct. 16, 2015.

Kumari et al., "$Sc(OTf)_3$-catalyzed, solvent-free domino synthesis of functionalized pyrazoles under controlled microwave irradiation", Tetrahedron Letters, 53:1130-1133 (2012).

Gong et al., "Obesity, Diabetes, and Risk of Prostate Cancer: Results from the Prostate Cancer Prevention Trial", Cancer Epidemiology Biomarkers and Prevention, 15(10): 1977-1983 (2006).

Grosche et al., "Pyrazole, Pyridine, and Pyridone Syntehsis on Solid Support", Synthesis, 11:1961-1970 (1999).

El-Khawass et al., "The Difference in the Behaviour of Hydrazine and p-Substituted Phenylhydrazines on Various 4-(3-Aryl-3-Oxopropenyl) Antipyrines", Journal of the Chinese Chemical Society, 1990, 37, 605-609 (1990).

Shimano et al., SREBPs: physiology and pathophysiology of the SREBP Family, FEBS Journal 2009, 276:616-621 (2006).

(56) References Cited

OTHER PUBLICATIONS

Suri et al., "An Efficient Copper-Catalyzed Formation of Highly Substituted Pyrazoles Using Molecular Oxygen as the Oxidant", Green Chemistry, 14:2193-2196, supporting information pp. S1-S87 (2012).

Abifadel et al., "Mutations in PCSK9 cause autosomalet dominant hypercholesterolemia", Nat Genet. Jun. 2003; 34(2):154-6 (abstract only).

Cohen et al. "Low LDL Cholesterol in individuals of African descent resulting from frequest nonsense mutations in PCSK9", Nat Genet. Feb. 2005; 37(2):161-5 (abstract only).

Urban et al., Targeting the proprotein convertase subtilisin/ Kexin TYPE 9 for the Treatment of Dyslipidemia and Atherosclerosis, *J. Am. Coll. Cardiol*. Oct. 15, 2013; 62(16):1401-8.

\* cited by examiner

Compound A down regulated PCSK9 resulting in upregulation of LDLR HepG2 cells treated for 24 hours

DI-SUBSTITUTED PYRAZOLE COMPOUNDS FOR THE TREATMENT OF DISEASES

CROSS-REFERENCE TO RELATED APPLICATIONS

This application is a § 371 of International Application No. PCT/US2017/050562 filed Sep. 7, 2017, and which claims priority benefit of U.S. Provisional Patent Application No. 62/384,661 filed Sep. 7, 2016, and claims priority benefit of U.S. Provisional Patent Application No. 62/438,944 filed Dec. 23, 2016, the contents of each of which are incorporated herein by reference in their entirety for all purposes.

FIELD

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and nonalcoholic fatty liver disease (NAFLD).

BACKGROUND

Animals, including humans rely on fat and carbohydrate as their major energy sources required to sustain their activity needs. Long chain fatty acids are major sources of energy and important components of the lipids that comprise the cellular membranes. They are derived from food and synthesized de novo from acetyl-CoA. Hence, acetyl-CoA is an intermediate that interrelates glucose and fatty acid metabolism.

Cholesterol is also derived from food and synthesized from acetyl-CoA. The conversion of carbohydrates into acyl glycerides through de novo fatty acid and cholesterol synthesis involves at least 12 and 23 enzymatic reactions, respectively. Expression levels of the genes encoding these enzymes are controlled by three transcription factors, designated sterol regulatory element-binding proteins (SREBPs): SREBP-1a, -1c and SREBP-2. SREBPs are membrane-bound proteins and are members of a class of the basic helix-loop-helix leucin zipper family of transcription factors. Unlike other leucin zipper members of transcription factors, SREBPs are synthesized as Endoplasmic-reticulum (ER)-membrane-bound precursors, which need to be proteolytically released by two proteases bound to the Golgi membrane, Site-1 and Site-2 proteases, to generate active forms, nSREBPs, that activate transcription of target genes in the nucleus (DeBose-Boyd et al. Cell 1999, 99 (7), 703; Sakai et al. Cell 1996, 85, 1037). The proteolytic activation of SREBPs is tightly regulated by sterols that are known to induce the interaction of the SREBP cleavage-activating protein (SCAP) with the ER membrane-bound insulin-induced gene (INSIG), thereby inhibiting the exit of the SREBP/SCAP complex from the ER (Yabe et al. *Proc Natl Acad Sci USA* 2002, 99(20), 12753; Yang et al., *Cell* 2002, 110, 489-500). When sterols accumulate in the ER membranes, the SCAP/SREBP complex fails to exit the ER to the Golgi apparatus, and the proteolytic processing of SREBPs is suppressed. Thus, SREBPs are key lipogenic transcription factors that govern the homeostasis of fat metabolism. Interestingly, both SREBP isoforms have some overlap in target genes, yet they have distinct roles in lipid metabolism (Eberle et al. *Biochimie* 2004, 86 (11), 839).

Numerous studies have shown that SREBPs integrate several cell signals to regulate lipogenesis and other pathways important for diseases such as type II diabetes, dyslipidemia, cancer and the immune response (Shao W. and Espenshade P J., *Cell Metab.* 2012, 16, 414). In addition, studies in animal models and humans suggested a strong correlation between upregulation of SREBPs and SREBP-1c in particular and the pathogenesis of these diseases and reducing the activity of SREBPs may be beneficial to treat these diseases and ameliorate their complications (Zhao et al., *Diabetes* 2014, (63) 2464). In addition to life style treatment, individual drugs have been developed to treat these diseases that associated with the metabolic syndrome. The central role of SREBPs in the regulation of lipids and their potential role as a major player in several diseases raised the possibility of novel approaches to treat several risk factors with one drug (Soyal et al. *Trends Pharmacol Sciences* 2015, (36) 406).

Metabolic syndrome comprises many cardiovascular risk factors that, occurring together, increase a person's risk of diseases like heart disease, stroke, and type 2 diabetes. These risk factors include hypertension, dyslipidaemia, obesity, high blood sugar, pancreatic β-cell dysfunction, and atherosclerosis. Disturbing the balance between energy expenditure and food intake, in addition to predisposing genetic factors, can result in pathological conditions, diseases, or disorders such as obesity, diabetes and cardiovascular disease. Targeting metabolic pathways, especially those that are related to lipid and fat metabolism, has been used to develop drugs against these diseases (Padwal et al. *Lancet* 2007, 369(9555), 71). Although pharmacological intervention against individual abnormalities associated with metabolic syndrome is possible, it would be of great advantage to target multiple metabolic pathways by lowering lipids (triglycerides and cholesterol), in addition to controlling blood glucose in diabetic patients.

One of the major consequences of metabolic syndrome and obesity in particular is the development of nonalcoholic fatty liver disease (NAFLD). NAFLD is a condition that is caused by excess of fat accumulation in the liver of patients without a history of alcohol abuse. NAFLD is the liver manifestation of metabolic syndrome and has been increasing worldwide in line with the epidemic increase in obesity, type 2 diabetes and dyslipidemia (Takahashi Y, Fukusato T. Histopathology of nonalcoholic fatty liver disease/nonalcoholic steatohepatitis. *World J Gastroenterol.* 2014 Nov. 14; 20(42):15539-48). NAFLD can be a simple steatosis (triglyceride accumulation in liver) due to shift in de novo fatty acid metabolism to net lipogenesis from lipolysis, or the more serious nonalcoholic steatohepatitis (NASH). NASH is considered the major chronic liver disease, with serious damage to liver such as interlobular inflammation, hepatocellular ballooning and fibrosis and it may lead to liver cirrhosis and hepatocellular carcinoma (Schreuder et al. *World J Gastroenterol* 2008, 14(16), 2474). It is estimated that 15% of the adult population in the US have NAFLD and about 3-4% suffer from NASH (Ekstedt et al. *Hepatology* 2006, 44(4), 865). Currently treatment for NASH is limited to substantial weight loss by methods such as bariatric surgery, insulin sensitizing agents and Vitamin E supplements, in addition to life style modification by diet and exercise.

Another risk factor associated with metabolic syndrome is the development of diabetes mellitus where dyslipidemia, including high levels of LDL cholesterol, is very common in these patients. These patients are at very high risk of developing atherosclerotic cardiovascular disease. Numerous studies including genetic studies support the notion that high levels of LDL are implicated in coronary artery disease and that lowering LDL cholesterol reduces the risk of cardiovascular events (Ajufo et al. *Lancet Diabetes Endocrinol.* 2016 May; 4(5):436-46). At the genetic level, familial hypercholesterolemia, a mendelian disorder caused by mutations in LDL Receptor (LDLR) and other genes in LDL-Receptor pathways is associated with high levels of LDL and increased risk of cardiovascular disease (Kolansky et al. *Am J Cardiol.* 2008 Dec. 1; 102(11):1438-43. One of the known genes that was linked to familial hypercholesterolemia is the proprotein convertase subtilisn/hexin 9 (PCSK 9) which is secreted by hepatocytes (Urban et al. *J Am Coll Cardiol.* 2013 Oct. 15; 62(16):1401-8). It was shown that gain of function in PCSK 9 caused high level of LDL and increased cardiovascular events (Abifadel M et al. *Nat Genet.* 2003 June; 34(2):154-6). On the other hand patients with mutations in this gene had very low level of LDL suggesting that PCSK9 is potential therapeutic target for reducing LDL cholesterol (Cohen et al. *Nat Genet.* 2005 February; 37(2):161-5).

In addition, increasing evidence show a strong link between metabolic syndrome and variety of cancers including, breast, liver, and prostate (Gabitova et al. *Clin Cancer Res.* 2014, 20(1), 28). Major hallmarks of tumor cells are over expression and increased metabolic activities such as glucose consumption, protein and nucleic acid synthesis and increased de novo fatty acid synthesis (Menendez, J. A., and Lupu, R. *Nat Rev Cancer* 2007, 7, 763). It has been shown that, contrary to normal cells, various tumor cells are very active in de novo fatty acid biosynthesis, irrespective of the extracellular lipids, and that de novo fatty acids accounted for all fatty acid esterification in the tumor cells (Medes et al. *Cancer Research* 1953, 13, 27.) Pharmacological and RNAi knockdown approaches against ACC and FAS have been reported (Brusselmans et al. *Cancer Research* 2005, 65, 6719-6725; Kuhajda et al. *Proceedings of the National Academy of Sciences of the United States of America* 2000, 97, 3450-3454; Menendez, et al. *Int J Cancer* 2005, 115, 19-35). These studies showed that inhibiting these enzymes induced growth inhibition and apoptotic effect against breast and prostate cancer cells. In this regard, SREBP-1 and 2 as master regulators of lipid biosynthesis play a major role in tumor growth. In support of the role of SREBP in cancer, several studies have shown that inhibition of SREBP activation using RNAi and a small molecule resulted in significant growth inhibition. On the other hand it was recently reported that glucose-mediated N-glycolsylation of SCAP resulted in its stabilization and activation of SREBP-1 to promote tumor growth in glioblastoma (Cheng et al. 2015). These findings suggest that targeting the SCAP/SREBP complex is a promising approach for treating cancer and metabolic diseases.

Several studies have provided proof of concept for the efficacy of small molecules targeting transcriptional SREBPs activity to treat several components of metabolic syndrome. Betulin, a pentacyclic triterpene that occurs in birch bark, decreased the level of the mature active forms of both SREBP-1 and 2 in human liver Huh-7 cell line, resulting in down regulation of genes involved in cholesterol and fatty acid synthesis (Tang et al., *Cell Metabol* 2011 (13) 44). These authors presented evidence showing that betulin directly interacts with SCAP. Mice that were fed western diet, which induces obesity, fatty liver and dyslipidemia, and treated with betulin had lower weight gain, accumulated less fat without affecting food intake (Tang et al., *Cell Metabol* 2011 (13) 44). In addition, the treated mice had lower triglycerides, cholesterol plasma glucose and improved insulin sensitivity. These metabolic improvements were reflected in reduced levels of hepatic SREBP and its target genes.

Fatostatin is a diarylthiazole small molecule and is the first non-cholesterol molecule that acts on the translocation of SREBPs from the ER to the Golgi, hence affecting the downregulation of the major players in lipid metabolism, including triglyceride (TG) and cholesterol (Kamisuki et al. *Chem Biol.* 2009, 16, 882-92; Kamisuki et al. *J Med Chem.* 2011 54, 4923). Fatostatin derivatives such as FGH10019 bind specifically to the SREBP-cleavage activating protein (SCAP) at a distinct site from the sterol-binding domain. As a result of FGH10019 action, SREBPs are retained in the ER, blocking their transportation to the Golgi apparatus, where they are processed by proteases to produce the nuclear active form bHLH. Recently several studies showed that fatostatin derivatives inhibited cell growth in cells and animal models for breast and prostate thus validating the potential use of these compounds to treat cancer (Li et al. *Mol Cancer Ther.* 2014, 13(4), 855; Li et al. *Oncotarget.* 2015, 6(38). 41018). However, while fatostatin or FGH10019 could provide a starting point for providing small molecules for new pharmacological interventions to combat metabolic diseases, it has liabilities which may preclude its use as a drug. Thus, small molecules with improved drug-like qualities are needed.

SUMMARY OF THE INVENTION

Provided herein are compounds, pharmaceutical compositions comprising the compounds, and methods of using the compounds and compositions in treating a condition, disease, or disorder associated with abnormal activation of the SREBP pathway, including metabolic disorders such as obesity, cancer, cardiovascular disease, and nonalcoholic fatty liver disease (NAFLD).

In one aspect, provided is a Compound of Formula (I):

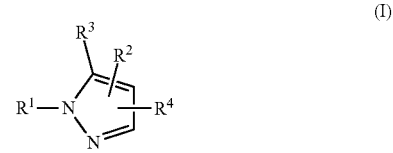

where
$R^1$ is pyridinonyl, where the pyridinonyl is substituted on its nitrogen with $R^{1b}$ and is additionally optionally substituted with 1 lea;
$R^{1a}$, when present, is halo, alkyl, alkenyl, haloalkyl, cycloalkyl, cycloalkylalkyl, heterocycloalkyl, or heterocycloalkylalkyl;
$R^{1b}$ is hydrogen, alkyl, alkenyl, haloalkyl, cycloalkyl, cycloalkylalkyl, heterocycloalkyl, or heterocycloalkylalkyl;
$R^2$ is

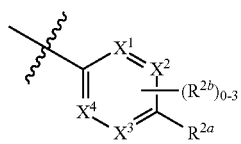

where 0, 1, or 2 of $X^1$-$X^4$ are nitrogen and the remaining are CH or $CR^{2b}$;

$R^{2a}$ is $-OR^5$, $-S(O)R^6$, or $-S(O)_2R^7$;

each $R^{2b}$, when present, is independently halo, alkyl, haloalkyl, $-NO_2$, or cyano;

$R^3$ is hydrogen, halo, alkyl, or haloalkyl;

$R^4$ is hydrogen, halo, alkyl, or haloalkyl; and $R^5$, $R^6$, and $R^7$ are independently alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl, and heterocycloalkyl, alone or as part of heterocycloalkylalkyl, are optionally substituted with 1, 2, or 3 groups independently selected from alkyl, hydroxy, halo, and hydroxyalkyl; or a stereoisomer, a mixture of stereoisomers, and/or a pharmaceutically acceptable salt thereof.

In another aspect, provided herein are pharmaceutical compositions, single unit dosage forms, and kits suitable for use in treating disorders associated with abnormal activation of the SREBP pathway which comprise a therapeutically effective amount of a compound provided herein, e.g., of some or any of the embodiments, of Formula (I)-(Ij), (Ia-1)-(Ij-1), and specific compounds, and a pharmaceutically acceptable carrier thereof.

In another aspect, provided herein is a method of treating a condition, disease, or disorder associated with abnormal activation of the SREBP pathway comprising a) administering a therapeutically effective amount of a compound provided herein, e.g., of some or any of the embodiments, of Formula (I)-(Ij), (Ia-1)-(Ij-1), and specific compounds or a stereoisomer, a mixture of stereoisomers, and/or a pharmaceutically acceptable salt thereof or b) administering a therapeutically effective amount of a composition comprising a compound provided herein, e.g., of some or any of the embodiments, of Formula (I)-(Ij), (Ia-1)-(Ij-1), and specific compounds or a stereoisomer, a mixture of stereoisomers, and/or a pharmaceutically acceptable salt thereof and a pharmaceutically acceptable carrier thereof.

In another aspect, provided herein is a method of preparing a Compound of Formula (I)-(Ij), (Ia-1)-(Ij-1), and specific compounds or a stereoisomer, a mixture of stereoisomers, and/or a pharmaceutically acceptable salt thereof comprising treating an intermediate of formula:

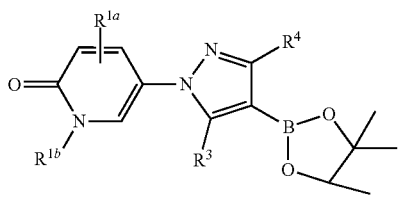

with an intermediate of formula:

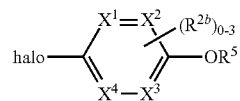

using coupling conditions described herein or known to one of ordinary skill in the art. In some or any embodiments, halo is bromo.

DESCRIPTION OF EXEMPLARY EMBODIMENTS

Definitions

Figure 1A:
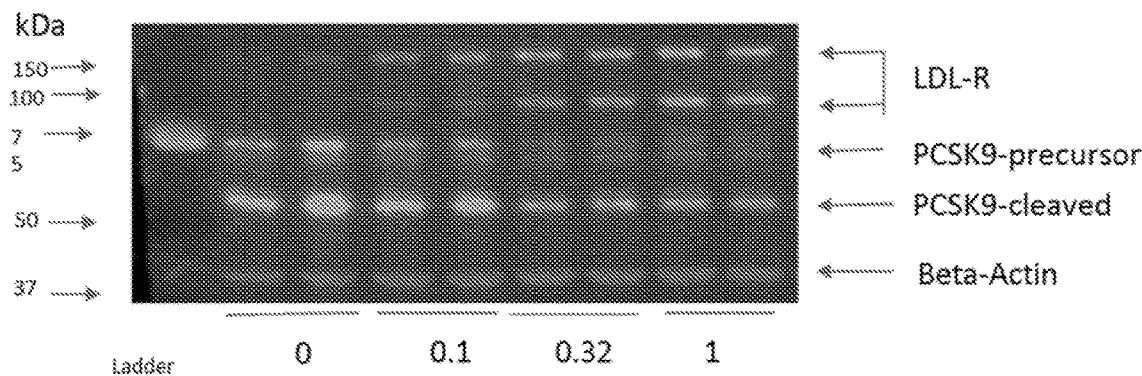
FIG. 1A shows a Western blot from liver extracts using control and Compound A-treated HepG2 cells after 24 h, where Compound A down-regulated PCSK9 in a dose-dependent manner, resulting in up-regulation of OW density lipoprotein receptor (LDLR) protein.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being unsubstituted or substituted, the groups in the list of substituents are themselves unsubstituted. For example, a substituted alkyl group can be substituted, for example, with a cycloalkyl group, and the cycloalkyl group is not further substituted unless specified otherwise.

"Acyl" means a $-C(O)R$ group where R is alkyl, as defined herein.

"Alkoxy" means an $-OR$ group where R is an alkyl group as defined herein.

"Alkenyl" means a straight or branched hydrocarbon radical having from 2 to 8 carbon atoms and at least one double bond and in some embodiments, includes ethenyl, propenyl, 1-but-3-enyl, 1-pent-3-enyl, 1-hex-5-enyl and the like. "Lower alkenyl" means an alkenyl group having one to six carbon atoms. Alkenyl is not substituted unless stated otherwise.

"Alkyl" means a linear or branched hydrocarbon group having one to eight carbon atoms. "Lower alkyl" means an alkyl group having one to six carbon atoms. In some embodiments, lower alkyl includes methyl, ethyl, propyl, isopropyl, butyl, s-butyl, t-butyl, isobutyl, pentyl, hexyl and the like. A "$C_0$" alkyl (as in "$C_0$-$C_6$-alkyl") is a covalent bond. "$C_6$ alkyl" refers to, for example, n-hexyl, iso-hexyl, and the like.

"Alkylsulfonyl" means a $-S(O)_2R$ group where R is an alkyl group as defined herein.

"Cycloalkyl" means a monocyclic or polycyclic hydrocarbon radical having three to thirteen carbon atoms. The cycloalkyl can be saturated or partially unsaturated, but cannot contain an aromatic ring. In some embodiments, cycloalkyl includes fused, bridged, and spiro ring systems. In some embodiments, cycloalkyl is cyclopropyl, cyclobutyl, cyclopentyl or cyclohexyl.

"Cycloalkylalkyl" means alkyl group substituted with one or two cycloalkyl group(s), as defined herein. In some embodiments, cycloalkylalkyl includes cyclopropylmethyl, 2-cyclobutyl-ethyl, and the like.

"Haloalkyl" means an alkyl group, as defined herein, substituted with one or more halogens, for example one, two, three, four, or five halo atoms. In some embodiments, haloalkyl includes 2,2-difluoroethyl, trifluoromethyl, and 2-chloro-1-fluoroethyl, and the like.

"Heterocycloalkyl" means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the point of attachment of the group may be located on any atom of any ring within the radical, valency rules permitting. In particular, when the point of attachment is located on a nitrogen atom, R$^y$ is absent. In some embodiments, the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and an N-oxide thereof.

"Heterocycloalkylalkyl" means an alkyl group, as defined herein, substituted with one or two heterocycloalkyl group(s), as defined herein.

"Hydroxyalkyl" means an alkyl group, as defined herein, substituted with at least one, in some embodiments one, two, or three, hydroxy group(s), provided that if two hydroxy groups are present they are not both on the same carbon atom. In some embodiments, hydroxyalkyl includes, but is not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, 2-hydroxyethyl, 2,3-dihydroxypropyl, or 1-(hydroxymethyl)-2-hydroxyethyl, and the like.

"Patient" or "subject" includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

The term "substantially free of" or "substantially in the absence of" stereoisomers with respect to a composition refers to a composition that includes at least 85 or 90% by weight, in certain embodiments 95%, 98%, 99% or 100% by weight, of a designated stereoisomer of a compound in the composition. In certain embodiments, in the methods and compounds provided herein, the compounds are substantially free of stereoisomers.

Similarly, the term "isolated" with respect to a composition refers to a composition that includes at least 85, 90%, 95%, 98%, 99% to 100% by weight, of a specified compound, the remainder comprising other chemical species or stereoisomers.

The term "solvate," as used herein, and unless otherwise specified, refers to a compound provided herein or a salt thereof, that further includes a stoichiometric or non-stoichiometric amount of solvent bound by non-covalent intermolecular forces. Where the solvent is water, the solvate is a hydrate.

The term "isotopic composition," as used herein, and unless otherwise specified, refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

The term "isotopic enrichment," as used herein, and unless otherwise specified, refers to the percentage of incorporation of an amount of a specific isotope at a given atom in a molecule in the place of that atom's natural isotopic abundance. In certain embodiments, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

The term "isotopically enriched," as used herein, and unless otherwise specified, refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," and "heterocycloalkyl" groups optionally comprise deuterium at one or more positions where hydrogen atoms are present, and wherein the deuterium composition of the atom or atoms is other than the natural isotopic composition.

Also as used herein, "alkyl," "cycloalkyl," and "heterocycloalkyl" groups optionally comprise carbon-13 at an amount other than the natural isotopic composition.

As used herein, and unless otherwise specified, the term "$IC_{50}$" refers to an amount, concentration or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and in certain embodiments, a human. In certain embodiments, the subject is a farm animal (e.g., a horse, a cow, a pig, etc.) or a pet (e.g., a dog or a cat). In certain embodiments, the subject is a human.

"Administration" and variants thereof (in some embodiments, "administering" a compound) in reference to a compound of the invention means introducing the compound or a prodrug of the compound into the system of the animal in need of treatment. When a compound of the invention or prodrug thereof is provided in combination with one or more other active agents (in some embodiments, surgery, radiation, and chemotherapy, etc.), "administration" and its variants are each understood to include concurrent and sequential introduction of the compound or prodrug thereof and other agents.

"Therapeutically effective amount" is an amount of a compound or composition, that when administered to a patient, is sufficient to effect such treatment for the condition, disease, or disorder, e.g. to ameliorate a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, e.g. relieving or reducing a symptom thereof, and/or causing regression of the disease, disorder, or syndrome. As is known in the art, adjustments for systemic versus localized delivery, age, body weight, general health, sex, diet, time of administration, drug interaction and the severity of the condition, disease, or disorder may be necessary, and will be ascertainable with routine experimentation by one of ordinary skill in the art. "Treating" or "treatment" of any condition, disease, or disorder refers, in certain embodiments, to ameliorating a condition, disease, or disorder that exists in a subject. In another embodiment, "treating" or "treatment" includes ameliorating at least one physical parameter, which may be indiscernible by the subject. In yet another embodiment, "treating" or "treatment" includes modulating the condition, disease, or disorder, either physically (e.g., stabilization of a discernible symptom) or physiologically (e.g., stabilization of a physical parameter) or both. In yet another embodiment, "treating" or "treatment" includes delaying the onset of the condition, disease, or disorder.

As used herein, the terms "prophylactic agent" and "prophylactic agents" refer to any agent(s) which can be used in the prevention of a condition, disease, or disorder or one or more symptoms thereof. In certain embodiments, the term "prophylactic agent" includes a compound provided herein. In certain other embodiments, the term "prophylactic agent" does not refer a compound provided herein. In certain embodiments, a prophylactic agent can be an agent which is known to be useful for, or has been or is currently being used to prevent or impede the onset, development, progression and/or severity of a condition, disease, or disorder.

As used herein, the phrase "prophylactically effective amount" refers to the amount of a therapy (e.g., prophylactic agent) which is sufficient to result in the prevention or reduction of the development, recurrence or onset of one or more symptoms associated with a condition, disease, or disorder, or to enhance or improve the prophylactic effect(s) of another therapy (e.g., another prophylactic agent).

Compounds

The embodiments described herein include the recited compounds as well as a pharmaceutically acceptable salt, hydrate, solvate, stereoisomer, tautomer, or mixture thereof.

In some or any embodiments, the Compound is according to Formula (I)-(Ij). In some or any embodiments, the pharmaceutical composition comprises a Compound according to Formula (I)-(Ij). In some or any embodiments, the method of treating comprises administering a Compound according to Formula (I)-(Ij).

In one embodiment is a Compound of Formula (I) where
$R^1$ is pyridinonyl, where the pyridinonyl is substituted on its nitrogen with $R^{1b}$ and is additionally optionally substituted with 1 $R^{1a}$;
$R^{1a}$, when present, is halo, alkyl, alkenyl, haloalkyl, cycloalkyl, cycloalkylalkyl, heterocycloalkyl, or heterocycloalkylalkyl;
$R^{1b}$ is hydrogen, alkyl, alkenyl, haloalkyl, cycloalkyl, cycloalkylalkyl, heterocycloalkyl, or heterocycloalkylalkyl;
$R^2$ is

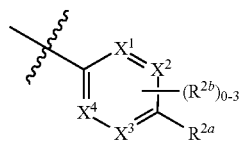

where 0, 1, or 2 of $X^1$-$X^4$ are nitrogen and the remaining are CH or $CR^{2b}$;
$R^{2a}$ is $-OR^5$, $-S(O)R^6$, or $-S(O)_2R^7$;
each $R^{2b}$, when present, is independently halo, alkyl, haloalkyl, $-NO_2$, or cyano;
$R^3$ is hydrogen, halo, alkyl, or haloalkyl;
$R^4$ is hydrogen, halo, alkyl, or haloalkyl; and
$R^5$, $R^6$, and $R^7$ are independently alkyl; haloalkyl; hydroxyalkyl; cycloalkyl; cycloalkylalkyl; heterocycloalkyl; or heterocycloalkylalkyl; where the cycloalkyl and heterocycloalkyl, alone or as part of another group, are optionally substituted with 1 or 2 groups independently selected from alkyl, hydroxy, and hydroxyalkyl; or
a stereoisomer, a mixture of stereoisomers, and/or a pharmaceutically acceptable salt thereof.

In one embodiment is a Compound of Formula (I) where
$R^1$ is pyridinonyl, where the pyridinonyl is substituted on its nitrogen with $R^{1b}$ and is additionally optionally substituted with 1 $R^{1a}$;
$R^{1a}$, when present, is halo, alkyl, alkenyl, haloalkyl, cycloalkyl, cycloalkylalkyl, heterocycloalkyl, or heterocycloalkylalkyl;
$R^{1b}$ is hydrogen, alkyl, alkenyl, haloalkyl, cycloalkyl, cycloalkylalkyl, heterocycloalkyl, or heterocycloalkylalkyl;
$R^2$ is

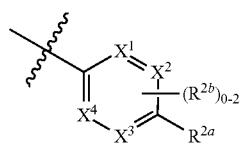

where 0, 1, or 2 of $X^1$-$X^4$ are nitrogen and the remaining are CH or $CR^{2b}$;
$R^{1a}$ is $-OR^5$, $-S(O)R^6$, or $-S(O)_2R^7$;
each $R^{2b}$, when present, is independently halo, alkyl, haloalkyl, $-NO_2$, or cyano;
$R^3$ is hydrogen, halo, alkyl, or haloalkyl;
$R^4$ is hydrogen, halo, alkyl, or haloalkyl; and
$R^5$, $R^6$, and IC are independently alkyl; haloalkyl; cycloalkyl where the cycloalkyl is optionally substituted with 1 or 2 alkyl groups; cycloalkylalkyl; heterocycloalkyl; or heterocycloalkylalkyl; or a stereoisomer, a mixture of stereoisomers, and/or a pharmaceutically acceptable salt thereof.

In one embodiment, provided is a Compound of Formula (I) where
$R^1$ is pyridinonyl, where the pyridinonyl is substituted on its nitrogen with $R^{1b}$;
$R^{1b}$ is alkyl;
$R^2$ is

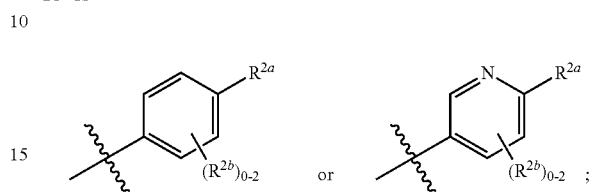

$R^{2a}$ is $-OR^5$ or $-S(O)_2R^7$;
each $R^{2b}$, when present, is halo or alkyl;
$R^3$ is hydrogen;
$R^4$ is hydrogen;
$R^5$ and $R^7$ are independently alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl, and heterocycloalkyl, alone or as part of heterocycloalkylalkyl, are optionally substituted with 1, 2, or 3 groups independently selected from hydroxy, halo, and hydroxyalkyl; or
a stereoisomer, a mixture of stereoisomers, and/or a pharmaceutically acceptable salt thereof.

In one embodiment, provided is a Compound of Formula (I) where
$R^1$ is pyridinonyl, where the pyridinonyl is substituted on its nitrogen with $R^{1b}$;
$R^{1b}$ is alkyl;
$R^2$ is

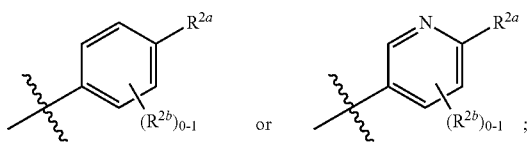

$R^{2a}$ is $-OR^5$ or $-S(O)_2R^7$;
$R^{2b}$, when present, is halo or alkyl;
$R^3$ is hydrogen;
$R^4$ is hydrogen; and
$R^5$ and $R^7$ are independently alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl, and heterocycloalkyl, alone or as part of heterocycloalkylalkyl, are optionally substituted with 1 or 2 groups independently selected from alkyl, hydroxy, halo, and hydroxyalkyl; or a stereoisomer, a mixture of stereoisomers, and/or a pharmaceutically acceptable salt thereof.

In one embodiment, provided is a Compound of Formula (I) where
R$^1$ is pyridinonyl, where the pyridinonyl is substituted on its nitrogen with R$^{1b}$;
R$^{1b}$ is alkyl;
R$^2$ is

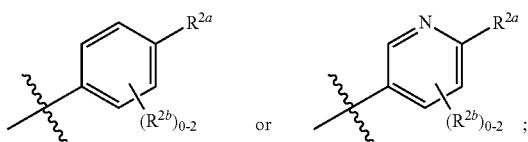

R$^{2a}$ is —OR$^5$ or —S(O)$_2$R$^7$;
each R$^{2b}$, when present, is halo or alkyl;
R$^3$ is hydrogen;
R$^4$ is hydrogen;
R$^5$ and R$^7$ are independently alkyl; haloalkyl; hydroxyalkyl; cycloalkyl; cycloalkylalkyl, or heterocycloalkylalkyl; where the cycloalkyl, alone or as part of cycloalkylalkyl, and heterocycloalkyl, alone or as part of heterocycloalkylalkyl, are optionally substituted with 1 or 2 groups independently selected from one hydroxy and hydroxyalkyl; or
a stereoisomer, a mixture of stereoisomers, and/or a pharmaceutically acceptable salt thereof.

In one embodiment, provided is a Compound of Formula (I) where
R$^1$ is pyridinonyl, where the pyridinonyl is substituted on its nitrogen with R$^{1b}$;
R$^{1b}$ is alkyl;
R$^2$ is

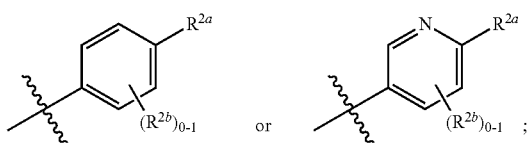

R$^{2a}$ is —OR$^5$ or —S(O)$_2$R$^7$;
R$^{2b}$, when present, is halo or alkyl;
R$^3$ is hydrogen;
R$^4$ is hydrogen; and
R$^5$ and R$^7$ are independently alkyl; haloalkyl; hydroxyalkyl; cycloalkyl; cycloalkylalkyl, heterocycloalkyl, or heterocycloalkylalkyl, where the cycloalkyl, alone or as part of cycloalkylalkyl, and heterocycloalkyl, alone or as part of heterocycloalkylalkyl, are optionally substituted with one hydroxy or hydroxyalkyl; or
a stereoisomer, a mixture of stereoisomers, and/or a pharmaceutically acceptable salt thereof.

A Compound according to Formula (Ia):

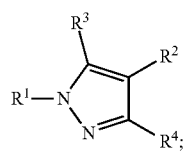

(Ia)

where R$^1$, R$^2$, R$^3$, R$^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ia) is that where R$^2$ is

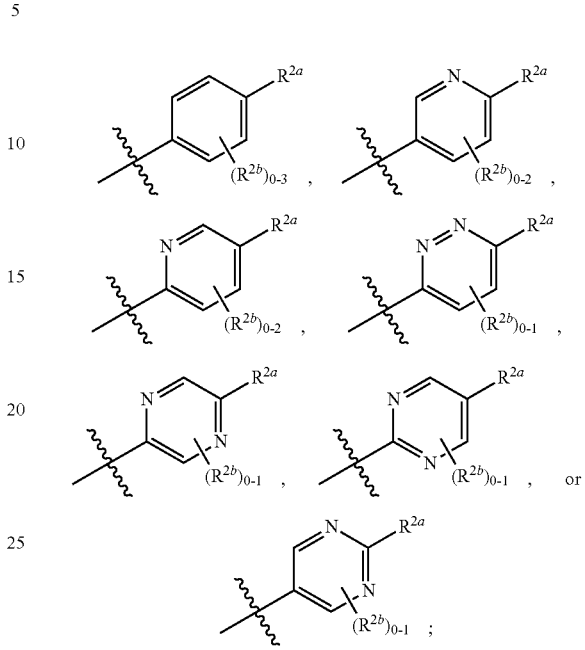

and all other groups are as defined in the Summary of the Invention for a Compound of Formula (I) or in any embodiments described herein. In some or any embodiments, the Compound of Formula (Ia) is that where R$^2$ is

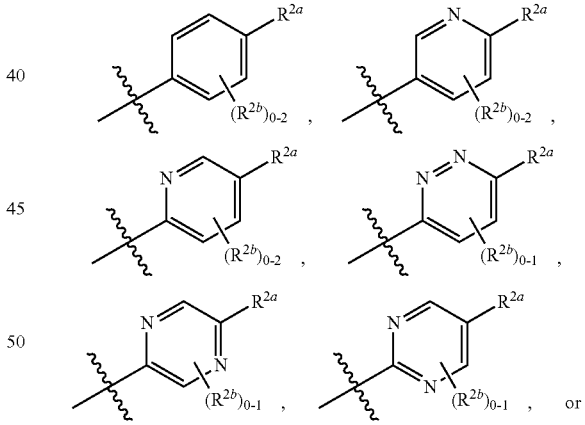

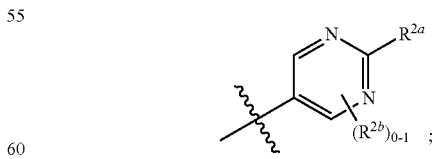

and all other groups are as defined in the Summary of the Invention for a Compound of Formula (I) or in any embodiments described herein. In some or any embodiments, the Compound of Formula (Ia) is that where R$^3$ and R$^4$ are hydrogen.

In some or any embodiments, the Compound is according to Formula (Ib):

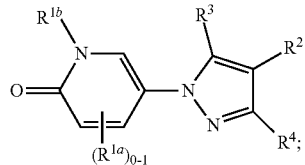

(Ib)

where $R^{1a}$, $R^{1b}$, $R^2$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ib) is that where $R^2$ is

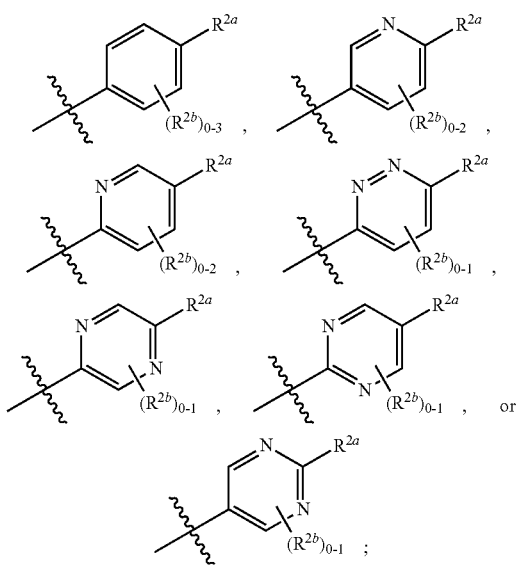

;

and all other groups are as defined in the Summary of the Invention for a Compound of Formula (I) or in any embodiments described herein. In some or any embodiments, the Compound of Formula (Ib) is that where $R^2$ is

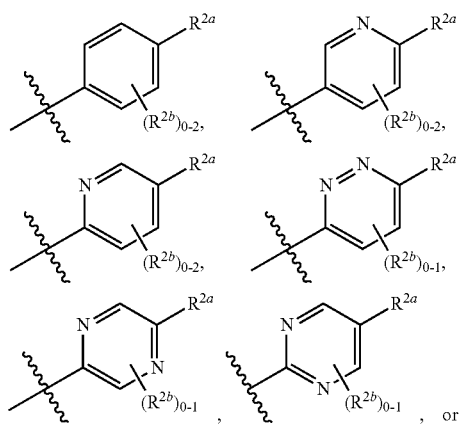

and all other groups are as defined in the Summary of the Invention for a Compound of Formula (I) or in any embodiments described herein. In some or any embodiments, the Compound of Formula (Ib) is that where $R^2$ is

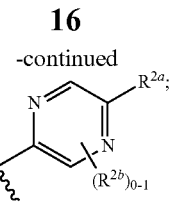

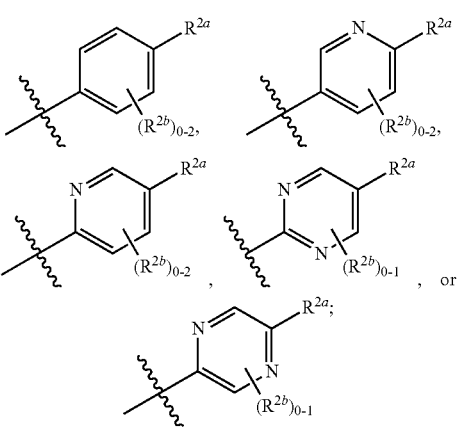

, or

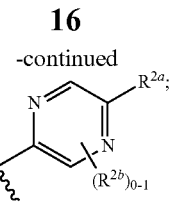

and all other groups are as defined in the Summary of the Invention for a Compound of Formula (I) or in any embodiments described herein. In some or any embodiments, the Compound of Formula (Ib) is that where $R^2$ is

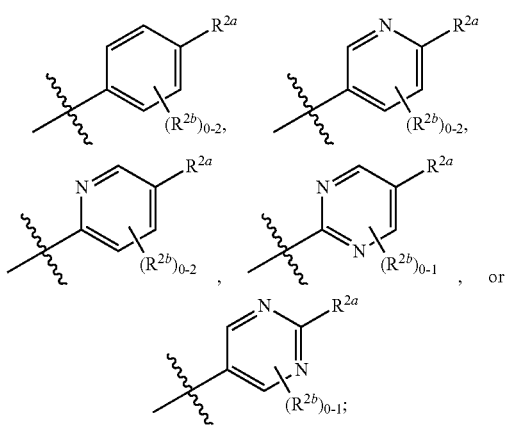

and all other groups are as defined in the Summary of the Invention for a Compound of Formula (I) or in any embodiments described herein. In some or any embodiments, the Compound of Formula (Ib) is that where $R^2$ is

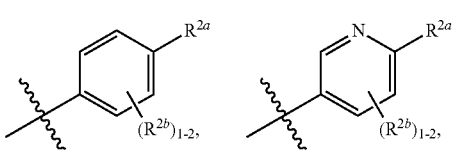

-continued

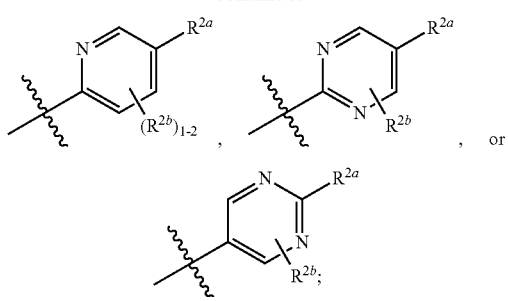
, or and all other groups are as defined in the Summary of the Invention for a Compound of Formula (I) or in any embodiments described herein. In some or any embodiments, the Compound of Formula (Ib) is that where $R^2$ is

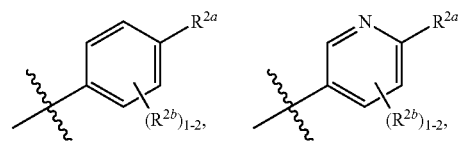

and all other groups are as defined in the Summary of the Invention for a Compound of Formula (I) or in any embodiments described herein. In some or any embodiments, the Compound of Formula (Ib) is that where $R^2$ is

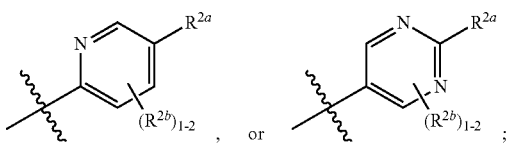

and all other groups are as defined in the Summary In some or any embodiments, the Compound of Formula (Ib) is that where $R^2$ is

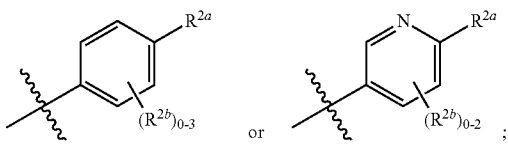

and all other groups are as defined in the Summary of the Invention for a Compound of Formula (I) or in any embodiments described herein. In some or any embodiments, the Compound of Formula (Ib) is that where $R^3$ and $R^4$ are hydrogen.

In some or any embodiments, the Compound is according to Formula (Ic):

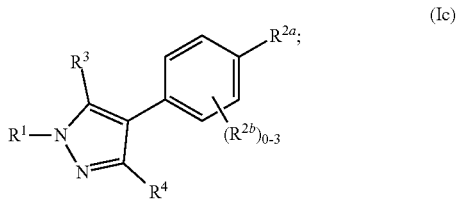

(Ic)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ic) is that wherein there are 0-2 $R^{2b}$; and all other groups are as defined in the Summary of the Invention for a Compound of Formula (I) or in any embodiments described herein. In some or any embodiments, the Compound of Formula (Ic) is that wherein $R^1$ is

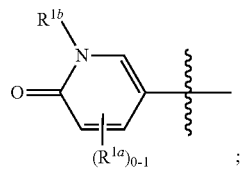

and all other groups are as defined in the Summary of the Invention for a Compound of Formula (I) or in any embodiments described herein. In some or any embodiments, the Compound of Formula (Ic) is that where $R^3$ and $R^4$ are hydrogen. In some or any embodiments, the Compound of Formula (Ic) is that where two $R^{2b}$ is present. In some or any embodiments, the Compound of Formula (Ic) is that where one $R^{2b}$ is present. In some or any embodiments, the Compound of Formula (Ic) is that where no $R^{2b}$ is present.

In some or any embodiments, the Compound is according to Formula (Id):

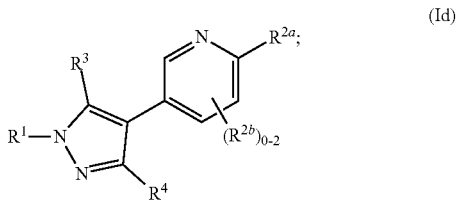

(Id)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Id) is that wherein $R^1$ is

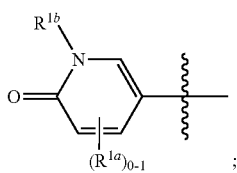

and all other groups are as defined in the Summary of the Invention for a Compound of Formula (I) or in any embodiments described herein. In some or any embodiments, the Compound of Formula (Id) is that where R³ and R⁴ are hydrogen. In some or any embodiments, the Compound of Formula (Id) is that where one $R^{2b}$ is present.

In some or any embodiments, the Compound is according to Formula (Ie):

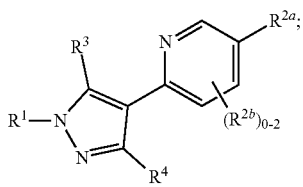

where R¹, $R^{2a}$, $R^{2b}$, R³, R⁴, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ie) is that wherein R¹ is

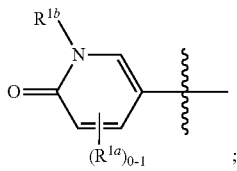

and all other groups are as defined in the Summary of the Invention for a Compound of Formula (I) or in any embodiments described herein. In some or any embodiments, the Compound of Formula (Ie) is that where R³ and R⁴ are hydrogen. In some or any embodiments, the Compound of Formula (Ie) is that where one $R^{2b}$ is present.

In some or any embodiments, the Compound is according to Formula (If):

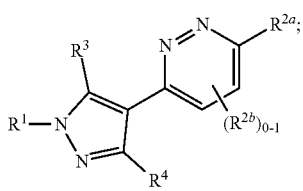

where R¹, $R^{2a}$, $R^{2b}$, R³, R⁴, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (If) is that wherein R¹ is

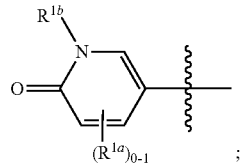

and all other groups are as defined in the Summary of the Invention for a Compound of Formula (I) or in any embodiments described herein. In some or any embodiments, the Compound of Formula (If) is that where R³ and R⁴ are hydrogen. In some or any embodiments, the Compound of Formula (If) is that where one $R^{2b}$ is present. In some or any embodiments, the Compound of Formula (If) is that where no $R^{2b}$ is present.

In some or any embodiments, the Compound is according to Formula (Ig):

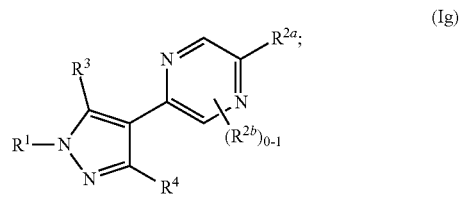

where R¹, $R^{2a}$, $R^{2b}$, R³, R⁴, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ig) is that wherein R¹ is

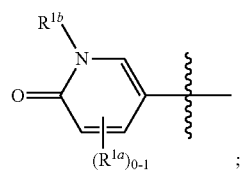

and all other groups are as defined in the Summary of the Invention for a Compound of Formula (I) or in any embodiments described herein. In some or any embodiments, the Compound of Formula (Ig) is that where R³ and R⁴ are hydrogen. In some or any embodiments, the Compound of Formula (Ig) is that where one $R^{2b}$ is present. In some or any embodiments, the Compound of Formula (Ig) is that where no $R^{2b}$ is present.

In some or any embodiments, the Compound is according to Formula (Ih):

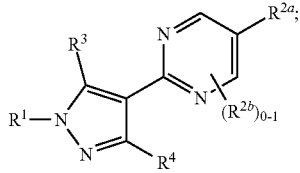

(Ih)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ih) is that wherein $R^1$ is

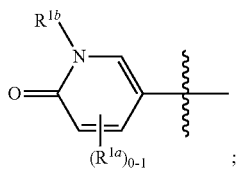

and all other groups are as defined in the Summary of the Invention for a Compound of Formula (I) or in any embodiments described herein. In some or any embodiments, the Compound of Formula (Ih) is that where $R^3$ and $R^4$ are hydrogen. In some or any embodiments, the Compound of Formula (Ih) is that where one $R^{2b}$ is present. In some or any embodiments, the Compound of Formula (Ih) is that where no $R^{2b}$ is present.

In some or any embodiments, the Compound is according to Formula (Ij):

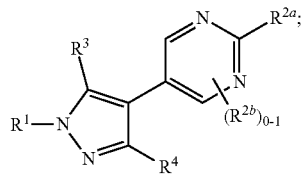

(Ij)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ij) is that wherein $R^1$ is

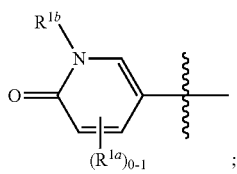

and all other groups are as defined in the Summary of the Invention for a Compound of Formula (I) or in any embodiments described herein. In some or any embodiments, the Compound of Formula (Ij) is that where $R^3$ and $R^4$ are hydrogen. In some or any embodiments, the Compound of Formula (Ij) is that where one $R^{2b}$ is present. In some or any embodiments, the Compound of Formula (Ij) is that where no $R^{2b}$ is present.

In some or any embodiments, the Compound is according to Formula (Ia-1):

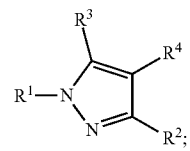

(Ia-1)

where $R^1$, $R^2$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ia-1) is that where $R^2$ is

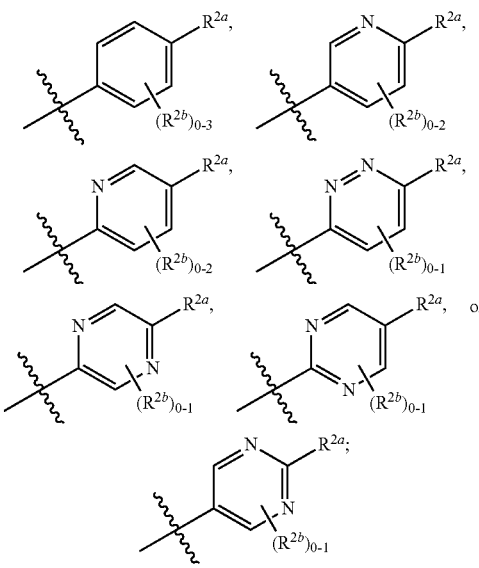

and all other groups are as defined in the Summary of the Invention for a Compound of Formula (I) or in any embodiments described herein. In some or any embodiments, the Compound of Formula (Ia-1) is that where $R^2$ is

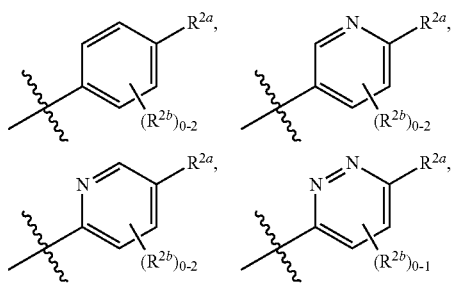

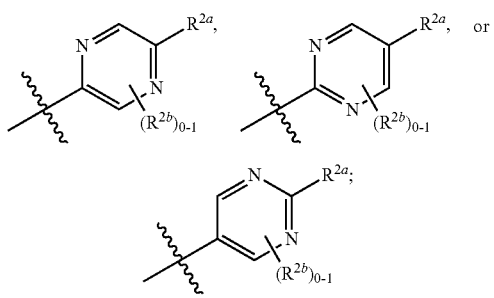

and all other groups are as defined in the Summary of the Invention for a Compound of Formula (I) or in any embodiments described herein. In some or any embodiments, the Compound of Formula (Ia-1) is that where $R^2$ is

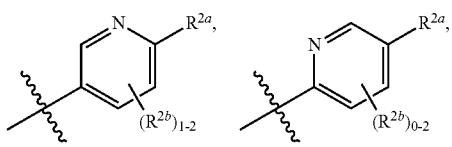

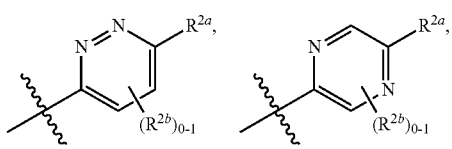

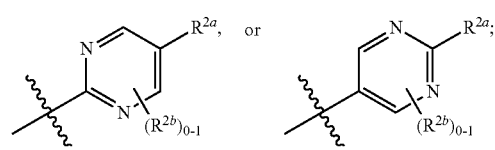

and all other groups are as defined in the Summary of the Invention for a Compound of Formula (I) or in any embodiments described herein. In some or any embodiments, the Compound of Formula (Ia-1) is that where $R^3$ and $R^4$ are hydrogen.

In some or any embodiments, the Compound is according to Formula (Ib-1):

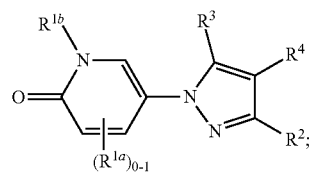

where $R^{1a}$, $R^{1b}$, $R^2$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ib-1) is that where $R^2$ is

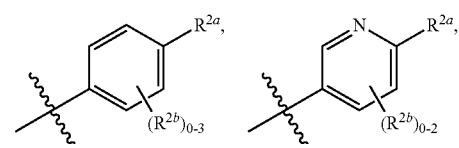

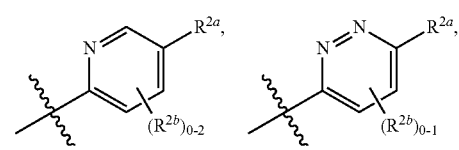

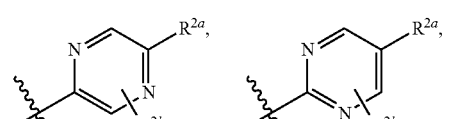

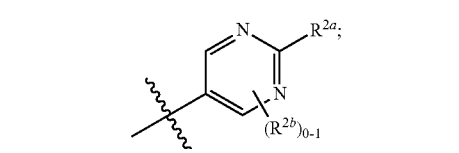

and all other groups are as defined in the Summary of the Invention for a Compound of Formula (I) or in any embodiments described herein. In some or any embodiments, the Compound of Formula (Ib-1) is that where $R^2$ is

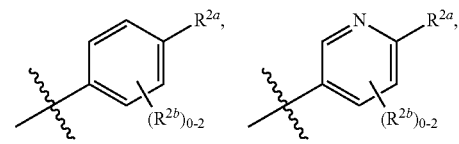

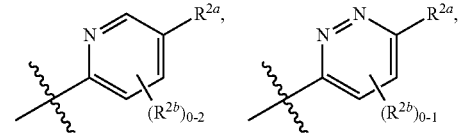

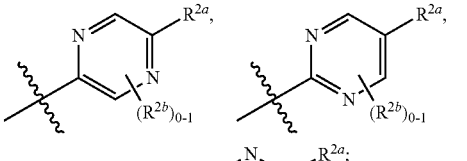

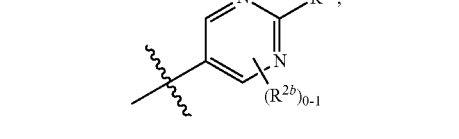

and all other groups are as defined in the Summary of the Invention for a Compound of Formula (I) or in any embodiments described herein. In some or any embodiments, the Compound of Formula (Ib-1) is that where $R^2$ is

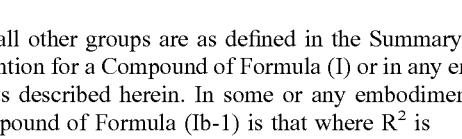

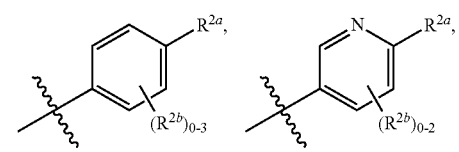

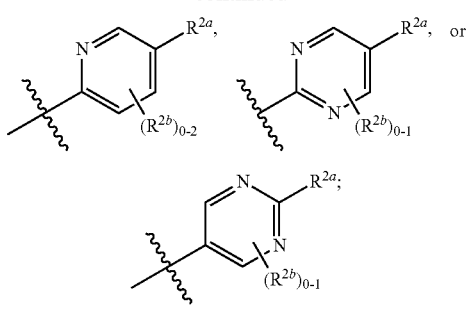

and all other groups are as defined in the Summary of the Invention for a Compound of Formula (I) or in any embodiments described herein. In some or any embodiments, the Compound of Formula (Ib-1) is that where $R^2$ is

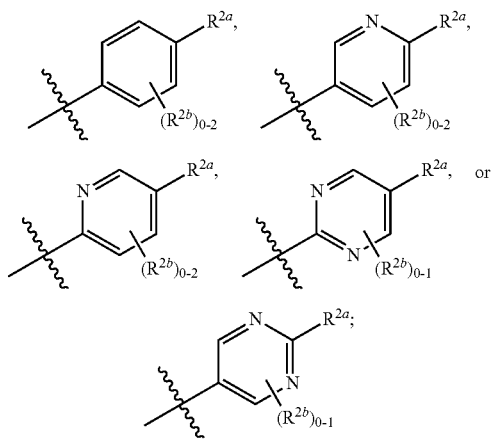

and all other groups are as defined in the Summary of the Invention for a Compound of Formula (I) or in any embodiments described herein. In some or any embodiments, the Compound of Formula (Ib-1) is that where $R^2$ is

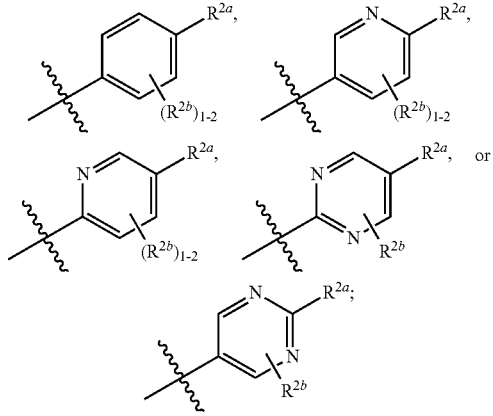

and all other groups are as defined in the Summary of the Invention for a Compound of Formula (I) or in any embodiments described herein. In some or any embodiments, the Compound of Formula (Ib-1) is that where $R^2$ is

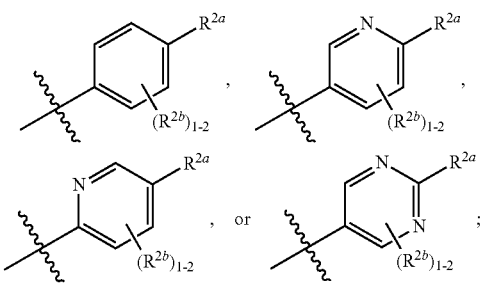

and all other groups are as defined in the Summary of the Invention for a Compound of Formula (I) or in any embodiments described herein. In some or any embodiments, the Compound of Formula (Ib-1) is that where $R^2$ is

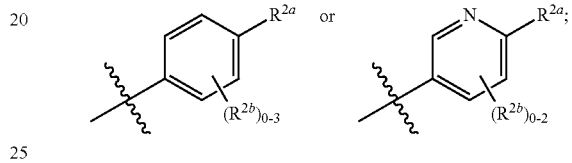

and all other groups are as defined in the Summary of the Invention for a Compound of Formula (I) or in any embodiments described herein. In some or any embodiments, the Compound of Formula (Ib-1) is that where $R^3$ and $R^4$ are hydrogen.

In some or any embodiments, the Compound is according to Formula (Ic-1):

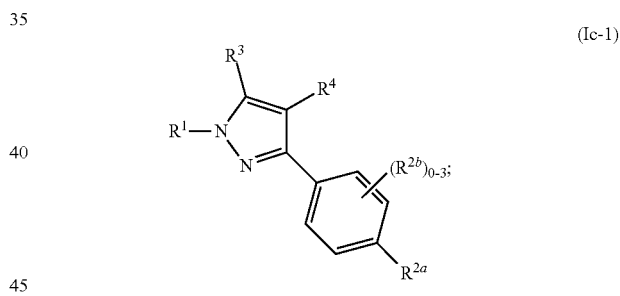

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ic-1) is that wherein there are 0-2 $R^{2b}$; and all other groups are as defined in the Summary of the Invention for a Compound of Formula (I) or in any embodiments described herein. In some or any embodiments, the Compound of Formula (Ic-1) is that wherein $R^1$ is

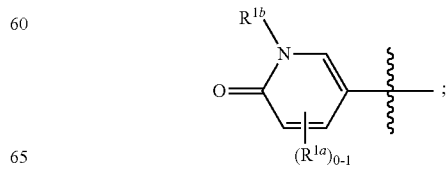

and all other groups are as defined in the Summary of the Invention for a Compound of Formula (I) or in any embodiments described herein. In some or any embodiments, the Compound of Formula (Ic-1) is that where $R^3$ and $R^4$ are hydrogen. In some or any embodiments, the Compound of Formula (Ic-1) is that where two $R^{2b}$ is present. In some or any embodiments, the Compound of Formula (Ic-1) is that where one $R^{2b}$ is present. In some or any embodiments, the Compound of Formula (Ic-1) is that where no $R^{2b}$ is present.

In some or any embodiments, the Compound is according to Formula (Id-1):

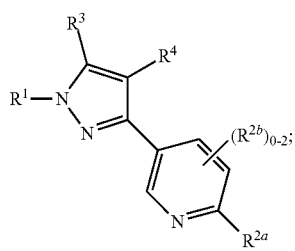

(Id-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Id-1) is that wherein $R^1$ is

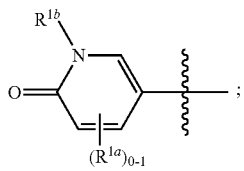

;

and all other groups are as defined in the Summary of the Invention for a Compound of Formula (I) or in any embodiments described herein. In some or any embodiments, the Compound of Formula (Id-1) is that where $R^3$ and $R^4$ are hydrogen. In some or any embodiments, the Compound of Formula (Id-1) is that where one $R^{2b}$ is present.

In some or any embodiments, the Compound is according to Formula (Ie-1):

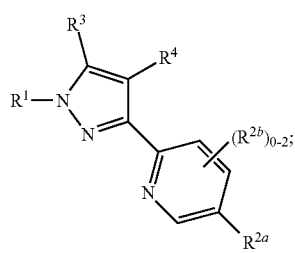

(Ie-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ie-1) is that wherein $R^1$ is

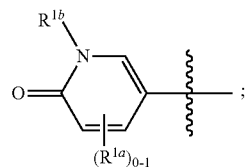

;

and all other groups are as defined in the Summary of the Invention for a Compound of Formula (I) or in any embodiments described herein. In some or any embodiments, the Compound of Formula (Ie-1) is that where $R^3$ and $R^4$ are hydrogen. In some or any embodiments, the Compound of Formula (Ie-1) is that where one $R^{2b}$ is present.

In some or any embodiments, the Compound is according to Formula (If-1):

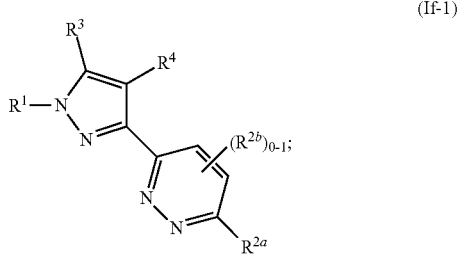

(If-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (If-1) is that wherein $R^1$ is

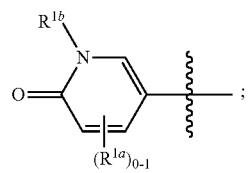

;

and all other groups are as defined in the Summary of the Invention for a Compound of Formula (I) or in any embodiments described herein. In some or any embodiments, the Compound of Formula (If-1) is that where $R^3$ and $R^4$ are hydrogen. In some or any embodiments, the Compound of Formula (If-1) is that where one $R^{2b}$ is present. In some or any embodiments, the Compound of Formula (If-1) is that where no $R^{2b}$ is present.

In some or any embodiments, the Compound is according to Formula (Ig-1):

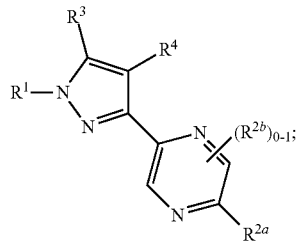

(Ig-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ig-1) is that wherein $R^1$ is

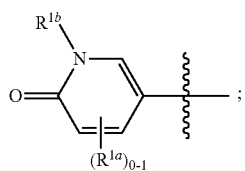

and all other groups are as defined in the Summary of the Invention for a Compound of Formula (I) or in any embodiments described herein. In some or any embodiments, the Compound of Formula (Ig-1) is that where $R^3$ and $R^4$ are hydrogen. In some or any embodiments, the Compound of Formula (Ig-1) is that where one $R^{2b}$ is present. In some or any embodiments, the Compound of Formula (Ig-1) is that where no $R^{2b}$ is present.

In some or any embodiments, the Compound is according to Formula (Ih-1):

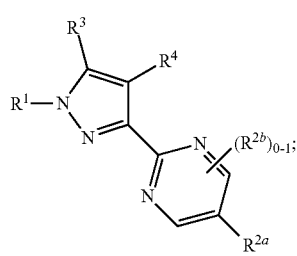

(Ih-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ih-1) is that wherein $R^1$ is

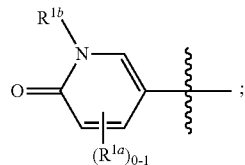

and all other groups are as defined in the Summary of the Invention for a Compound of Formula (I) or in any embodiments described herein. In some or any embodiments, the Compound of Formula (Ih-1) is that where $R^3$ and $R^4$ are hydrogen. In some or any embodiments, the Compound of Formula (Ih-1) is that where one $R^{2b}$ is present. In some or any embodiments, the Compound of Formula (Ih-1) is that where no $R^{2b}$ is present.

In some or any embodiments, the Compound is according to Formula (Ij-1):

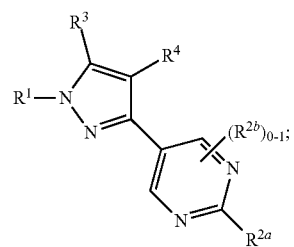

(Ij-1)

where $R^1$, $R^{2a}$, $R^{2b}$, $R^3$, $R^4$, and all other groups are as defined in the Summary of the Invention for a Compound of Formula (I) or in any embodiments described herein; or a stereoisomer, a mixture of stereoisomers, and/or a pharmaceutically acceptable salt thereof. In some or any embodiments, the Compound of Formula (Ij-1) is that wherein $R^1$ is

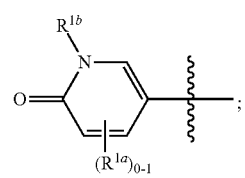

and all other groups are as defined in the Summary of the Invention for a Compound of Formula (I) or in any embodiments described herein. In some or any embodiments, the Compound of Formula (Ij-1) is that where $R^3$ and $R^4$ are hydrogen. In some or any embodiments, the Compound of Formula (Ij-1) is that where one $R^{2b}$ is present. In some or any embodiments, the Compound of Formula (Ij-1) is that where no $R^{2b}$ is present.

In some or any embodiments, the Compound of Formula (I)-(Ij) or (Ia-1)-(Ij-1) is that where $R^3$ and $R^4$ are hydrogen; $R^3$ and $R^4$ are alkyl; or one of $R^3$ and $R^4$ is hydrogen and the other is alkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^3$ and $R^4$ are hydrogen; $R^3$ and $R^4$ are methyl; $R^3$ is hydrogen and $R^4$ is methyl; or $R^3$ is methyl and $R^4$ is hydrogen; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^3$ and $R^4$ are hydrogen; and all other groups are as defined in the Summary of the Invention for a Compound of Formula (I) or in any embodiments described herein.

In some or any embodiments, the Compound of Formula (I)-(Ij), (Ia-1)-(Ij-1) is that where $R^1$ is pyridinonyl substituted on its nitrogen with $R^{1b}$ and additionally optionally substituted with 1 $R^{1a}$; $R^{1b}$ is alkyl, alkenyl, haloalkyl, cycloalkyl, cycloalkylalkyl, heterocycloalkyl, or heterocycloalkylalkyl; and all other groups are as defined in the Summary of the Invention for a Compound of Formula (I) or in any embodiments described herein. In some or any embodiments, the Compound of Formula (I)-(Ij), (Ia-1)-(Ij-1) is that where $R^1$ is pyridinonyl substituted on its nitrogen with $R^{1b}$ and additionally optionally substituted with 1 $R^{1a}$; $R^{1b}$ is alkyl; and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

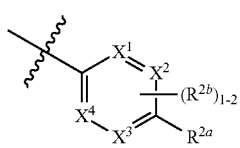

where 0, 1, or 2 of $X^1$-$X^4$ are nitrogen and the remaining are CH or $CR^{2b}$; and all other groups are as defined in the Summary of the Invention for a Compound of Formula (I) or in any embodiments described herein. In some of any embodiment, the Compound of Formula (I), (Ia), (Ib), (Ia-1), or (Ib-1) is that where $R^2$ is

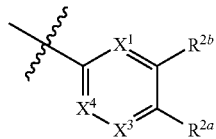

where 0, 1, or 2 of $X^1$, $X^3$, and $X^4$ are nitrogen and the remaining are CH or $CR^{2b}$; and all other groups are as defined in the Summary of the Invention for a Compound of Formula (I) or in any embodiments described herein. In some of any embodiment, the Compound of Formula (I), (Ia), (Ib), (Ia-1), or (Ib-1) is that where $R^2$ is

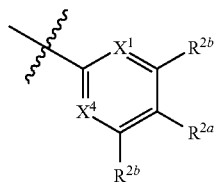

where 0, 1, or 2 of $X^2$, $X^3$, and $X^4$ are nitrogen and the remaining are CH or $CR^{2b}$; and each $R^{2b}$ is independently selected; and all other groups are as defined in the Summary of the Invention for a Compound of Formula (I) or in any embodiments described herein. In some of any embodiment, the Compound of Formula (I), (Ia), (Ib), (Ia-1), or (Ib-1) is that where $R^2$ is

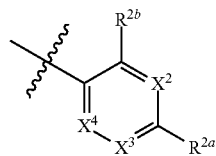

where 0, 1, or 2 of $X^2$, $X^3$, and $X^4$ are nitrogen and the remaining are CH or $CR^{2b}$; and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

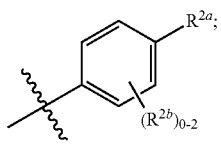

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

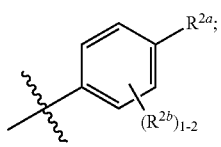

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

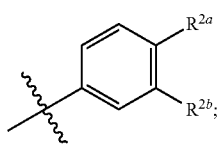

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

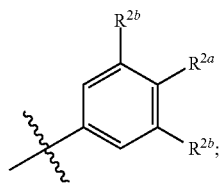

and each $R^{2b}$ is independently selected; and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

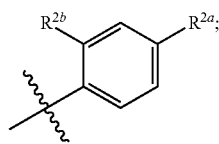

and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

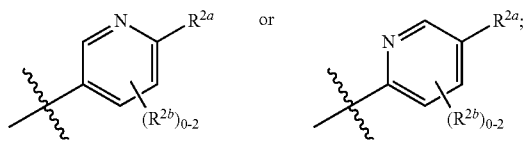

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

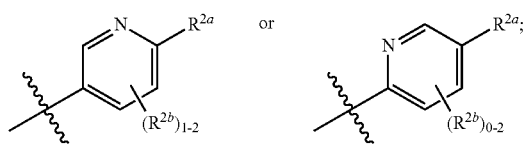

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

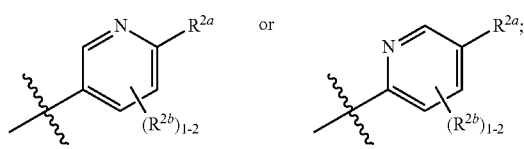

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

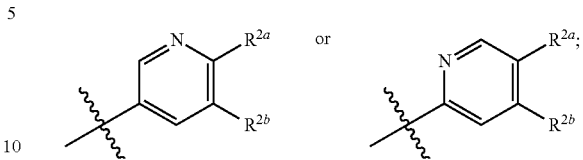

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

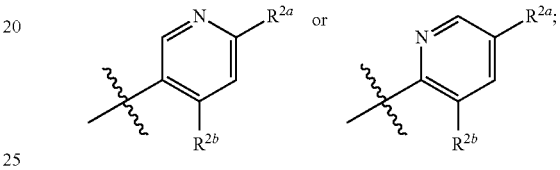

and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

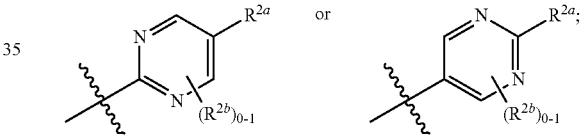

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

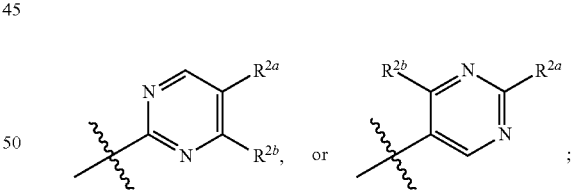

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

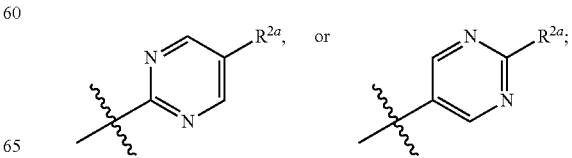

and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

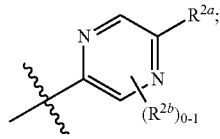

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

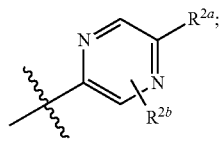

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

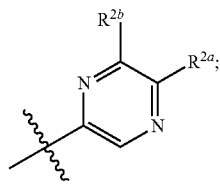

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

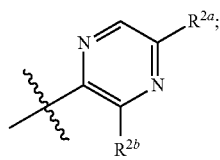

and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

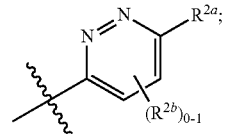

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

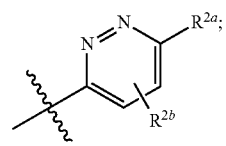

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

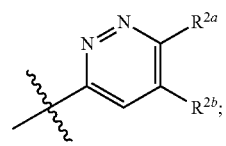

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

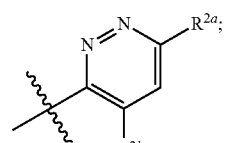

and all other groups are as defined in the Summary of the Invention for a Compound of Formula (I) or in any embodiments described herein.

In some or any embodiments, the Compound of Formula (I), (Ia), (Ib), (Ia-1), or (Ib-1) is that where $R^2$ is

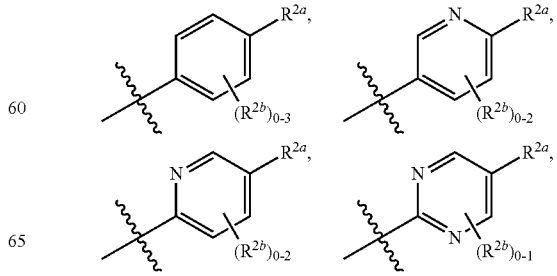

-continued

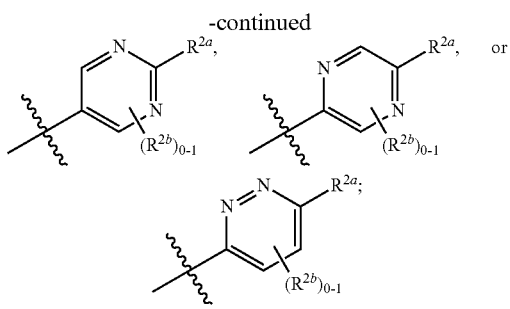
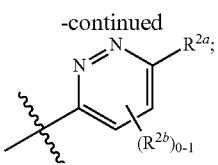

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

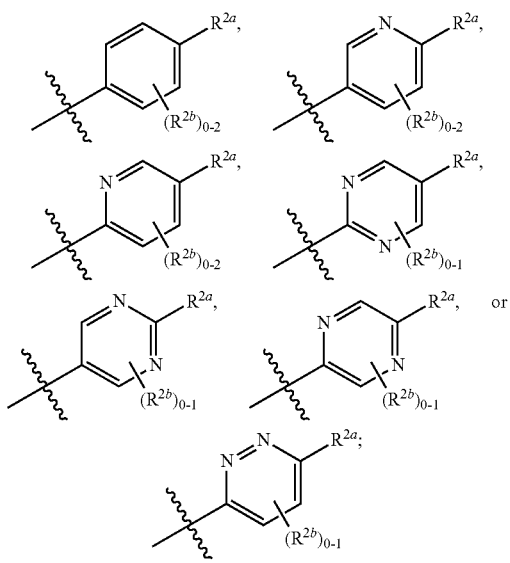

and all other groups are as defined in the Summary of the Invention for a Compound of Formula (I) or in any embodiments described herein. In some or any embodiments, the Compound of Formula (I), (Ia), (Ib), (Ia-1), or (Ib-1) is that where $R^2$ is

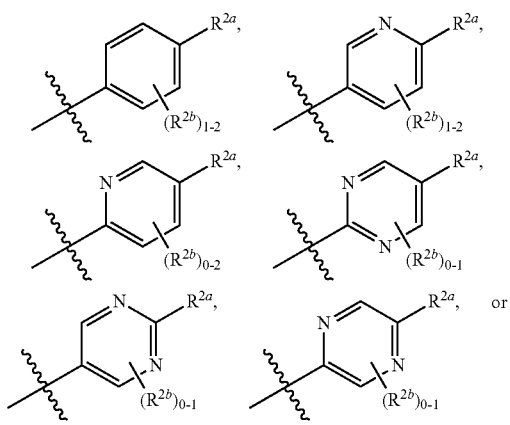

and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is $-OR^5$; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is $-OR^5$; $R^5$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl and heterocycloalkyl in $R^5$, alone or as part of heterocycloalkylalkyl, are optionally substituted with 1, 2, or 3 groups independently selected from alkyl, hydroxy, halo, and hydroxyalkyl;

and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is alkyl; haloalkyl; hydroxyalkyl; haloalkyl further substituted with 1 or 2 hydroxy; cycloalkyl; cycloalkylalkyl; or heterocycloalkylalkyl; where the cycloalkyl in $R^5$, alone or as part of cycloalkylalkyl and heterocycloalkyl in $R^5$, as part of heterocycloalkylalkyl, are optionally substituted with 1 or 2 groups independently selected from alkyl, hydroxy, and hydroxyalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —$OR^5$; $R^5$ is alkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2'}$ is —$OR^5$; $R^5$ is haloalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is haloalkyl further substituted with 1 or 2 hydroxy; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is cycloalkyl which is optionally substituted with 1 or 2 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is cycloalkylalkyl where the cycloalkyl is optionally substituted with 1 or 2 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is heterocycloalkylalkyl where the heterocycloalkyl is optionally substituted with 1 or 2 groups independently selected from alkyl, hydroxy, halo, and hydroxyalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is -$OR^5$; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is alkyl; haloalkyl; hydroxyalkyl; haloalkyl further substituted with 1 or 2 hydroxy; cycloalkyl; cycloalkylalkyl; or heterocycloalkylalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is -$OR^5$; $R^5$ is $C_4$-$C_8$-alkyl; haloalkyl; hydroxyalkyl; haloalkyl further substituted with 1 or 2 hydroxy; cycloalkyl where the cycloalkyl is optionally substituted with 1 or 2 groups independently selected from alkyl, hydroxy, and hydroxyalkyl groups; cycloalkylalkyl where the cycloalkyl is optionally substituted with 1 or 2 groups independently selected from alkyl, hydroxy, and hydroxyalkyl groups; heterocycloalkyl where the heterocycloalkyl is optionally substituted with 1 or 2 groups independently selected from alkyl, hydroxy, and hydroxyalkyl groups; or heterocycloalkylalkyl where the heterocycloalkyl is optionally substituted with 1 or 2 groups independently selected from alkyl, hydroxy, and hydroxyalkyl groups; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is $C_4$-$C_8$-alkyl, haloalkyl, hydroxyalkyl, haloalkyl further substituted with 1 or 2 hydroxy; cycloalkyl, cycloalkylalkyl, heterocycloalkyl, or heterocycloalkylalkyl; where the cycloalkyl and heterocycloalkyl are optionally substituted with 1 or 2 groups which are independently hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is $C_4$-$C_8$-alkyl, haloalkyl, hydroxyalkyl, haloalkyl further substituted with 1 or 2 hydroxy; cycloalkyl, cycloalkylalkyl, or heterocycloalkylalkyl; where the cycloalkyl and heterocycloalkyl are optionally substituted with 1 or 2 groups which are independently hydroxyalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is -$OR^5$; $R^5$ is $C_4$-$C_8$-alkyl; haloalkyl; cycloalkyl where the cycloalkyl is optionally substituted with 1 or 2 alkyl groups; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is $C_4$-$C_8$-alkyl; haloalkyl; hydroxyalkyl; haloalkyl further substituted with 1 or 2 hydroxy; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$OR^5$; $R^5$ is $C_4$-$C_8$-alkyl, haloalkyl, cycloalkyl, or cycloalkylalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —$S(O)R^6$; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —$S(O)R^6$ and $R^6$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl (alone or as part of cycloalkylalkyl) and heterocycloalkyl (alone or as part of heterocycloalkylalkyl) are optionally substituted with 1 or 2 groups which are independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is alkyl, haloalkyl, hydroxyalkyl; cycloalkyl, cycloalkylalkyl, or heterocycloalkyl; where the cycloalkyl and heterocycloalkyl are optionally substituted with 1 or 2 groups which are independently hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is alkyl or haloalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is alkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is hydroxyalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —S(O)$R^6$; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$R^6$ and $R^6$ is alkyl, haloalkyl, cycloalkyl, cycloalkylalkyl, or heterocycloalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —S(O)$_2R^7$; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl, and heterocycloalkyl, alone or as part of heterocycloalkylalkyl, are optionally substituted with 1, 2, or 3 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl, haloalkyl, hydroxyalkyl; cycloalkyl, cycloalkylalkyl, heterocycloalkyl, or heterocycloalkylalkyl; where the cycloalkyl (alone or as part of cycloalkylalkyl) and heterocycloalkyl, alone or as part of heterocycloalkylalkyl, are optionally substituted with 1 or 2 groups independently selected from alkyl, hydroxy, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl or haloalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —S(O)$_2R^7$ and $R^7$ is alkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is cycloalkyl which is optionally substituted with 1 or 2 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is cycloalkylalkyl where the cycloalkyl is optionally substituted with 1 or 2 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and IC is heterocycloalkyl which is optionally substituted with 1 or 2 groups independently selected from alkyl, hydroxy, halo, and hydroxyalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is —S(O)$_2R^7$ and $R^7$ is alkyl; haloalkyl; hydroxyalkyl; haloalkyl further substituted with 1 or 2 hydroxy; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl, haloalkyl, cycloalkyl, cycloalkylalkyl, or heterocycloalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl or haloalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2R^7$ and $R^7$ is alkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)

$_2R^7$ and $R^7$ is cycloalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2$R$^7$ and R$^7$ is cycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2$R$^7$ and R$^7$ is heterocycloalkyl; and all other groups are as defined in the Summary of the Invention for a Compound of Formula (I) or in any embodiments described herein.

In some or any embodiments, the Compound of Formula (I)-(Ij) or (Ia-1)-(Ij-1) is that where $R^{2a}$ is –OR$^5$, —S(O)R$^6$, or —S(O)$_2$R$^7$; R$^5$ is $C_4$-$C_8$-alkyl; hydroxyalkyl; haloalkyl; haloalkyl further substituted with 1 or 2 hydroxy; cycloalkyl where the cycloalkyl is optionally substituted with 1 or 2 groups independently selected from alkyl, hydroxy, halo, and hydroxyalkyl; cycloalkylalkyl where the cycloalkyl is optionally substituted with 1 or 2 groups independently selected from alkyl, hydroxy, halo, and hydroxyalkyl; heterocycloalkyl where the heterocycloalkyl is optionally substituted with 1 or 2 groups independently selected from alkyl, hydroxy, halo, and hydroxyalkyl; or heterocycloalkylalkyl where the heterocycloalkyl is optionally substituted with 1 or 2 groups independently selected from alkyl, hydroxy, halo, and hydroxyalkyl; and R$^6$ and R$^7$ are independently alkyl; haloalkyl; hydroxyalkyl; haloalkyl further substituted with 1 or 2 hydroxy; cycloalkyl where the cycloalkyl is optionally substituted with 1 or 2 groups independently selected from alkyl, hydroxy, halo, and hydroxyalkyl; cycloalkylalkyl where the cycloalkyl is optionally substituted with 1 or 2 groups independently selected from alkyl, hydroxy, halo, and hydroxyalkyl; heterocycloalkyl where the heterocycloalkyl is optionally substituted with 1 or 2 groups independently selected from alkyl, hydroxy, halo, and hydroxyalkyl; or heterocycloalkylalkyl where the heterocycloalkyl is optionally substituted with 1 or 2 groups independently selected from alkyl, hydroxy, halo, and hydroxyalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —OR$^5$, —S(O)R$^6$, or —S(O)$_2$R$^7$; R$^5$ is $C_4$-$C_8$-alkyl; haloalkyl; hydroxyalkyl; haloalkyl further substituted with 1 or 2 hydroxy; cycloalkyl; cycloalkylalkyl; heterocycloalkyl; or heterocycloalkylalkyl; and R$^6$ and R$^7$ are independently alkyl; haloalkyl; hydroxyalkyl; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —OR$^5$, —S(O)R$^6$, or —S(O)$_2$R$^7$; R$^5$ is $C_4$-$C_8$-alkyl, haloalkyl, hydroxyalkyl, haloalkyl further substituted with 1 or 2 hydroxy; cycloalkyl, cycloalkylalkyl, or heterocycloalkylalkyl; and R$^6$ and R$^7$ are independently alkyl, haloalkyl, hydroxyalkyl, cycloalkyl, cycloalkylalkyl, or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —S(O)$_2$R$^7$; R$^5$ is $C_4$-$C_8$-alkyl; haloalkyl; cycloalkyl where the cycloalkyl is optionally substituted with 1 or 2 alkyl groups; cycloalkylalkyl; heterocycloalkyl; or heterocycloalkylalkyl; and R$^6$ and R$^7$ are independently alkyl; haloalkyl; cycloalkyl where the cycloalkyl is optionally substituted with 1 or 2 alkyl groups; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —OR$^5$, —S(O)R$^6$, or —S(O)$_2$R$^7$; R$^5$ is $C_4$-$C_8$-alkyl, haloalkyl, cycloalkyl, cycloalkylalkyl, heterocycloalkyl, or heterocycloalkylalkyl; and R$^6$ and R$^7$ are independently alkyl; haloalkyl; cycloalkyl; cycloalkylalkyl; heterocycloalkyl; or heterocycloalkylalkyl; and all other groups are as defined in the Summary of the Invention for a Compound of Formula (I) or in any embodiments described herein. In some or any embodiments, the Compound of Formula (I)-(Ij) or (Ia-1)-(Ij-1) is that where $R^{2a}$ is —OR$^5$, —S(O)R$^6$, or —S(O)$_2$R$^7$; R$^5$ is $C_4$-$C_8$-alkyl, haloalkyl, cycloalkyl, or cycloalkylalkyl; and R$^6$ and R$^7$ are independently alkyl; haloalkyl; cycloalkyl; or cycloalkylalkyl; and all other groups are as defined in the Summary of the Invention for a Compound of Formula (I) or in any embodiments described herein.

Embodiment 1

Provided is a Compound of Formula (I):

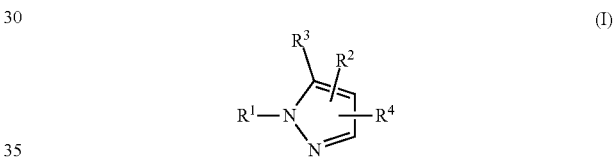

where
R$^1$ is pyridinonyl, where the pyridinonyl is substituted on its nitrogen with R$^{1b}$ and is additionally optionally substituted with 1 R$^{1a}$;
R$^{1a}$, when present, is halo, alkyl, alkenyl, haloalkyl, cycloalkyl, cycloalkylalkyl, heterocycloalkyl, or heterocycloalkylalkyl;
R$^{1b}$ is hydrogen, alkyl, alkenyl, haloalkyl, cycloalkyl, cycloalkylalkyl, heterocycloalkyl, or heterocycloalkylalkyl;
R$^2$ is

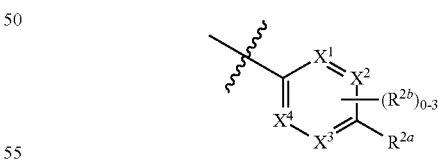

where 0, 1, or 2 of $X^1$-$X^4$ are nitrogen and the remaining are CH or CR$^{2b}$;
R$^{2a}$ is –OR$^5$, —S(O)R$^6$, or —S(O)$_2$R$^7$;
each R$^{2b}$, when present, is independently halo, alkyl, haloalkyl, —NO$_2$, or cyano;
R$^3$ is hydrogen, halo, alkyl, or haloalkyl;
R$^4$ is hydrogen, halo, alkyl, or haloalkyl; and
R$^5$, R$^6$, and R$^7$ are independently alkyl; haloalkyl; hydroxyalkyl; haloalkyl further substituted with 1 or 2 hydroxy; cycloalkyl; cycloalkylalkyl; heterocycloalkyl; or heterocycloalkylalkyl; where the cycloalkyl, alone or as part of cycloalkylalkyl, and heterocycloalkyl, alone or as part of heterocycloalkylalkyl, are optionally substituted with 1, 2, or 3 groups independently selected from alkyl, hydroxy, halo, and hydroxyalkyl; or a stereoisomer, a mixture of stereoisomers, and/or a pharmaceutically acceptable salt thereof.

Embodiment 2

Provided is the Compound of Embodiment 1 according to Formula (Ia):

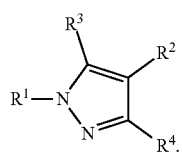

(Ia)

Embodiment 3

Provided is the Compound of Embodiment 1 or 2 according to Formula (Ib):

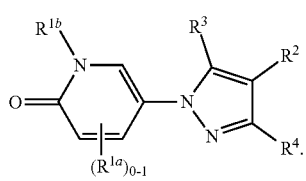

(Ib)

Embodiment 4

Provided is the Compound of Embodiment 1, 2, or 3 where $R^3$ and $R^4$ are hydrogen.

Embodiment 5

Provided is the Compound of Embodiment 1, 2, or 3 where $R^3$ and $R^4$ are methyl.

Embodiment 6

Provided is the Compound of Embodiment 1, 2, or 3 where $R^3$ is hydrogen and $R^4$ is methyl.

Embodiment 7

Provided is the Compound of Embodiment 1, 2, or 3 where $R^3$ is methyl and $R^4$ is hydrogen.

Embodiment 8

Provided is the Compound of any one of Embodiments 1-7 where $R^2$ is

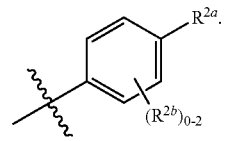

Embodiment 9

Provided is the Compound of any one of Embodiments 1-7 where $R^2$ is

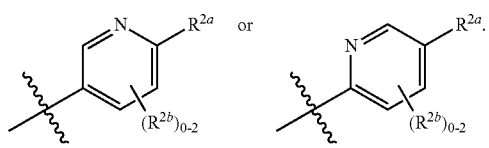

Embodiment 10

Provided is the Compound of any one of Embodiments 1-7 where $R^2$ is

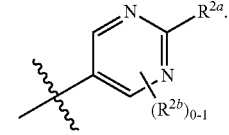

Embodiment 11

Provided is the Compound of any one of Embodiments 1-7 where $R^2$ is

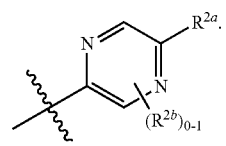

Embodiment 12

Provided is the Compound of any one of Embodiments 1-7 where $R^2$ is

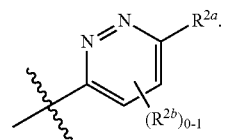

Embodiment 13

Provided is the Compound of any one of Embodiments 1-12 where the $R^2$ ring is substituted with a first $R^{2b}$.

Embodiment 14

Provided is the Compound of any one of Embodiments 1-13 where the first $R^{2b}$, when present, is halo.

Embodiment 15

Provided is the Compound of any one of Embodiments 1-14 where the first $R^{2b}$, when present, is chloro.

Embodiment 16

Provided is the Compound of any one of Embodiments 1-14 where the first $R^{2b}$, when present, is fluoro.

Embodiment 17

Provided is the Compound of any one of Embodiments 1-13 where the first $R^{2b}$, when present, is —CN.

Embodiment 18

Provided is the Compound of any one of Embodiments 1-13 where the first $R^{2b}$, when present, is —CH$_3$.

Embodiment 19

Provided is the Compound of any one of Embodiments 1-13 where the first $R^{2b}$, when present, is —CF$_3$.

Embodiment 20

Provided is the Compound of any one of Embodiments 1-19 where the $R^2$ ring is substituted with a second $R^{2b}$.

Embodiment 21

Provided is the Compound of any one of Embodiments 1-20 where the second $R^{2b}$, when present, is halo.

Embodiment 22

Provided is the Compound of any one of Embodiments 1-21 where the second $R^{2b}$, when present, is chloro.

Embodiment 23

Provided is the Compound of any one of Embodiments 1-21 where the second $R^{2b}$, when present, is fluoro.

Embodiment 24

Provided is the Compound of any one of Embodiments 1-20 where the second $R^{2b}$, when present, is —CN.

Embodiment 25

Provided is the Compound of any one of Embodiments 1-20 where the second $R^{2b}$, when present, is —CH$_3$.

Embodiment 26

Provided is the Compound of any one of Embodiments 1-20 where the second $R^{2b}$, when present, is —CF$_3$.

Embodiment 27

Provided is the Compound of any one of Embodiments 1-26 where $R^{2a}$ is —S(O)$_2$R$^7$.

Embodiment 28

Provided is the Compound of any one of Embodiments 1-26 where $R^{2a}$ is —S(O)R$^6$.

Embodiment 29

Provided is the Compound of any one of Embodiments 1-26 where $R^{2a}$ is —OR$^5$.

Embodiment 30

Provided is the Compound of any one of Embodiments 1-29 where $R^5$, $R^6$, and $R^7$ are independently alkyl.

Embodiment 31

Provided is the Compound of any one of Embodiments 1-29 where $R^5$, $R^6$, and $R^7$ are independently haloalkyl.

Embodiment 31

Provided is the Compound of any one of Embodiments 1-29 where $R^5$, $R^6$, and $R^7$ are independently cycloalkyl where the cycloalkyl is optionally substituted with 1 or 2 groups that are independently hydroxyalkyl.

Embodiment 32

Provided is the Compound of any one of Embodiments 1-29 where $R^5$, $R^6$, and $R^7$ are independently cycloalkylalkyl where the cycloalkyl is optionally substituted with 1 or 2 groups that are independently hydroxyalkyl.

Embodiment 33

Provided is the Compound of any one of Embodiments 1-29 where $R^5$, $R^6$, and $R^7$ are independently hydroxyalkyl.

Embodiment 34

Provided is the Compound of any one of Embodiments 1-29 where $R^5$, $R^6$, and $R^7$ are independently heterocycloalkylalkyl where the heterocycloalkyl, alone or as part of heterocycloalkylalkyl is optionally substituted with 1 or 2 groups that are independently hydroxyalkyl.

Embodiment 35

Provided is the Compound of any one of Embodiments 1-29 where $R^5$, $R^6$, and $R^7$ are independently heterocycloalkyl which is optionally substituted with 1 or 2 groups that are independently halo.

Embodiment 36

Provided is the Compound of any one of Embodiments 1-29 where $R^5$, $R^6$, and $R^7$ are independently haloalkyl further substituted with 1 or 2 hydroxy.

Embodiment 37

Provided is the Compound of any one of Embodiments 1-30 where $R^5$ is $C_4$-$C_8$-alkyl.

Embodiment 38

Provided is the Compound of any one of Embodiments 1-37 where $R^1$ is substituted with one $R^{1a}$.

Embodiment 39

Provided is the Compound of any one of Embodiments 1-38 where $R^{1a}$, when present, is alkyl.

Embodiment 40

Provided is the Compound of any one of Embodiments 1-39 where $R^{1b}$ is alkyl, alkenyl, haloalkyl, cycloalkyl, cycloalkylalkyl, heterocycloalkyl, or heterocycloalkylalkyl.

Embodiment 41

Provided is the compound of any one of Embodiments 1-40 where $R^{1b}$ is alkyl.

Embodiment 42

Provided is the compound of Embodiment 1 selected from Embodiment B; or a stereoisomer, a mixture of stereoisomers, and/or a pharmaceutically acceptable salt thereof.

Embodiment 43

Provided is a pharmaceutical composition comprising a Compound of any one of Embodiments 1-42 or a stereoisomer, a mixture of stereoisomers, and/or a pharmaceutically acceptable salt thereof; and a pharmaceutically acceptable carrier.

Embodiment 44

Provided is a method of treating a condition, disease, or disorder associated with abnormal activation of the SREBP pathway comprising administering to a patient in need thereof a therapeutically effective amount of the Compound of any one of Embodiments 1-42 a stereoisomer, a mixture of stereoisomers, and/or a pharmaceutically acceptable salt thereof or the composition of Embodiment 43.

Embodiment 45

Provided is the method of embodiment 44 where the condition, disease, or disorder is selected from metabolic syndrome, hypertension, type 2 diabetes, dyslipidemia, obesity, pancreatic B-cell dysfunction, atherosclerosis, a cell proliferative disease, a metabolic disease, hyperlipidemia, a lipoprotein related disease, combined hyperlipidemia (elevated cholesterol and triglycerides), Frederickson Type IIb, familial combined hyperlipidemia (inherited form of combined hyperlipidemia), familial hypertriglyceridemia, Frederickson Type IV, hyperlipoproteinemia Type V, mixed hyperlipidemia, Acquired hyperlipidemia, Fatty Liver Disease, Nonalcoholic Steatohepatitis, Neutral Lipid Storage Diseases, Chanarin-Dorfman Syndrome, Tissue Inflammation such as Cutaneous Psoriasis (associated with Metabolic syndrome), coronary artery disease (atherosclerosis), Post Myocardial Infarction management, Peripheral vascular disease, cerebrovascular disease—thrombotic, Type II Diabetes Mellitus, Diabetic Nephropathy, cancer, Hepatocellular Carcinoma, Glioblastoma Multiforme, Prostate Cancer, Post menopausal Breast Carcinoma, Pancreatic Adenocarcinoma, Ovarian cancer, B cell lymphoma, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach (gastric) cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer; or wherein the patient is in need of increased thermogenesis (for example, without reducing lean body mass during weight loss) or in need of reducing body weight.

Embodiment 46

Provided is the method of Embodiment 44 or 45 where the condition, disease, or disorder is selected from metabolic syndrome, hypertension, type 2 diabetes, dyslipidemia, obesity, pancreatic B-cell dysfunction, atherosclerosis, Hepatocellular Carcinoma, Glioblastoma Multiforme, Prostate Cancer, post-menopausal Breast Carcinoma, Pancreatic Adenocarcinoma, Ovarian cancer, B cell lymphoma, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach (gastric) cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer; or wherein the patient is in need of increased thermogenesis or in need of reducing body weight.

Embodiment B

In some or any embodiments, provided is a Compound according to any of the following formula:

Embodiment B

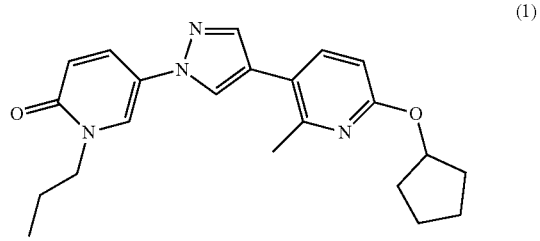

(1)

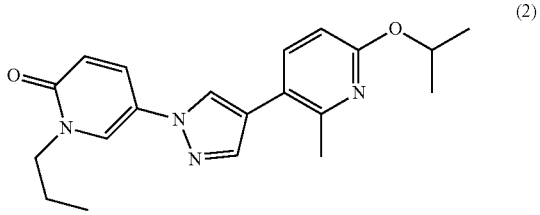

(2)

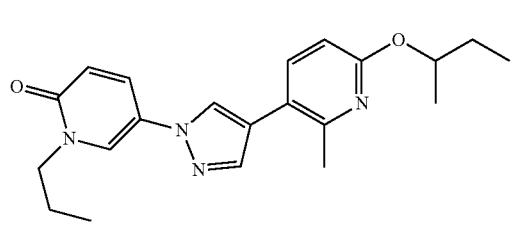
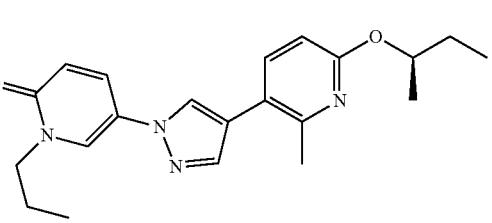
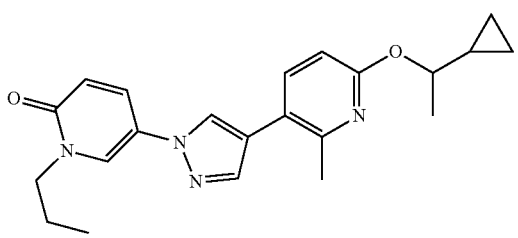
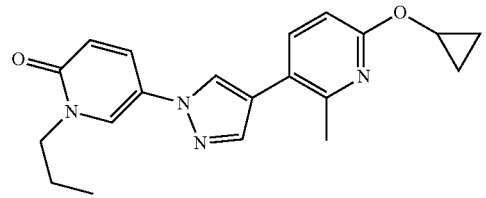
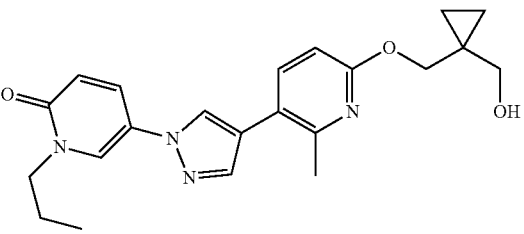
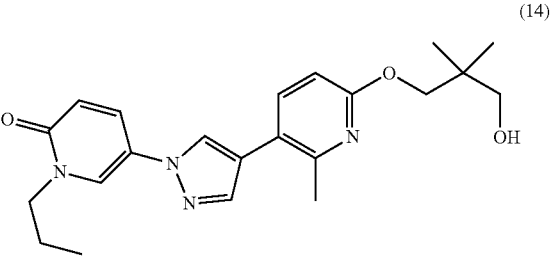
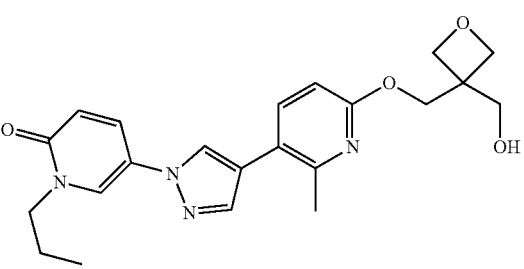

-continued
(16)
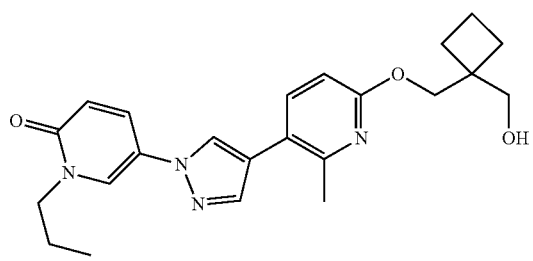
(17)
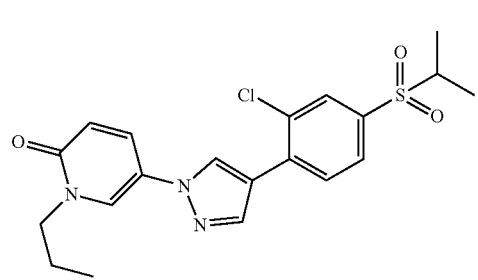
(18)
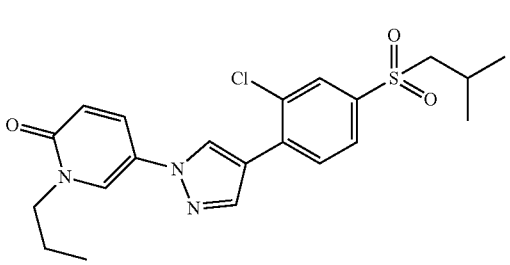
(19)
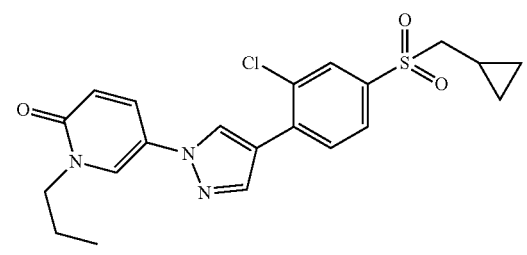
(20)
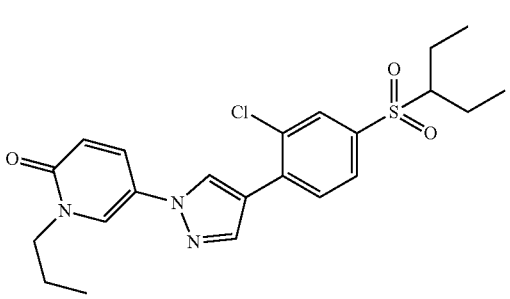
(21)
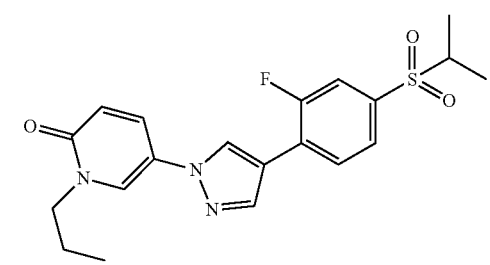
-continued
(22)
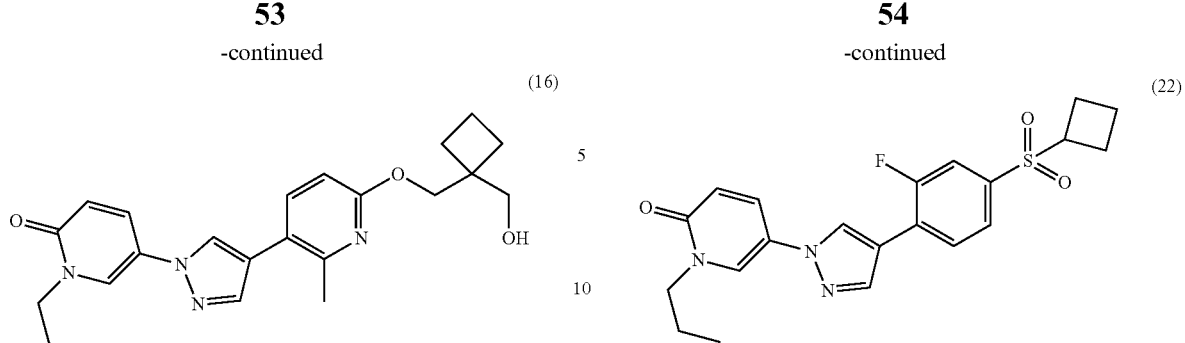
(23)
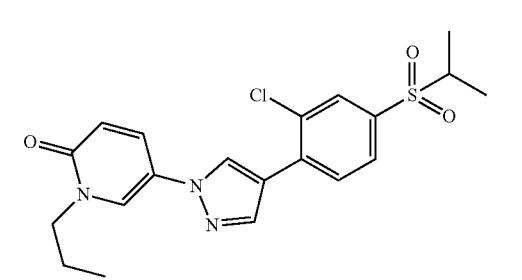
(24)
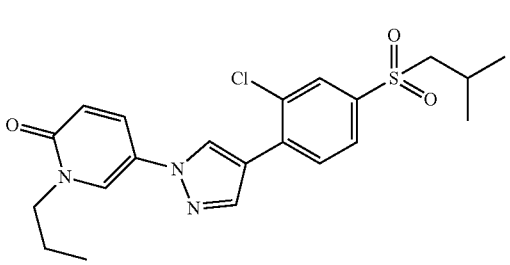
(25)
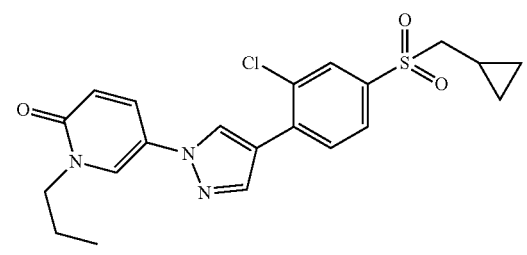
(26)
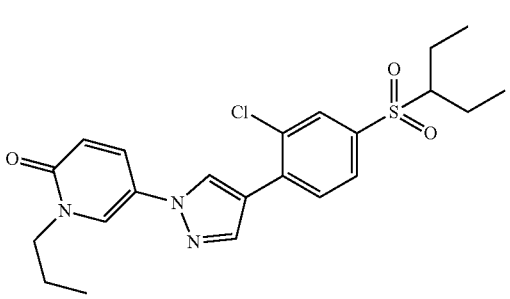
(27)
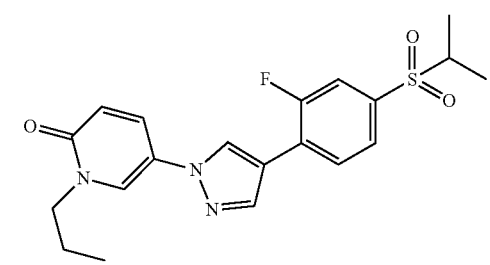

(28)
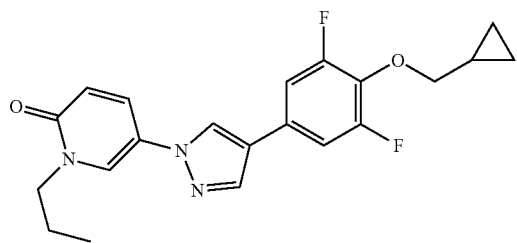
(29)
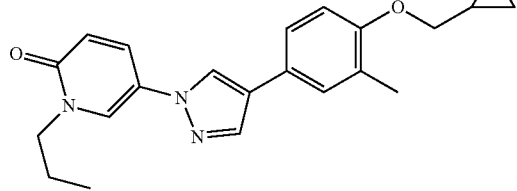
(30)
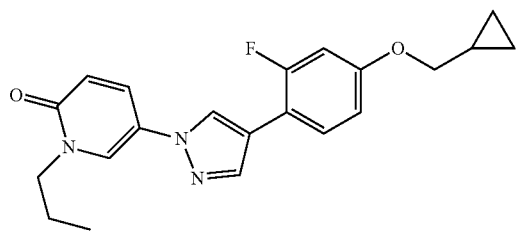
(31)
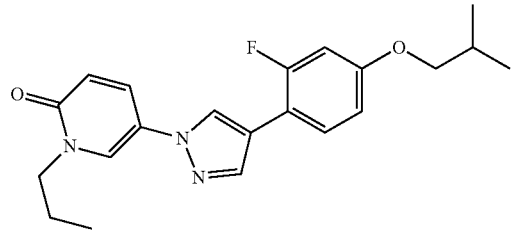
(32)
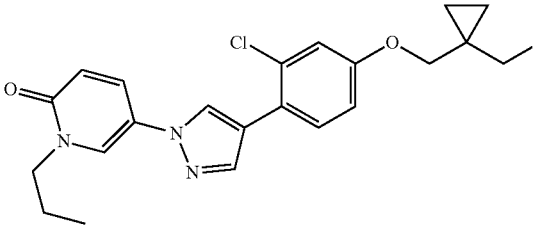
(33)
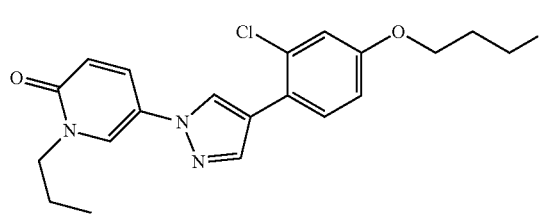
(34)
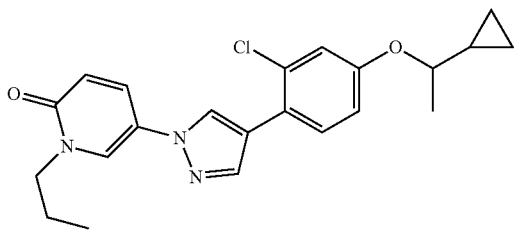
(35)
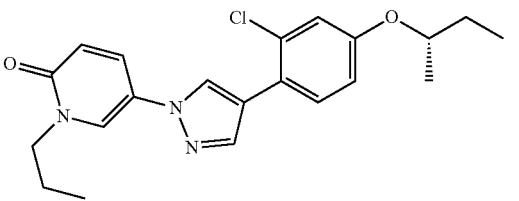
(36)
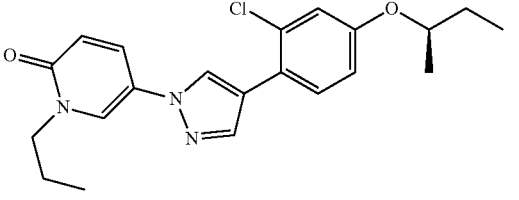
(37)
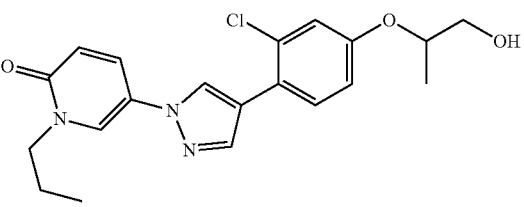
(38)
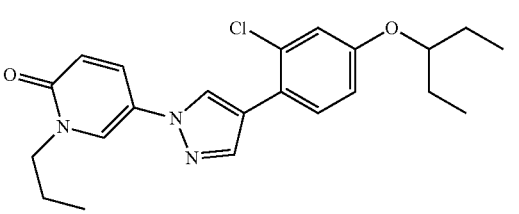
(39)
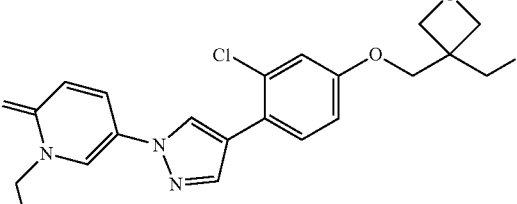
(40)
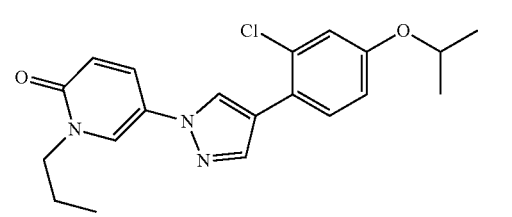

-continued
(41)
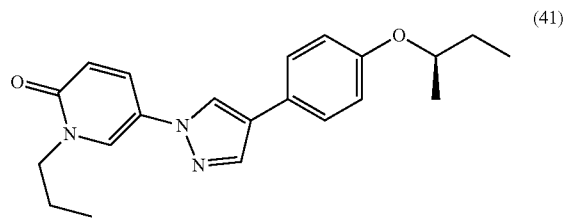
(42)
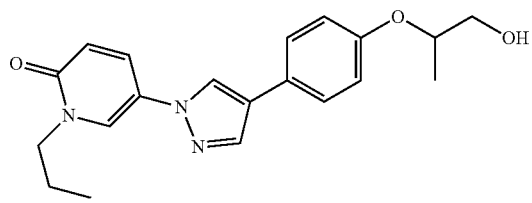
(43)
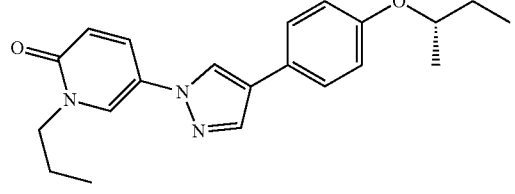
(44)
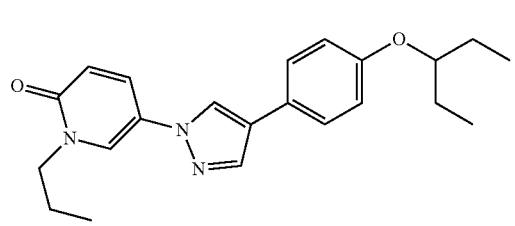
(45)
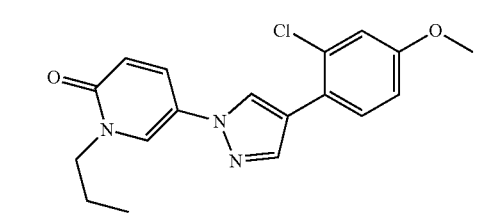
(46)
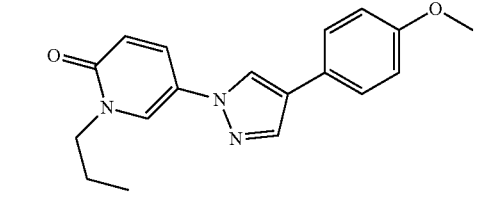
(47)
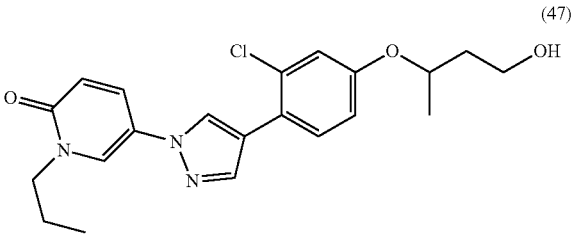
-continued
(48)
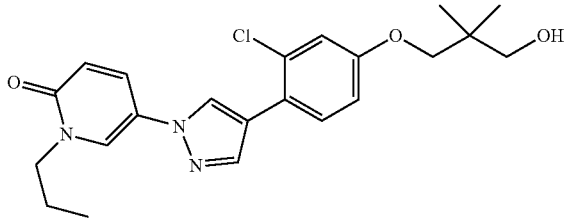
(49)
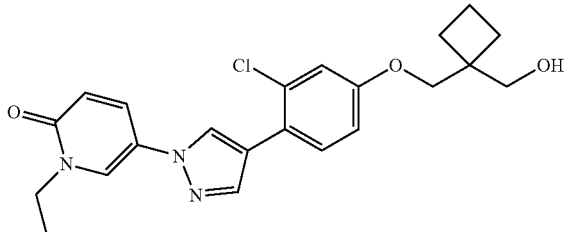
(50)
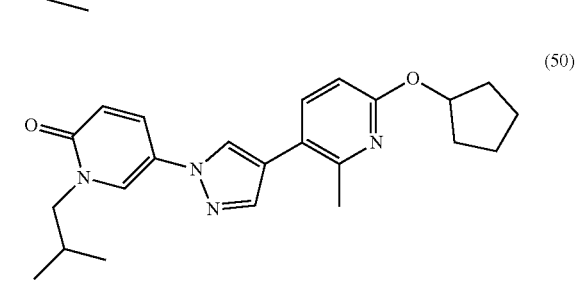
(51)
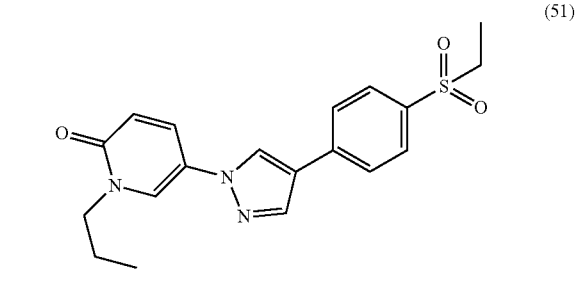
(52)
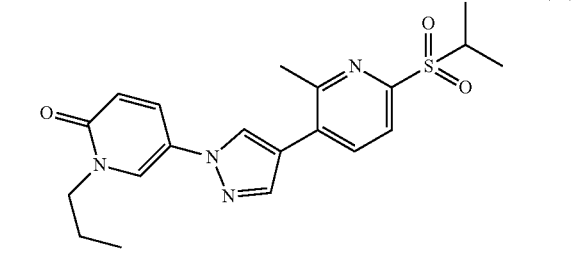
(53)
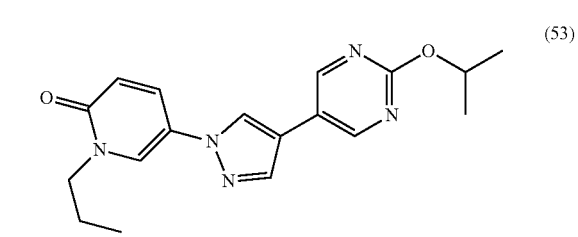

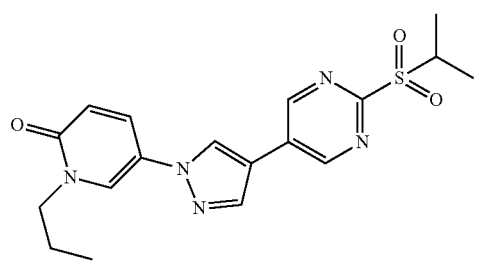
(54)
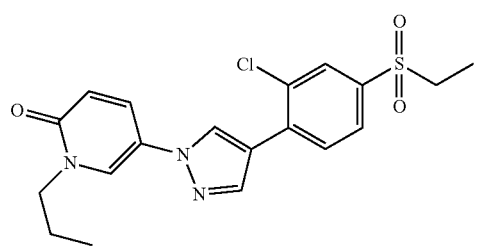
(55)
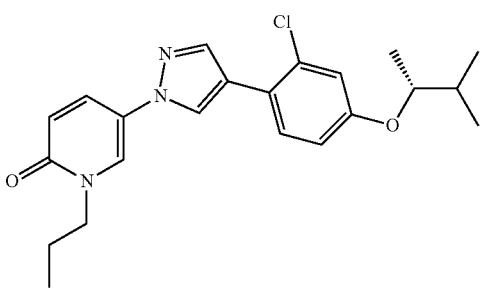
(56)
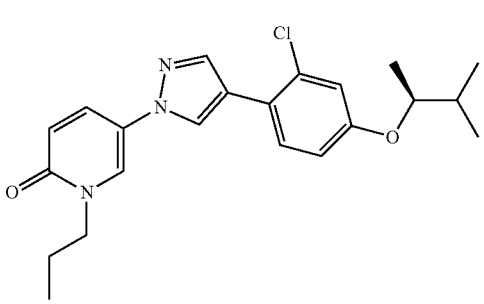
(57)
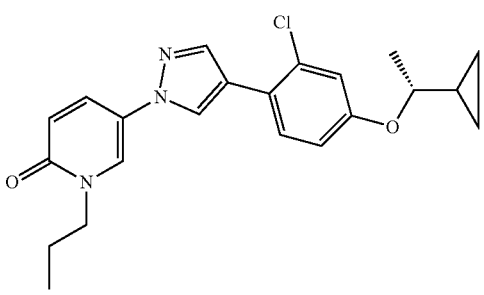
(58)
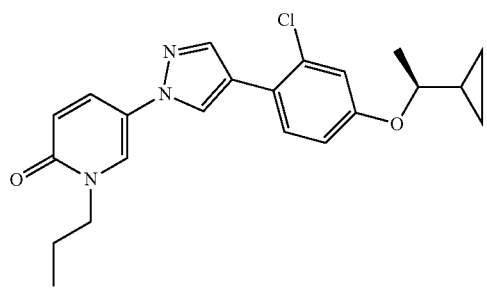
(59)
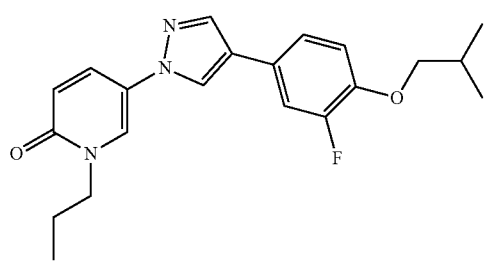
(60)
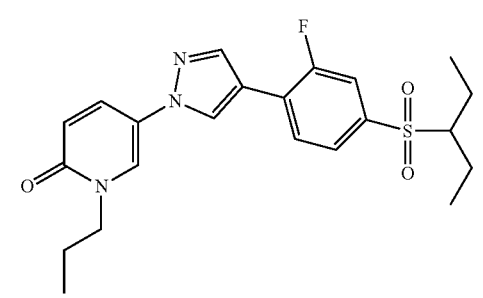
(61)
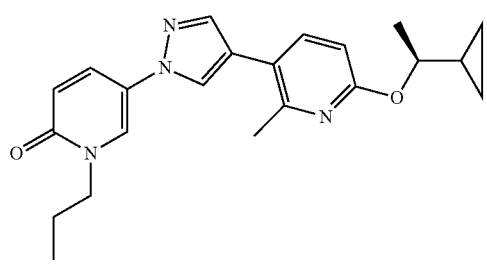
(62)
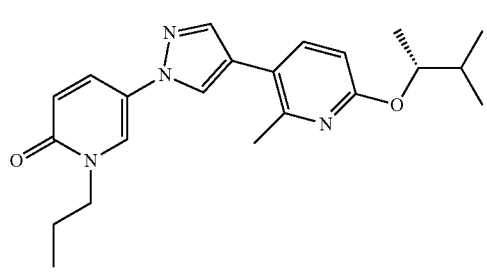
(63)
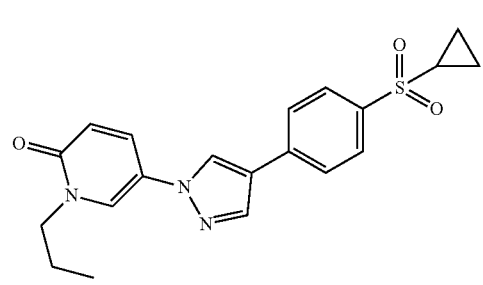
(64)

(65)
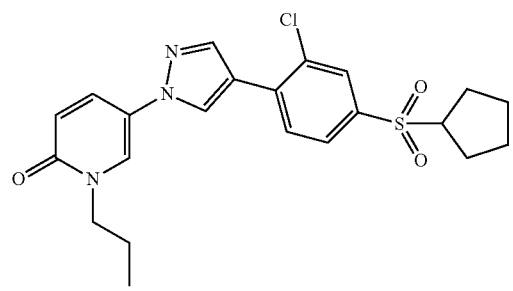
(66)
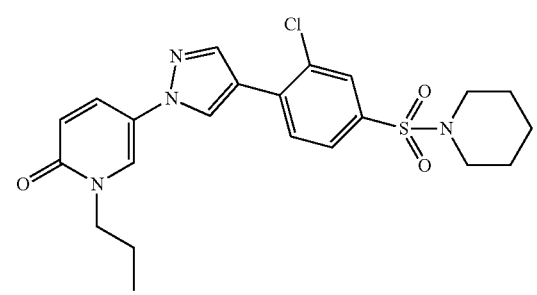
(67)
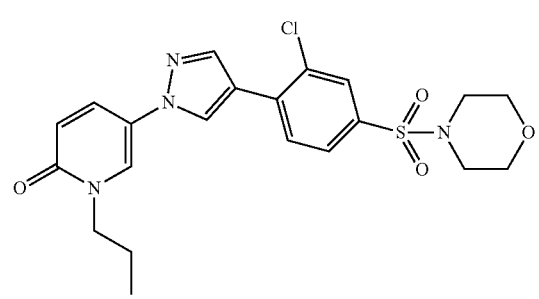
(68)
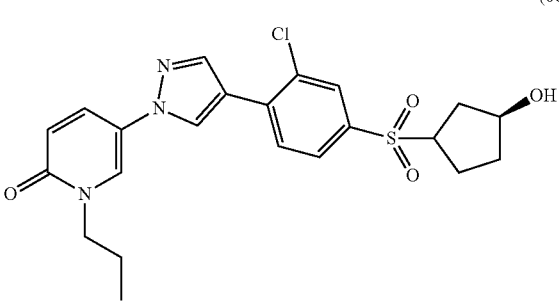
(69)
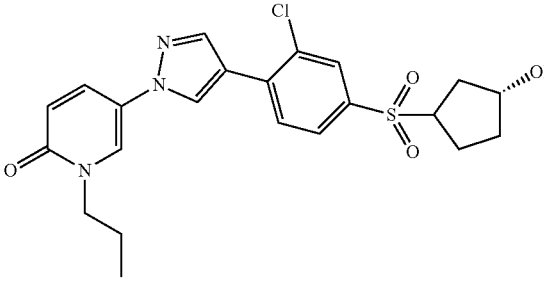
(70)
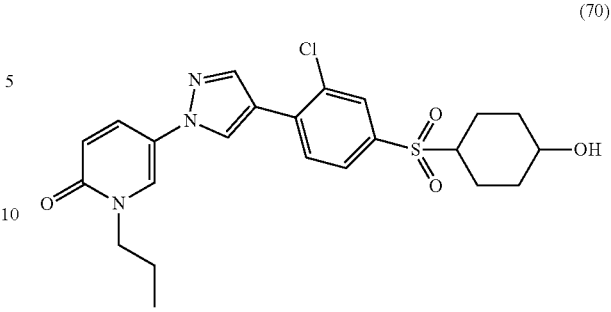
(71)
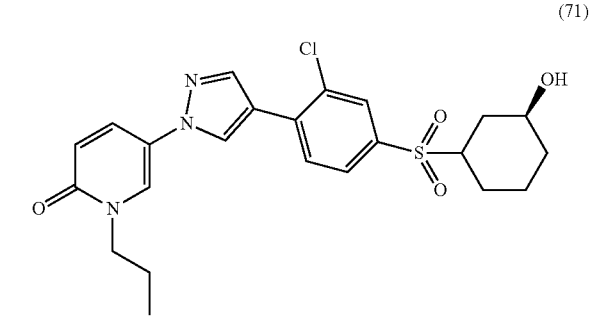
(72)
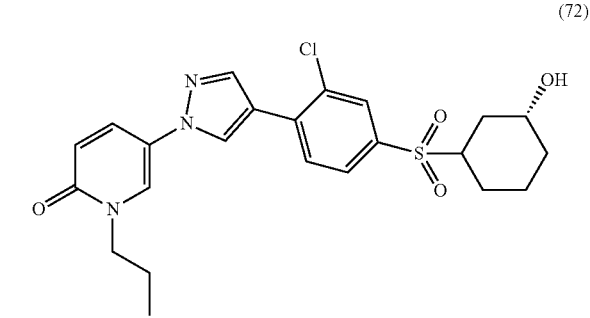
(73)
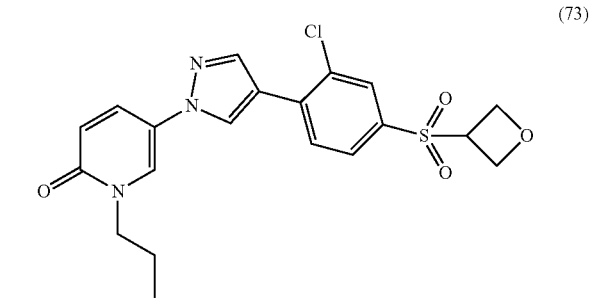
(74)
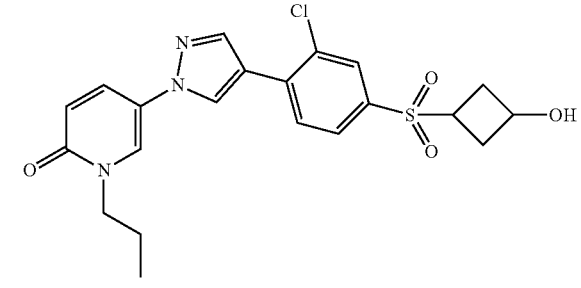

(75) 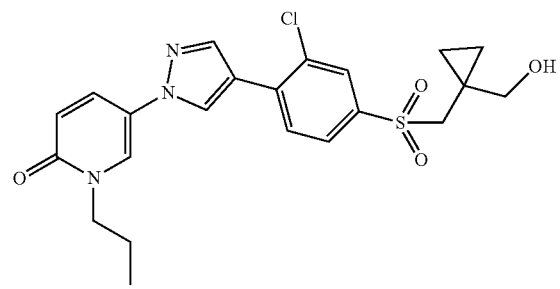
(80) 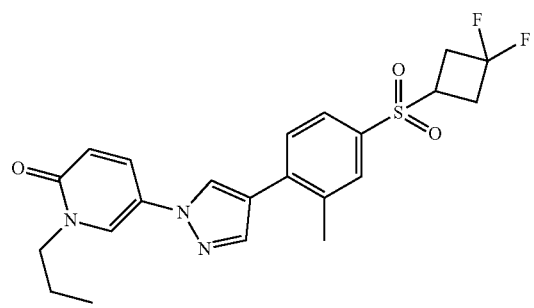
(76) 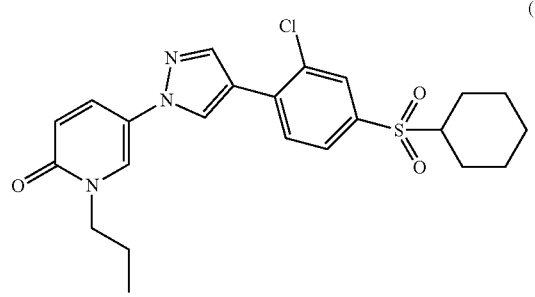
(81) 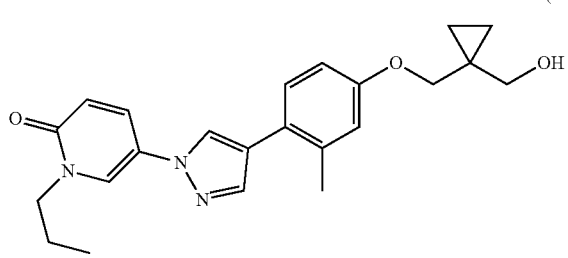
(77) 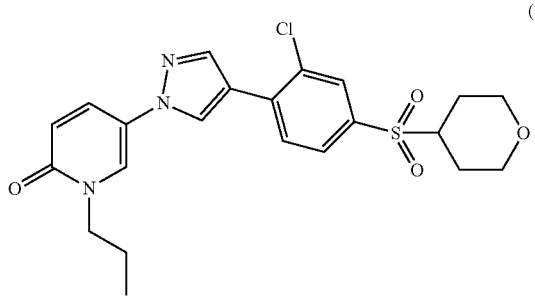
(82) 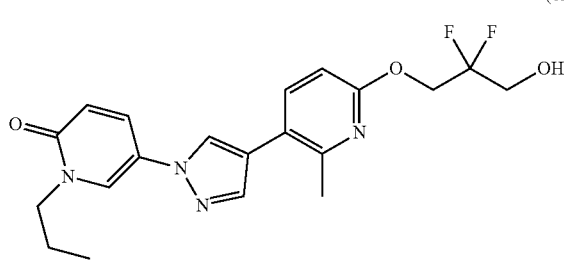
(78) 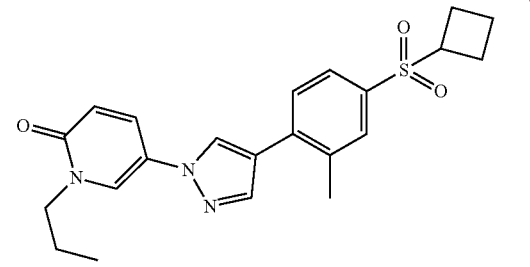
(83) 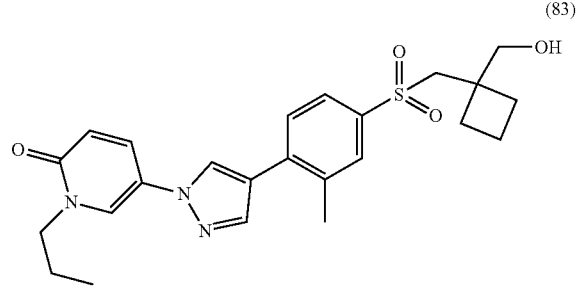
(79) 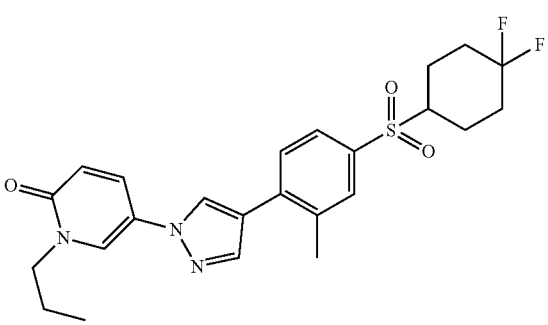
(84) 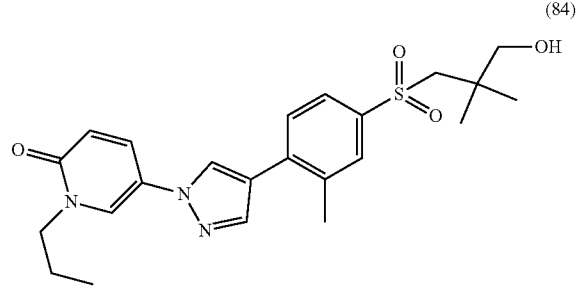

-continued

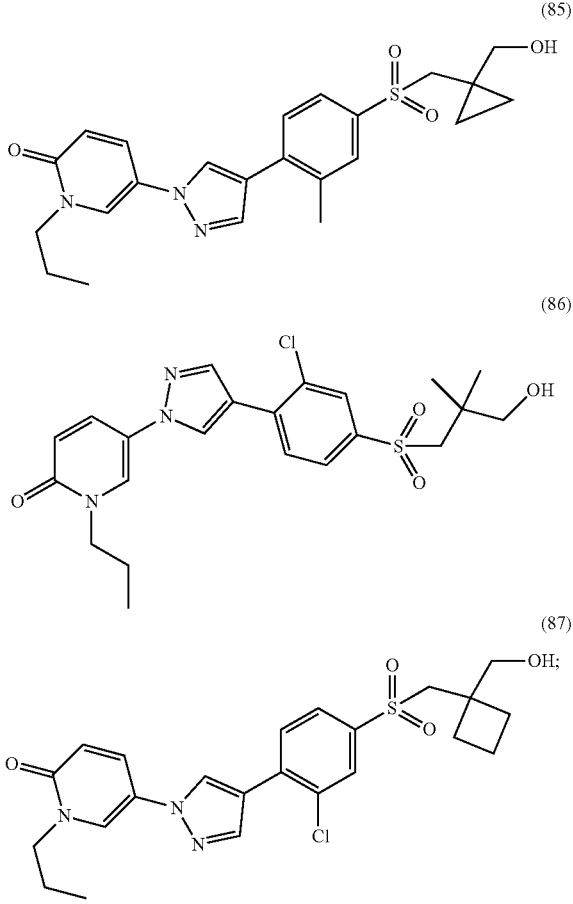

or a stereoisomer, a mixture of stereoisomers, and/or a pharmaceutically acceptable salt thereof.

In some embodiments, provided herein are:
(a) compounds as described herein, e.g., of Formula (I)-(Ij), (Ia-1)-(Ij-1), Embodiment A, and Embodiment B, and pharmaceutically acceptable salts and compositions thereof;
(b) compounds as described herein, e.g., of Formula (I)-(Ij), (Ia-1)-(Ij-1), Embodiment A, and Embodiment B, and pharmaceutically acceptable salts and compositions thereof for use in the treatment of a condition, disease, or disorder associated with abnormal activation of the SREBP pathway;
(c) processes for the preparation of compounds as described herein, e.g., of Formula (I)-(Ij), (Ia-1)-(Ij-1), Embodiment A, and Embodiment B, as described in more detail elsewhere herein;
(d) pharmaceutical formulations comprising a compound as described herein, e.g., of Formula (I)-(Ij), (Ia-1)-(Ij-1), Embodiment A, and Embodiment B, or a stereoisomer, a mixture of stereoisomers, and/or a pharmaceutically acceptable salt thereof together with a pharmaceutically acceptable carrier;
(e) a method for the treatment of a condition, disease, or disorder associated with abnormal activation of the SREBP pathway in a subject that includes the administration of an effective treatment amount of a compound as described herein, e.g., of Formula (I)-(Ij), (Ia-1)-(Ij-1), Embodiment A, and Embodiment B, its pharmaceutically acceptable salt or composition;
(f) pharmaceutical formulations comprising a compound as described herein, e.g., of Formula (I)-(Ij), (Ia-1)-(Ij-1), Embodiment A, and Embodiment B, or a stereoisomer, a mixture of stereoisomers, and/or a pharmaceutically acceptable salt thereof together with one or more other effective agents for treating a condition, disease, or disorder associated with abnormal activation of the SREBP pathway, optionally in a pharmaceutically acceptable carrier; or
(g) a method for the treatment of a condition, disease, or disorder associated with abnormal activation of the SREBP pathway in a subject that includes the administration of an effective treatment amount of a compound as described herein, e.g., of Formula (I)-(Ij), (Ia-1)-(Ij-1), Embodiment A, and Embodiment B, its pharmaceutically acceptable salt or composition in combination and/or alternation with one or more agent for the treatment of a condition, disease, or disorder associated with abnormal activation of the SREBP pathway.

Optically Active Compounds

It is appreciated that compounds provided herein have several chiral centers and may exist in and be isolated in optically active and racemic forms. It is to be understood that any racemic, optically-active, diastereomeric, tautomeric, or stereoisomeric form, or mixtures thereof, of a compound provided herein, which possess the useful properties described herein is within the scope of the invention. It being well known in the art how to prepare optically active forms (in certain embodiments, by resolution of the racemic form by recrystallization techniques, by synthesis from optically-active starting materials, by chiral synthesis, or by chromatographic separation using a chiral stationary phase).

In some or any embodiments, the term "stereoisomers" includes diastereomers, enantiomers, rotamers, atropisomers, and geometric isomers; and mixtures thereof.

In certain embodiments, methods to obtain optically active materials are known in the art, and include at least the following.

i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;

ii) simultaneous crystallization—a technique whereby the individual stereoisomers are separately crystallized from a solution of the racemate, possible only if the latter is a conglomerate in the solid state;

iii) enzymatic resolutions—a technique whereby partial or complete separation of a racemate by virtue of differing rates of reaction for the stereoisomers with an enzyme;

iv) enzymatic asymmetric synthesis—a synthetic technique whereby at least one step of the synthesis uses an enzymatic reaction to obtain an stereoisomerically pure or enriched synthetic precursor of the desired stereoisomer;

v) chemical asymmetric synthesis—a synthetic technique whereby the desired stereoisomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) stereospecific synthesis from non-racemic precursors—a synthetic technique whereby the desired stereoisomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase; xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

Isotopically Enriched Compounds

Also provided herein are isotopically enriched compounds, including but not limited to isotopically enriched di-substituted pyrazoles.

Isotopic enrichment (in certain embodiments, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, in certain embodiments, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. In certain embodiments, such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Pharmaceutical Compositions and Methods of Administration

The compounds provided herein can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of Formula (I)-(Ij) Embodiment A, and Embodiment B, if appropriate in a salt form, either used alone or in the form of a combination with one or more compatible and pharmaceutically acceptable carriers, such as diluents or adjuvants, or with another agent for the treatment of a condition, disease, or disorder associated with abnormal activation of the SREBP pathway.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Any embodiment described for "excipient". Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36-NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899;

3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition, disease, or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intra-arterial. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a condition, disease, or disorder associated with abnormal activation of the SREBP pathway in a subject by administering, to a subject in need thereof, an effective amount of a compound provided herein, or a stereoisomer, a mixture of stereoisomers, and/or a pharmaceutically acceptable salt thereof. The amount of the compound or composition which will be effective in the treatment of a disorder or one or more symptoms thereof will vary with the nature and severity of the condition, disease, or disorder, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the condition, disease, or disorder described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different conditions, diseases, or disorders, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiments, the daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, about 300 mg/kg, about 325 mg/kg, bout 350 mg/kg, about 375 mg/kg, about 400 mg/kg, about 425 mg/kg, about 450 mg/kg, about 475 mg/kg, about 500 mg/kg, or about 600 mg/kg. In certain embodiments, the daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, about 150-250 mg/kg, about 250-300 mg/kg, about 300-350 mg·kg, about 300-400 mg/kg, about 200-400 mg/kg, about 100-300 mg/kg, or about 400-500 mg/kg.

In certain embodiment, the twice daily dosage of the composition provided herein, based on weight of the active compound, administered to prevent, treat, manage, or ameliorate a condition, disorder, disease, or one or more symptoms thereof in a subject is about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, about 225 mg/kg, about 250 mg/kg, about 275 mg/kg, or about 300 mg/kg. In certain embodiments, the twice daily dosage of the composition provided herein, based on weight of the active compound, administered to prevent, treat, manage, or ameliorate a condition, disorder, disease, or one or more symptoms thereof in a subject is between (inclusive) about 1-10 mg/kg, about 10 mg/kg, about 25-50 mg/kg, about 50-100 mg/kg, about 50-150 mg/kg, about 100-150 mg/kg, about 100-200 mg/kg, about 150-200 mg/kg, or about 150-250 mg/kg In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a stereoisomer, a mixture of stereoisomers, and/or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In certain embodiments, dosages of the second agents to be used in a combination therapy are provided herein. In certain embodiments, dosages lower than those which have been or are currently being used to treat a condition, disease, or disorder associated with abnormal activation of the SREBP pathway are used in the combination therapies provided herein. The recommended dosages of second agents can be obtained from the knowledge of those of skill in the art. For those second agents that are approved for clinical use, recommended dosages are described in, for example, Hardman et al., eds., 1996, Goodman & Gilman's The Pharmacological Basis Of Therapeutics $9^{th}$ Ed, Mc-Graw-Hill, New York; Physician's Desk Reference (PDR) $57^{th}$ Ed., 2003, Medical Economics Co., Inc., Montvale, N.J.; which are incorporated herein by reference in their entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, in certain embodiments, a mammal, such as a human, in a sequence and within a time interval such that the compound provided herein can act together with the other agent to provide an increased benefit than if they were administered otherwise. In certain embodiments, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agent) for a period of time, followed by the administration of a second agent and/or third agent (e.g., a second and/or third prophylactic or therapeutic agent) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. In certain embodiments, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a condition, disease, or disorder associated with abnormal activation of the SREBP pathway. The kits can include a compound or composition provided herein, a second agent or composition, and instructions providing information to a health care provider regarding usage for treating a condition, disease, or disorder associated with abnormal activation of the SREBP pathway. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for treating a condition, disease, or disorder associated with abnormal activation of the SREBP pathway in a subject, which comprises contacting the subject with a therapeutically effective amount of a compound disclosed herein, e.g., a compound of Formula (I)-(Ij), (Ia-1)-(Ij-1), Embodiment A, and Embodiment B, including a single enantiomer, a mixture of an enantiomeric pair, an individual diastereomer, a mixture of diastereomers, an individual stereoisomer, a mixture of stereoisomers, an individual geometric isomer, a mixture of geometric isomers, or a tautomeric form thereof or a pharmaceutically acceptable salt, solvate, prodrug, phosphate, or active metabolite thereof.

In certain embodiments, provided herein are methods for treating a condition, disease, or disorder associated with abnormal activation of the SREBP pathway in a subject. In certain embodiments, the methods encompass the step of administering to the subject in need thereof an amount of a compound effective for the treatment of a condition, disease, or disorder associated with abnormal activation of the SREBP pathway in combination with a second agent. The compound can be any compound as described herein, and the second agent can be any second agent described in the art or herein. In certain embodiments, the compound is in the form of a pharmaceutical composition or dosage form, as described elsewhere herein.

Diseases which can be treated with the Compound according to any of the Formula described herein, including Compounds in Embodiments A and B, include metabolic syndrome, hypertension, type 2 diabetes, dyslipidemia, obesity, pancreatic B-cell dysfunction, atherosclerosis, cell proliferative disease, reducing body weight, increasing thermogenesis (for example, without reducing lean body mass during weight loss), metabolic diseases, hyperlipidemia, a lipoprotein related disease, combined hyperlipidemia (elevated cholesterol and triglycerides), Frederickson Type IIb, familial combined hyperlipidemia (inherited form of combined hyperlipidemia), familial hypertriglyceridemia, Frederickson Type IV, hyperlipoproteinemia Type V, mixed hyperlipidemia, Acquired hyperlipidemia, Fatty Liver Disease, Nonalcoholic Steatohepatitis, Neutral Lipid Storage Diseases, Chanarin-Dorfman Syndrome, Tissue Inflammation such as Cutaneous Psoriasis (associated with Metabolic syndrome), coronary artery disease (atherosclerosis), post myocardial infarction management, peripheral vascular disease, cerebrovascular disease—thrombotic, type II diabetes mellitus, diabetic nephropathy, cancer, hepatocellular carcinoma—not amenable to surgical or locoregional therapy, glioblastoma multiforme, prostate cancer, breast cancer, post-menopausal breast carcinoma, pancreatic adenocarcinoma, ovarian cancer, and B cell lymphoma.

Diseases which can be treated with the Compound according to any of the Formula described herein, including Compounds in Embodiments A and B, include hyperlipidemia, a lipoprotein related disease, combined hyperlipidemia (elevated cholesterol and triglycerides), Frederickson Type IIb, familial combined hyperlipidemia (inherited form of combined hyperlipidemia), familial hypertriglyceridemia, Frederickson Type IV, hyperlipoproteinemia Type V, mixed hyperlipidemia, Acquired hyperlipidemia, Fatty Liver Disease, Nonalcoholic Steatohepatitis, Neutral Lipid Storage Diseases, Chanarin-Dorfman Syndrome, Tissue Inflammation such as Cutaneous Psoriasis (associated with Metabolic syndrome), coronary artery disease (atherosclerosis), post myocardial infarction management, peripheral vascular disease, cerebrovascular disease—thrombotic, type II diabetes mellitus, diabetic nephropathy, cancer, hepatocellular carcinoma—not amenable to surgical or locoregional therapy, glioblastoma multiforme, prostate cancer, breast cancer, post-menopausal breast carcinoma, pancreatic adenocarcinoma, ovarian cancer, and B cell lymphoma.

Additional cancers which can be treated with the Compound according to any of the Formula described herein, including Compounds in Embodiments A and B, include a cancer selected from the group consisting of lung cancer, a digestive and gastrointestinal cancer, gastrointestinal stromal tumor, gastrointestinal carcinoid tumor, colon cancer, rectal cancer, anal cancer, bile duct cancer, small intestine cancer, stomach (gastric) cancer, esophageal cancer, gall bladder cancer, liver cancer, pancreatic cancer, appendix cancer, breast cancer, ovarian cancer, renal cancer, cancer of the central nervous system, skin cancer, a lymphoma, choriocarcinoma, head and neck cancer, osteogenic sarcoma, and a blood cancer.

Assay Methods

Compounds can be assayed for efficacy in treating a condition, disease, or disorder associated with abnormal activation of the SREBP pathway according to any assay known to those of skill in the art. Exemplary assay methods are provided elsewhere herein.

Second Therapeutic Agents

In certain embodiments, the compounds and compositions provided herein are useful in methods of treatment of a condition, disease, or disorder associated with abnormal activation of the SREBP pathway, that comprise further administration of a second agent. The second agent can be any agent known to those of skill in the art to be effective for the treatment of a condition, disease, or disorder associated with abnormal activation of the SREBP pathway, including those currently approved by the United States Food and Drug Administration, or other similar body of a country foreign to the United States.

In some embodiments, the disease is cancer and the second agent is a cancer treatment. In some embodiments, the disease is cancer and the second agent is a chemotherapeutic agent. In some embodiments, the chemotherapeutic agent is selected from an alkylating agent (e.g. cyclophosphamide, mechlorethamine, chlorambucil, melphalan, dacarbazine (DTIC), a nitrosoureas, temozolomide (oral dacarbazine); an anthracycline (e.g. daunorubicin, doxorubicin, liposomal doxorubicin, epirubicin, idarubicin, mitoxantrone, and valrubicin); a cytoskeletal disruptor (a taxane, e.g. paclitaxel, Albumin-bound paclitaxel and docetaxel); epothilone; an Histone Deacetylase inhibitor (e.g. vorinostat and romidepsin); an inhibitor of Topoisomerase I (e.g. irinotecan and topotecan); an inhibitor of Topoisomerase II (e.g. etoposide, teniposide, and tafluposide); a kinase inhibitor (e.g. sorafenib, cobimetinib, cabozantanib, lapatinib, bortezomib, erlotinib, gefitinib, imatinib, vemurafenib, and vismodegib); a nucleotide analog and precursor analog (e.g. azacitidine, azathioprine, capecitabine, cytarabine, doxifluridine, fluorouracil, gemcitabine, hydroxyurea, mercaptopurine, methotrexate, and tioguanine); a peptide antibiotic (e.g. bleomycin and actinomycin); a platinum agent (e.g. carboplatin, cisplatin, and oxaliplatin); a retinoid (e.g. tretinoin, alitretinoin, and bexarotene); a vinca alkaloid or derivative (e.g. Capecitabine, vinblastine, vincristine, vindesine, and vinorelbine); eribulin; ixabepilone; radiation; bevacizumab; olaparib; an aromatase inhibitor (e.g. letrozole, anastrozole, and exemestane); rituximab; ibritumomab; prednisone; and enzalutamide.

In some embodiments, the disease is cancer and the second agent is a kinase inhibitor e.g. sorafenib, cobimetinib, cabozantanib, lapatinib, bortezomib, erlotinib, gefitinib, imatinib, vemurafenib, and vismodegib. In some embodiments, the disease is cancer and the second agent is a kinase inhibitor such as sorafenib or erlotinib.

In some embodiments, the disease is breast cancer (e.g. pos-menopausal breast carcinoma) and the second agent is radiation, docetaxel, paclitaxel, platinum agents (cisplatin, carboplatin), vinorelbine, capecitabine, liposomal doxorubicin, gemcitabine, mitoxantrone, ixabepilone, albumin-bound paclitaxel, eribulin, trastuzumab, pertuzimab, ado-trastuzumab, lapatinib, bevacizumab, olaparib, radiation, an aromatase inhibitor (e.g. letrozole, anastrozole, and exemestane), or tamoxifen.

In some embodiments, the disease is liver cancer (e.g. hepatocellular carcinoma, hepatocellular carcinoma not amenable to surgical or locoregional therapy) and the second agent is sorafenib.

In some embodiments, the disease is prostate cancer and the second agent is radiation, abiraterone, or enzalutamide.

In some embodiments, the disease is pancreatic adenocarcinoma and the second agent is radiation.

In some embodiments, the disease is ovarian cancer and the second agent is bevacizumab, olaparib, radiation, an aromatase inhibitor (e.g. letrozole, anastrozole, and exemestane), or tamoxifen.

In some embodiments, the disease is B cell lymphoma and the second agent is rituximab, radiation, ibritumomab, cyclophosphamide, doxorubicin, vincristine, or prednisone.

In certain embodiments, a compound provided herein is administered in combination with one second agent. In further embodiments, a compound provided herein is administered in combination with two second agents. In still further embodiments, a compound provided herein is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an agent effective in the treatment of a condition, disease, or disorder associated with abnormal activation of the SREBP pathway. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition, disease, or disorder associated with abnormal activation of the SREBP pathway to be treated. It is to be further understood that for any particular subject, specific dosage regimens and schedules should be adjusted over time according to the individual need and the professional judgment of the person administering or supervising the administration of the compositions.

Preparation of Compounds

The compounds provided herein can be prepared, isolated or obtained by any method apparent to those of skill in the art. Compounds provided herein can be prepared according to the Exemplary Preparation Schemes provided below. Reaction conditions, steps, and reactants not provided in the Exemplary Preparation Schemes would be apparent to, and known by, those skilled in the art.

Additional steps and reagents not provided in the Exemplary Preparation Schemes would be known to those of skill in the art. Exemplary methods of preparation are described in detail in the Examples herein.

General Scheme 1

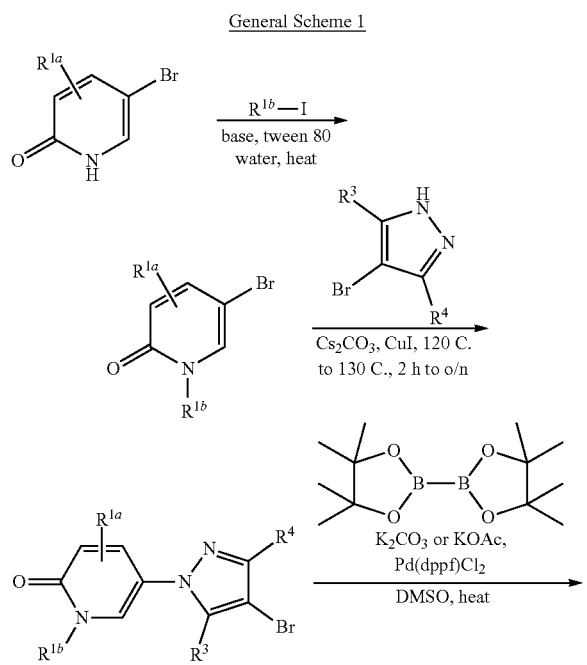

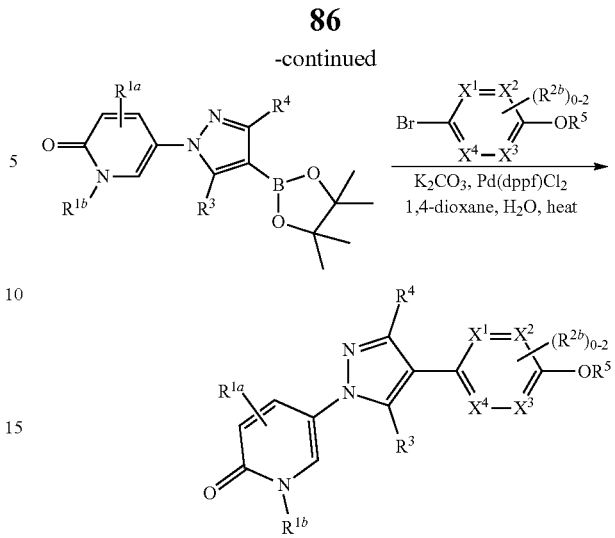

General Scheme 1 describes the preparation of a Compound of Formula (I) where $R^{2a}$ is —$OR^5$; and all other groups are as defined in the Summary of the invention or in any embodiments described herein.

General Scheme 2

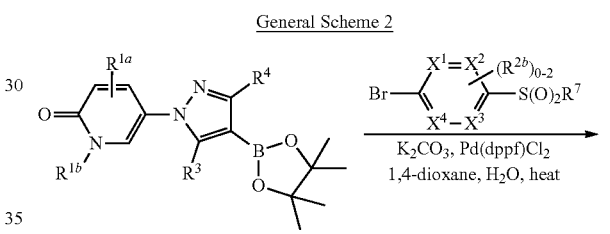

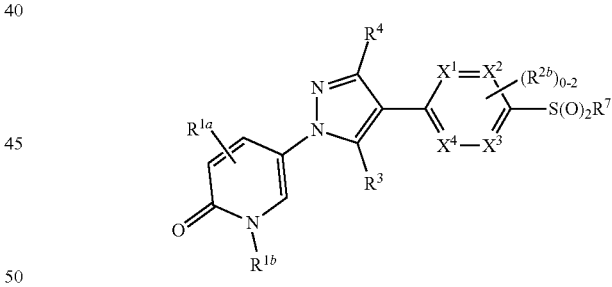

General Scheme 2 describes the preparation of a Compound of Formula (I) where $R^{2a}$ is —$S(O)_2R^7$; and all other groups are as defined in the Summary of the invention or in any embodiments described herein.

General Scheme 3

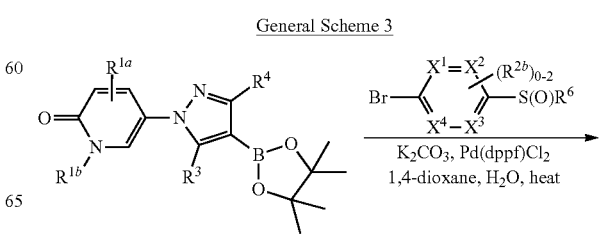

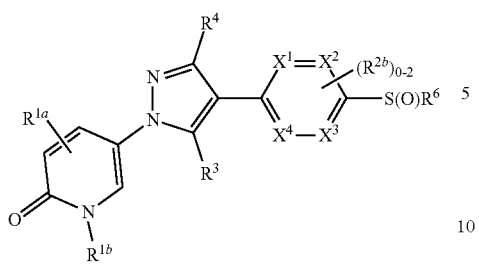

General Scheme 3 describes the preparation of a Compound of Formula (I) where $R^{2a}$ is —S(O)$R^6$; and all other groups are as defined in the Summary of the invention or in any embodiments described herein.

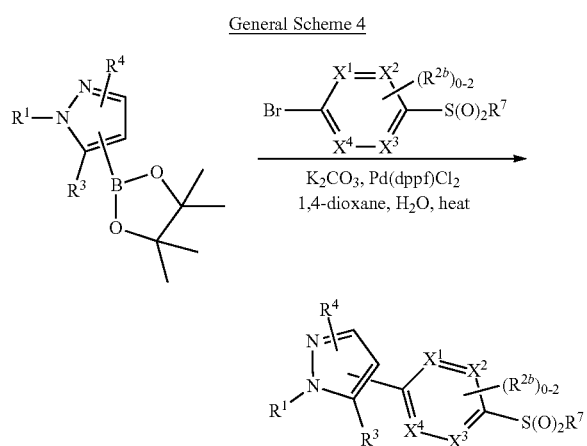

General Scheme 4 describes the preparation of a Compound of Formula (I) where $R^{2a}$ is —S(O)$_2R^7$; and all other groups are as defined in the Summary of the invention or in any embodiments described herein.

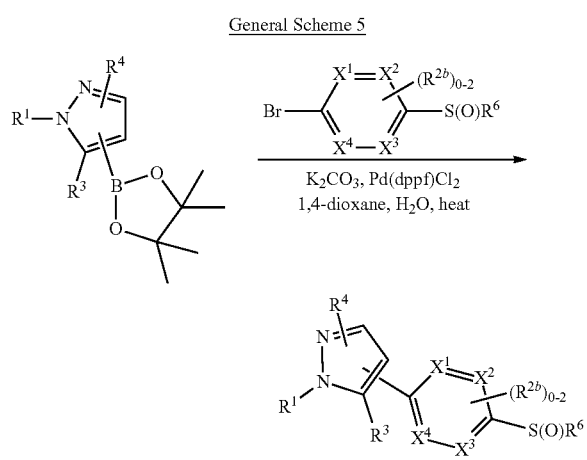

General Scheme 5 describes the preparation of a Compound of Formula (I) where $R^{2a}$ is —S(O)RE; and all other groups are as defined in the Summary of the invention or in any embodiments described herein.

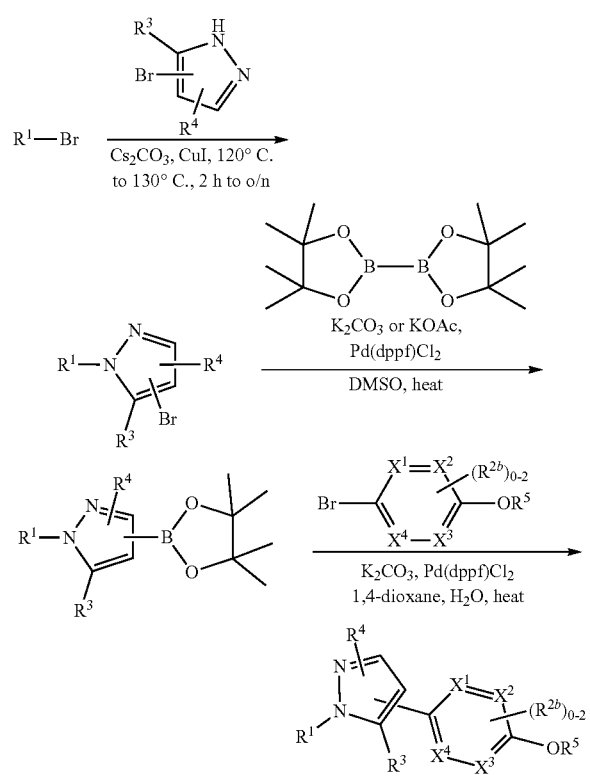

General Scheme 6 describes the preparation of a Compound of Formula (I) where $R^{2a}$ is –O$R^5$; and all other groups are as defined in the Summary of the invention or in any embodiments described herein.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); HPLC (high pressure liquid chromatography); CDCl$_3$ (deuterated chloroform); DMA (dimethylacetamide); DMF (dimethyl formamide); DCM (dichloromethane); DMSO (dimethylsulfoxide); DMSO-d$_6$ (deuterated dimethylsulfoxide); dppf (1,1'-bis(diphenylphosphino)ferrocene); and EtOAc or EA (ethyl acetate).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Intermediates of formula (a):

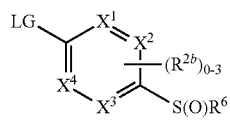

where LG is a leaving group, such as halo (bromo), and where all other groups are as defined in any aspect or embodiment described herein, can be prepared using the procedures described for Intermediate A below, where the intermediate of formula (a) is made and/or isolated before complete oxidation (e.g. with m-CPBA) of —S(O)— to —S(O)$_2$— is achieved.

Intermediate A:
1-Bromo-2-chloro-4-(ethylsulfonyl)benzene was Prepared According to the Following Scheme

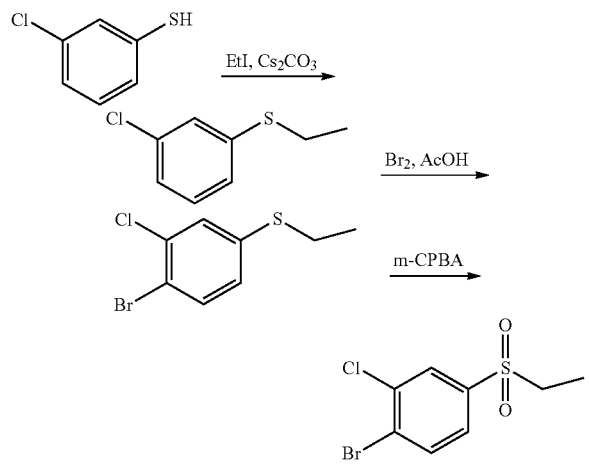

Step 1: (3-chlorophenyl)(ethyl)sulfane

A microwave vial was charged with 3-chlorothiophenol (1.130 g, 7.8 mmol), potassium carbonate (3.240 g, 23.4 mmol), DMF (15 mL) and iodoethane (0.63 mL, 7.8 mmol) and the reaction stirred at room temperature overnight. The reaction mixture was quenched with water and extracted with ethyl acetate (3×50 mL). The solvents were evaporated to dryness and the residue used in the next reaction without purification (1.4 g, 100%).

Step 2: (4-bromo-3-chlorophenyl)(ethyl)sulfane

A round bottom flask was charged with (3-chlorophenyl)(ethyl)sulfane (1.400 g, 8.1 mmol, 1.0 equiv.), acetic acid (10.000 mL, 174.8 mmol) and bromine (0.418 mL, 8.1 mmol) was added at 0° C. The mixture was then allowed to warm to room temperature and stirred overnight. The reaction mixture was poured into ethyl acetate and washed with water twice. The organic layer was washed with brine and dried over MgSO$_4$. The solvents were evaporated to dryness and the residue was purified by flash chromatography (40 g silica, 0-50% ethyl acetate in hexanes, the compound eluted at 5% ethyl acetate) to give the product as colorless liquid (0.87 g, 42%). $^1$H NMR (300 MHz, CDCl$_3$): δ 7.48 (d, J=8.1 Hz, 1H), 7.37 (d, J=2.7 Hz, 1H), 7.04 (dd, J=9.9 and 2.4 Hz, 1H), 2.94 (q, J=7.5 Hz, 2H), 1.32 (t, J=6.6 Hz, 3H).

Step 3: 1-bromo-2-chloro-4-(ethyl sulfonyl)benzene

To a solution of (4-bromo-3-chlorophenyl)(ethyl)sulfane (0.870 g, 3.5 mmol) in DCM (8 mL) was added 70.0% m-chloroperoxybenzoic acid (2.131 g, 8.6 mmol). The reaction mixture was stirred at room temperature overnight. The solid was filtered off, and the filtrate was concentrated to afford product as a white solid, which was used without further purification (1.2 g, 87%). $^1$H NMR (300 MHz, CDCl$_3$): δ 7.98 (d, J=2.1 Hz, 1H), 7.84 (d, J=8.5 Hz, 1H), 7.64 (dd, J=8.5, 2.1 Hz, 1H), 3.14 (q, J=7.5 Hz, 2H), 1.31 (t, J=7.5 Hz, 3H).

The intermediates listed below were prepared according to the general procedures described above for Intermediate A, using starting materials which are commercially-available or readily-available using procedures known to one of ordinary skill in the art.

| Intermediate | $^1$H NMR (CDCl$_3$, 300 MHz) |
|---|---|
| ![A1 structure] (A1) | δ 7.98 (d, J = 2.1 Hz, 1H), 7.87 (d, 7 = 8.5 Hz, 1H), 7.64 (dd, J = 8.5, 2.1 Hz, 1H), 3.26-3.17 (m, 1H), 1.33 (d, J = 6.3 Hz, 6H). |
| ![A2 structure] (A2) | δ 7.99 (d, J = 1.8 Hz, 1H), 7.84 (d, J = 8.1 Hz, 1H), 7.65 (dd, J = 8.5, 2.1 Hz, 1H), 3.00 (d, J = 6.3 Hz, 2H), 2.31-2.22 (m, 1H), 1.00 (d, J = 7.2 Hz, 6H). |

| Intermediate | ¹H NMR (CDCl₃, 300 MHz) |
|---|---|
| 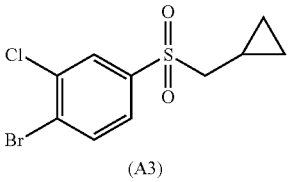 (A3) | δ 8.02 (d, J = 1.8 Hz, 1H), 7.84 (d, J = 8.1 Hz, 1H), 7.65 (dd, J = 8.5, 2.1 Hz, 1H), 3.05 (d, J = 6.9 Hz, 2H), 1.019 (bs, 1H), 0.64-0.60 (m, 2H), 0.20-0.16 (m, 2H). |
| 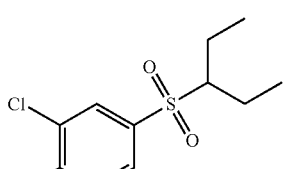 (A4) | δ 7.98-7.80 (m, 2H), 7.59 (bs, 1H), 2.81 (m, 1H), 1.83-1.70 (m, 4H), 1.02 (t, J = 7.4 Hz, 6H). |
| 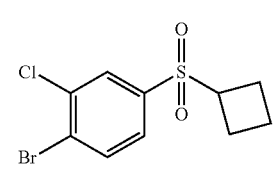 (A5) | δ 7.95-7.59 (m, 3H), 3.84-3.79 (m, 1H), 2.61-2.54 (m, 2H), 2.25-2.20 (m, 2H), 2.08-2.00 (m, 2H). |
| 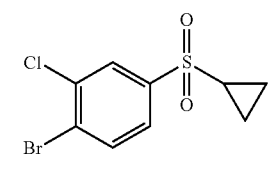 (A6) | δ 7.60 (d, J = 9.0 Hz, 1H), 6.48 (d, J = 8.7 Hz, 1H), 4.08 (d, J = 7.5 Hz, 2H), 2.52 (s, 3H), 1.26 (m, 1H), 0.62-0.58 (m, 2H), 0.36-0.33 (m, 2H). |
| 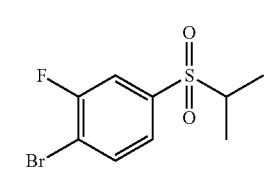 (A7) | δ 7.98-7.80 (m, 2H), 7.53-7.4 (m, 1H), 3.92-3.85 (m, 1H), 1.33 (d, J = 7.4 Hz, 6H). |
| 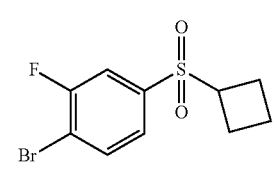 (A8) | δ 7.79-7.52 (m, 3H), 3.85-3.74 (m, 1H), 2.63-2.50 (m, 2H), 2.28-1.95 (m, 4H). |
| 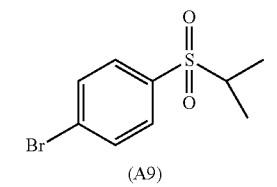 (A9) | δ 7.73-7.72 (m, 4H), 3.19-3.12 (m, 1H), 1.29 (d, J = 7.2 Hz, 6H). |
| 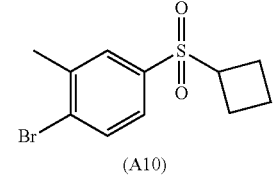 (A10) | δ 7.73 (s, 1H), 7.71 (s, 1H), 7.53 (d, J = 2.1, 1H), 3.82-3.77 (m, 1H), 2.60-2.53 (m, 2H), 2.48 (s, 3H), 2.22-2.18 (m, 2H), 2.05-1.97 (m, 2H). |

| Intermediate | $^1$H NMR (CDCl$_3$, 300 MHz) |
|---|---|
| (A11) | δ 7.59-7.41 (m, 3H), 3.00-2.92 (m, 1H), 2.51 (s, 3H), 2.27-1.63 (m, 8H). |
| (A12) | δ 7.72-7.54 (m, 3H), 3.67-3.55 (m, 1H), 3.20-2.73 (m, 4H), 2.51 (s, 3H). |

Intermediate A13: (1-(((4-bromo-3-chlorophenyl)sulfonyl)methyl)cyclobutyl)methanol was Prepared According to the Following Scheme

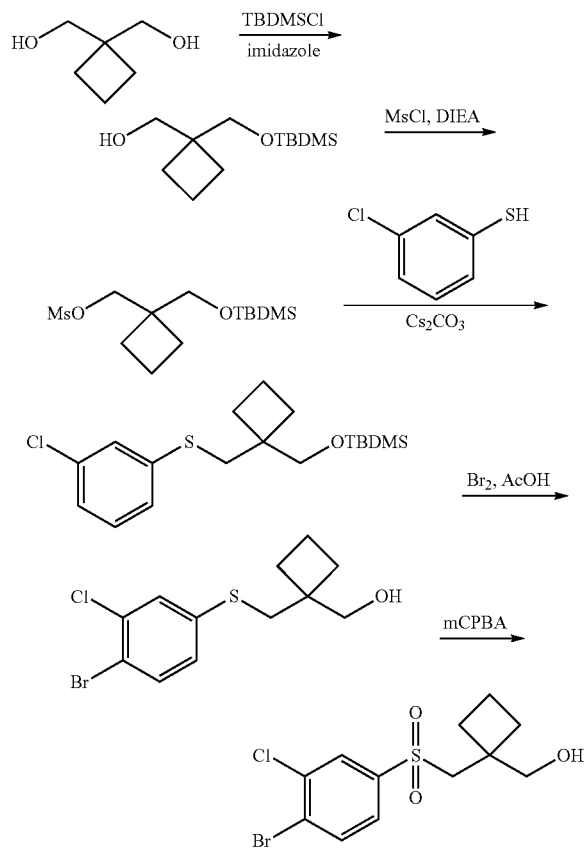

Step 1: (1-(((tert-butyldimethylsilyl)oxy)methyl)cyclobutyl)methanol

To a solution of cyclobutane-1,1-diyldimethanol (10.00 g, 86.1 mmol) in N,N-dimethylformamide (200 mL), imidazole (8.8 g, 129.1 mmol) and tert-butyldimethylsilyl chloride (12.98 g, 86.1 mmol) were added in one portion at 0° C. The reaction mixture was stirred at 0° C. for 10 minutes and then warmed to room temperature for 4 hours. The reaction mixture was quenched with water (500 mL) and extracted with ethyl acetate (250 mL×3). The combined organic layer was washed with water, brine, dried over MgSO$_4$ and concentrated. The resultant residue was purified by flash chromatography (120 g silica gel, 0-20% ethyl acetate in hexanes) to get the title compound as a colorless oil. $^1$H NMR (300 MHz, CDCl$_3$): δ 3.71 (s, 1H), 3.69 (d, J=5.0 Hz, 1H), 2.87 (t, J=5.4 Hz, 1H), 2.00-1.72 (m, 6H), 0.91 (s, 6H), 0.10 (s, 6H).

Step 2: (1-(((tert-butyldimethylsilyl)oxy)methyl)cyclobutyl)methyl methanesulfonate To a solution of (1-(((tert-butyldimethylsilyl)oxy)methyl)cyclobutyl)methanol (9.9 g, 43.0 mmol) in anhydrous dichloromethane (250 mL), N,N-diisopropylethylamine (11.2 mL, 64.4 mmol) and methanesulfonyl chloride (3.66 ml, 47.3 mmol) were added at 0° C. The reaction mixture was stirred at 0° C. for 2 hours. The reaction mixture was quenched with saturated aqueous NaHCO$_3$ (250 mL) and extracted with dichloromethane (250 mL×3). The combined organic layer was dried over MgSO$_4$ and concentrated to get the crude title compound as a brown oil (11.8 g, 80%). $^1$H NMR (300 MHz, CDCl$_3$): δ 4.21 (s, 2H), 3.59 (s, 2H), 3.00 (s, 3H), 1.95-1.76 (m, 6H), 0.89 (s, 9H), 0.06 (s, 6H).

Step 3: ((1-((3-chlorophenylthio)methyl)cyclobutyl)methoxy)(tert-butyl)dimethylsilane A microwave tube was charged with cesium carbonate (4.05 g, 12.4 mmol), 3-chlorothiophenol (1.5 g, 10.4 mmol), dimethyl sulfoxide (20 mL), and (1-(((tert-butyldimethylsilyl)oxy)methyl)cyclobutyl)methyl methanesulfonate (3.9 g, 11.4 mmol). The reaction mixture was stirred at 80° C. for 16 hours. The reaction mixture was cooled to room temperature and quenched with water (100 mL) and extracted with ethyl acetate (50 mL×3). The combined organic layer was washed with water, brine, dried over MgSO$_4$ and concentrated to dryness. The resultant residue was purified by flash chromatography (40 g silica gel, 100% hexane) to get the title compound as a colorless oil (3.54 g, 96%). $^1$H NMR (300 MHz, CDCl$_3$): δ 7.31 (s, 1H), 7.24-7.06 (m, 3H), 3.61 (s, 2H), 3.15 (s, 2H), 1.86-1.81 (m, 6H), 0.89 (s, 9H), 0.04 (s, 6H).

Step 4: (1-((4-bromo-3-chlorophenylthio)methyl)cyclobutyl)methanol

To a solution of ((1-((3-chlorophenylthio)methyl)cyclobutyl)methoxy)(tert-butyl)dimethylsilane (670 mg, 1.9 mmol) in dichloromethane (40 mL) under an ice-bath, bromine (0.11 ml, 2.1 mmol) in dichloromethane (5 mL) was added slowly into the reaction over 20 minutes. The reaction mixture was warmed to room temperature and stirred for 16 hours. The reaction mixture was concentrated and the resultant residue was purified by flash column (25 g silica gel, 0-20% ethyl acetate in hexanes) to get the desired product as a pale yellow oil (400 mg, 66%) and silyl compound 990 mg, 11%). $^1$H NMR (300 MHz, CDCl$_3$): δ 7.47 (d, J=8.4 Hz, 1H), 7.43 (d, J=2.2 Hz, 1H), 7.09 (dd, J=8.4 and 2.3 Hz, 1H), 3.70 (s, 2H), 3.19 (s, 2H), 1.92-1.85 (m, 6H).

Step 5: (1-((4-bromo-3-chlorophenylsulfonyl)methyl)cyclobutyl)methanol

To a solution of (1-((4-bromo-3-chlorophenylthio)methyl)cyclobutyl)methanol (400 mg, 1.2 mmol) dissolved in dichloromethane (12 mL) was added m-CPBA (640 mg, 3.7 mmol) at 0° C. The reaction mixture was warmed to room temperature and stirred for 20 hours. The reaction mixture was washed with saturated NaHCO$_3$ (15 mL×2), water, brine and dried over MgSO$_4$. The solvents were removed to dryness and the residue was purified by flash chromatography (12 g silica gel, 0-30% ethyl acetate in hexanes) to get the title compound as a white solid (370 mg, 84%). $^1$H NMR (300 MHz, CDCl$_3$): δ 7.99 (d, J=2.1 Hz, 1H), 7.84 (d, J=8.3 Hz, 1H), 7.65 (dd, J=8.4 and 2.1 Hz, 1H), 3.96 (s, 2H), 3.67 (s, 2H), 2.06-1.89 (m, 6H).

The intermediates listed below can be prepared according to the general procedures described above for Intermediate A13, using starting materials which are commercially-available or readily-available using procedures known to one of ordinary skill in the art.

| Intermediate |
|---|
| 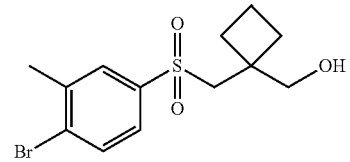 |
| 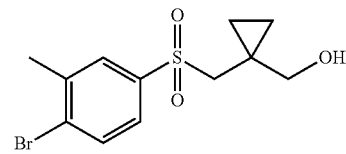 [SMILES: Cc1cc(S(=O)(=O)CC2(CO)CC2)ccc1Br] |
| 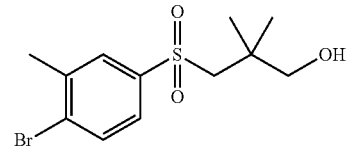 |

Intermediate B:
3-bromo-6-(cyclopentyloxy)-2-methylpyridine

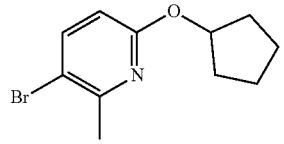

A round bottom flask was charged with 5-bromo-2-fluoro-6-picoline (2.00 g, 10.5 mmol), cesium carbonate (6.86 g, 21.1 mmol), DMF (20 mL) and cyclopentanol (1.36 g, 15.8 mmol) and the reaction mixture heated to 90° C. for 3 hours. The reaction mixture was cooled to room temperature and quenched with water and extracted with ethyl acetate (3×25 mL). The combined organic extracts were washed with brine and dried over MgSO$_4$. The solvents were evaporated to dryness and the residue was purified by flash chromatography (silica gel, 0-30% ethyl acetate in hexanes) to afford the product as white solid (700 mg, 26%). LC/MS: [M+1]$^+$ 256.5; $^1$H NMR (300 MHz, CDCl$_3$): δ 7.59 (d, J=8.7 Hz, 1H), 6.40 (d, J=8.7 Hz, 1H), 5.33-5.28 (m, 1H), 2.53 (s, 3H), 1.99-1.91 (m, 2H), 1.81-1.73 (m, 4H), 1.64-1.59 (m, 2H).

The intermediates listed below were prepared according to the general procedures described above for Intermediate B, using starting materials which are commercially-available or readily-available using procedures known to one of ordinary skill in the art.

| Intermediate | $^1$H NMR (CDCl$_3$, 300 MHz) |
|---|---|
| 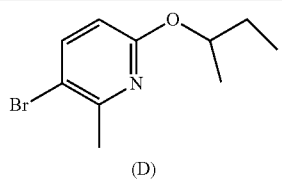<br>(D) | δ 7.58 (d, J = 8.7 Hz, 1H), 6.40 (d, J = 8.7 Hz, 1H), 5.09-5.03 (m, 1H), 2.52 (s, 3H), 1.74-1.59 (m 2H), 1.28 (d, J = 6.3 Hz, 3H), 0.94 (t, J = 7.2 Hz, 3H). |

-continued
| Intermediate | ¹H NMR (CDCl₃, 300 MHz) |
|---|---|
| 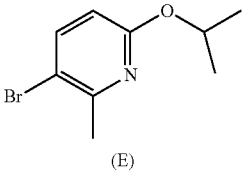<br>(E) | δ 7.58 (d, J = 8.7 Hz, 1H), 6.40 (d, J = 8.7 Hz, 1H), 5.28-5.2 (m, 1H), 2.52 (s, 3H), 1.32 (d, J = 7.5 Hz, 6H). |
| 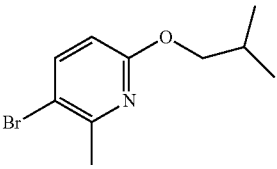<br>(F) | δ 7.60 (d, J = 9.0 Hz, 1H), 6.45 (d, J = 8.1 Hz, 1H), 4.01 (d, J = 6.9 Hz, 2H), 2.53 (s, 3H), 2.11-2.02 (m, 1H), 0.99 (d, J = 12 Hz, 6H). |
| 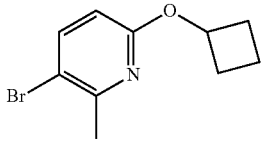<br>(G) | δ 7.60 (d, J = 9.0 Hz, 1H), 6.39 (d, J = 8.7 Hz, 1H), 5.10-5.05 (m, 1H), 2.51 (s, 3H), 2.48-2.38 (m, 2H), 2.15-2.05 (m, 2H), 1.87-1.61 (m, 2H). |
| 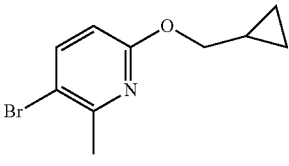<br>(H) | δ 7.60 (d, J = 9.0 Hz, 1H), 6.48 (d, J = 8.7 Hz, 1H), 4.08 (d, J = 7.5 Hz, 2H), 2.52 (s, 3H), 1.26 (m, 1H), 0.62-0.58 (m, 2H), 0.36-0.33 (m, 2H). |
| 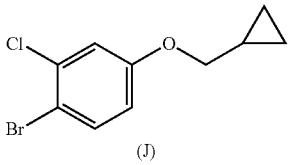<br>(J) | δ 7.47 (d, J = 8.7 Hz, 1H), 7.01 (d, J = 3.0 Hz, 1H), 6.70 (dd, J = 8.7 and 3.0 Hz, 1H), 3.78 (d, J = 7.2 Hz, 2H), 1.26 (m, 1H), 0.68-0.63 (m, 2H), 0.38-0.34 (m, 2H). |
| 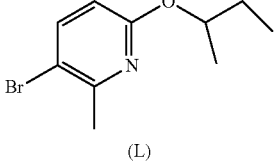<br>(L) | δ 7.58 (d, J = 8.7 Hz, 1H), 6.40 (d, J = 8.7 Hz, 1H), 5.09-5.03 (m, 1H), 2.52 (s, 3H), 1.74-1.59 (m 2H), 1.28 (d, J = 6.3 Hz, 3H), 0.94 (t, J = 7.2 Hz, 3H). |
| 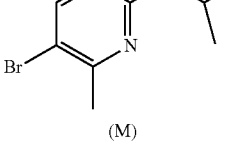<br>(M) | δ 7.58 (d, J = 8.7 Hz, 1H), 6.40 (d, J = 8.7 Hz, 1H), 5.28-5.2 (m, 1H), 2.52 (s, 3H), 1.32 (d, J = 7.5 Hz, 6H). |
| 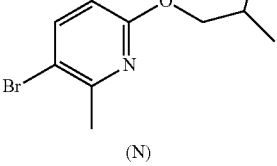<br>(N) | δ 7.60 (d, J = 9.0 Hz, 1H), 6.45 (d, J = 8.1 Hz, 1H), 4.01 (d, J = 6.9 Hz, 2H), 2.53 (s, 3H, 2.11-2.02 (m, 1H), 0.99 (d, J = 7.2 Hz, 6H). |

| Intermediate | ¹H NMR (CDCl₃, 300 MHz) |
|---|---|
| 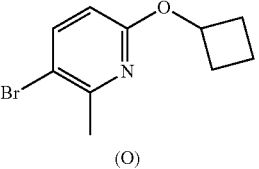<br>(O) | δ 7.60 (d, J = 9.0 Hz, 1H), 6.39 (d, J = 8.7 Hz, 1H), 5.10-5.05 (m, 1H), 2.51 (s, 3H), 2.48-2.38 (m, 2H), 2.15-2.05 (m, 2H), 1.87-1.61 (m, 2H). |
| 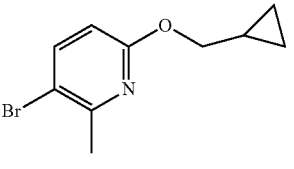<br>(P) | δ 7.60 (d, J = 9.0 Hz, 1H), 6.48 (d, J = 8.7 Hz, 1H), 4.08 (d, J = 7.5 Hz, 2H), 2.52 (s, 3H), 1.26 (m, 1H), 0.62-0.58 (m, 2H), 0.36-0.33 (m, 2H). |
| 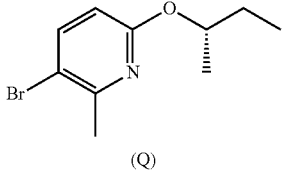<br>(Q) | δ 7.58 (d, J = 8.7 Hz, 1H), 6.40 (d, J = 8.1 Hz, 1H), 5.09-5.03 (m, 1H), 2.52 (s, 3H), 1.77-1.58 (m, 2H), 1.28 (d, J = 6.3 Hz, 3H), 0.94 (t, J = 7.4 Hz, 3H). |
| 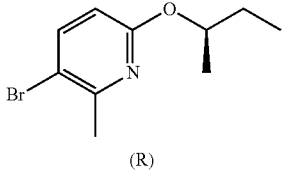<br>(R) | δ 7.58 (d, J = 8.7 Hz, 1H), 6.40 (d, J = 8.7 Hz, 1H), 5.09-5.03 (m, 1H), 2.52 (s, 3H), 1.74-1.58 (m, 2H), 1.28 (d, J = 6.3 Hz, 3H), 0.94 (t, J = 7.4 Hz, 3H). |
| 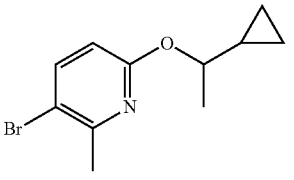<br>(S) | δ 7.58 (d, J = 8.7 Hz, 1H), 6.43 (d, J = 9.0 Hz, 1H), 4.66-4.57 (m, 1H), 2.49 (s, 3H), 1.36 (d, J = 6.3 Hz, 3H), 1.27-1.23 (m, 2H), 1.15-1.03 (m, 1H), 0.58-0.54 (m, 2H). |
| 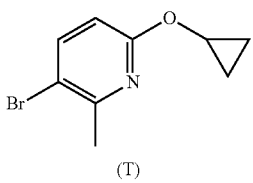<br>(T) | δ 7.67 (d, J = 8.7 Hz, 1H), 6.58 (d, J = 8.1 Hz, 1H), 4.12-4.09 (m, 1H), 2.57 (s, 3H), 0.79-0.78 (m, 4H). |
| 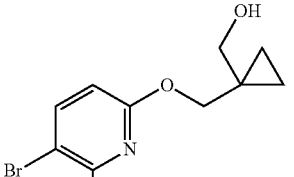<br>(U) | δ 7.65 (d, J = 8.7 Hz, 1H), 6.51 (d, J = 9.0 Hz, 1H), 4.27 (s, 2H), 3.63 (t, J = 7.2 Hz, 1H), 3.41 (d, J = 6.9 Hz, 1H), 2.54 (s, 3H), 0.64-0.55 (m, 4H). |

-continued

| Intermediate | ¹H NMR (CDCl₃, 300 MHz) |
|---|---|
| 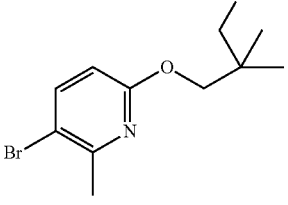<br>(V) | δ 7.65 (d, J = 9.0 Hz, 1H), 6.49 (d, J = 8.1 Hz, 1H), 4.15 (s, 2H), 4.01 (t, J = 7.2 Hz, 1H), 3.25 (d, J = 6.9 Hz, 2H), 2.53 (s, 3H), 0.97 (s, 6H). |
| 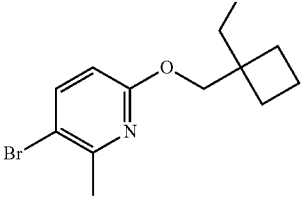<br>(W) | δ 7.64 (d, J = 9 Hz, 1H), 6.48 (d, J = 8.7 Hz, 1H), 4.41 (s, 2H), 3.86 (t, J = 6.9 Hz, 1H), 3.52 (d, J = 7.2 Hz, 2H), 2.53 (s, 3H), 2.01-1.83 (m, 6H). |
| 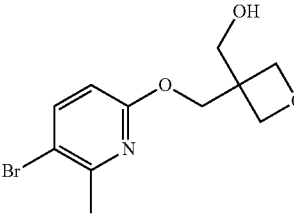<br>(X) | δ 7.67 (d, J = 8.1 Hz, 1H), 6.49 (d, J = 8.4 Hz, 1H), 4.70 (s, 2H), 4.56-4.49 (m, 4H), 3.81 (m, 1H), 2.53 (s, 3H). |
| 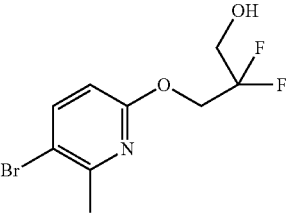<br>(X1) | δ 7.74 (d, J = 8.7 Hz, 1H), 6.61 (d, J = 8.7 Hz, 1H), 4.64 (t, J = 7.2 Hz, 2H), 4.00 (bs, 1H), 3.78 (t, J = 7.2 Hz, 2H), 2.57 (s, 3H). |

Intermediate Y:
1-Bromo-2-chloro-4-(cyclopropylmethoxy)benzene was Prepared According to the Following Scheme

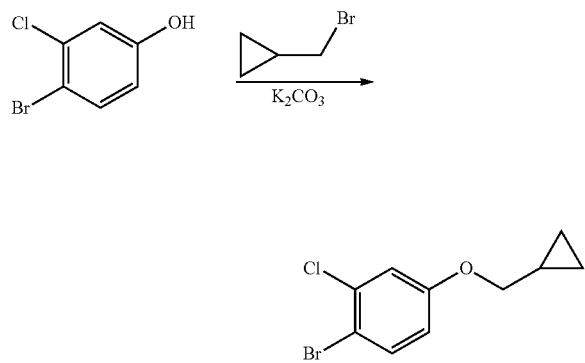

Step 1:
1-Bromo-2-chloro-4-(cyclopropylmethoxy)benzene

A microwave vial was charged with 4-bromo-3-chlorophenol (1.00 g, 4.8 mmol), potassium carbonate (1.0 g, 7.2 mmol), DMF (15 mL) and cyclopropylmethyl bromide (0.78 g, 5.8 mmol) and the reaction stirred at room temperature overnight. The reaction mixture was quenched with water and extracted with ethyl acetate (3×50 mL). The combined organics were washed with brine and dried over MgSO₄. The solvents were evaporated to dryness and the residue subjected to purification by column chromatography (24 g silica, 0-50% ethyl acetate in hexanes) to give the product as oil. ¹H NMR (300 MHz, CDCl₃): δ 7.47 (d, J=8.7 Hz, 1H), 7.01 (d, J=3.0 Hz, 1H), 6.70 (dd, J=8.7 and 3.0 Hz, 1H), 3.78 (d, J=7.2 Hz, 2H), 1.26 (m, 1H), 0.68-0.63 (m, 2H), 0.38-0.34 (m, 2H).

The intermediates listed below were prepared according to the general procedures described above for Intermediate Y, using starting materials which are commercially-available or readily-available using procedures known to one of ordinary skill in the art.

| Intermediate | ¹H NMR (CDCl₃, 300 MHz) |
|---|---|
| 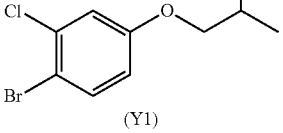 (Y1) | δ 7.45 (d, J = 8.7 Hz, 1H), 7.00 (d, J = 3.0 Hz, 1H), 6.69 (dd, J = 8.7 and 3.0 Hz, 1H), 3.68 (d, J = 6.3 Hz, 2H), 2.11-2.02 (m, 1H), 1.01 (d, J = 6.9 Hz, 6H). |
| 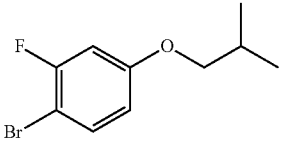 (Y2) | δ 7.38 (t, J = 8.7 Hz, 1H), 6.69 (dd, J = 10.2 Hz and 3.0 Hz, 1H), 6.60 (dd, J = 8.7 and 1.8 Hz, 1H), 3.68 (d, J = 6.6 Hz, 2H), 2.12-2.03 (m, 1H), 1.01 (d, J = 6.3 Hz, 6H). |
| 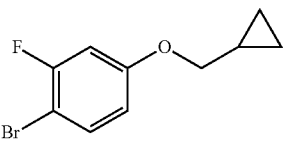 (Y3) | δ 7.38 (t, J = 8.7 Hz, 1H), 6.68 (dd, J = 9.9 and 2.7 Hz, 1H), 6.60 (dd, J = 9.3 and 2.4 Hz, 1H), 3.76 (d, J = 6.9 Hz, 2H), 1.30-1.20 (m, 1H), 0.68-0.62 (m, 2H), 0.40-0.32 (m, 2H). |
| 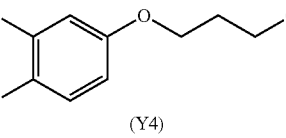 (Y4) | δ 7.43 (d, J = 8.7 Hz, 1H), 6.99 (d, J = 2.7 Hz, 1H), 6.67 (dd, J = 9.0 and 3.0 Hz, 1H), 4.04 (t, J = 6.2 Hz, 2H), 3.81 (t, J = 6.2 Hz, 2H), 2.06-1.98 (m, 2H). |
| 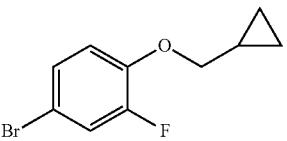 (Y5) | δ 7.25-7.16 (m, 2H), 6.83 (t, J = 8.9 Hz, 1H), 3.86 (d, J = 7.2 Hz, 2H), 1.31-1.27 (m, 1H), 0.69-0.63 (m, 2H), 0.38-0.33 (m, 2H). |
| 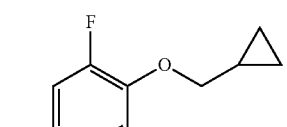 (Y6) | δ 7.12-7.05 (m, 2H), 3.95 (d, J = 7.8 Hz, 2H), 1.29-1.21 (m, 1H), 0.63-0.57 (m, 2H), 0.32-0.29 (m, 2H). |
| 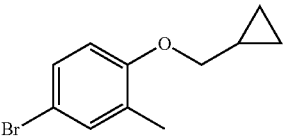 (Y7) | δ 7.26-7.19 (m, 2H), 6.65 (d, J = 8.7 Hz, 1H), 3.78 (d, J = 6.9 Hz, 2H), 2.21 (s, 3H), 1.27-1.21 (m, 1H), 0.65-0.58 (m, 2H), 0.37-0.32 (m, 2H). |

Intermediate Z: (3-(4-bromo-3-chlorophenoxy)butoxy)(tert-butyl)dimethylsilane was Prepared According to the Following Scheme

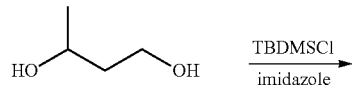

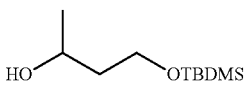

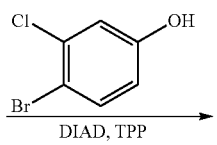

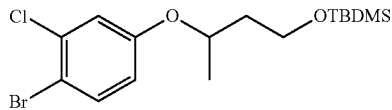

Step 1: 4-((tert-butyldimethylsilyl)oxy)butan-2-ol

To an ice-cold solution of 1,3-butanediol (1.27 g, 14.1 mmol) in DMF (33.0 mL), imidazole (1.44 g, 21.1 mmol) and TBDMSCl (2.15 g, 14.2 mmol) were added. After stirring for 1 hour, the mixture was diluted with ether (40 mL), washed with water, dried over anhydrous sodium sulfate, filtered, and concentrated. The residue was purified by silica gel column chromatography (0-20% ethyl acetate in hexanes) to afford the title compound as a colorless oil (1.8 g). $^1$H NMR (300 MHz, CDCl$_3$): δ 3.84-3.77 (m, 1H), 3.59 (dd, J=9.9, 3.6 Hz, 1H), 3.34 (dd, J=9.3, 2.1 Hz, 1H), 2.45 (d, J=3.0 Hz, 1H), 1.11 (d, J=6.0 Hz, 3H), 0.91 (s, 9H), 0.08 (s, 6H).

Step 2: (3-(4-bromo-3-chlorophenoxy)butoxy)(tert-butyl)dimethylsilane

A round bottom flask was charged with triphenylphosphine (0.54 g, 2.0 mmol), 4-bromo-3-chlorophenol (0.43 g, 2.0 mmol), 4-((tert-butyldimethylsilyl)oxy)butan-2-ol (0.39 g, 1.9 mmol) and anhydrous THF (20 mL). The reaction mixture was cooled to 0° C. and DIAD (0.40 mL, 2.0 mmol) was added dropwise. Ice-bath was then removed and the resulting mixture was stirred at room temperature overnight. The resulting mixture was concentrated and diluted with ethyl acetate (20 mL). This was washed with saturated sodium bicarbonate (2×10 mL), brine, and dried over anhydrous sodium sulfate. The solvents were evaporated to dryness and the resulting residue purified by flash chromatography (25 g silica, 0-20% ethyl acetate in hexanes) to afford the title compound as a colorless oil (0.37 g, 50%). $^1$H NMR (300 MHz, CDCl$_3$): δ 7.44 (d, J=8.7 Hz, 1H) 7.03 (d, J=2.7 Hz, 1H), 6.70 (dd, J=9.0, 2.8 Hz, 1H), 4.57=4.49 (m, 1H), 3.78-3.65 (m, 2H), 1.98-1.68 (m, 2H), 1.30 (d, J=6.0 Hz, 3H), 0.88 (s, 9H), 0.02 (d, J=5.7 Hz, 6H).

Intermediate AA: 1-bromo-2-chloro-4-(1-cyclopropylethoxy)benzene was Prepared According to the Following Scheme

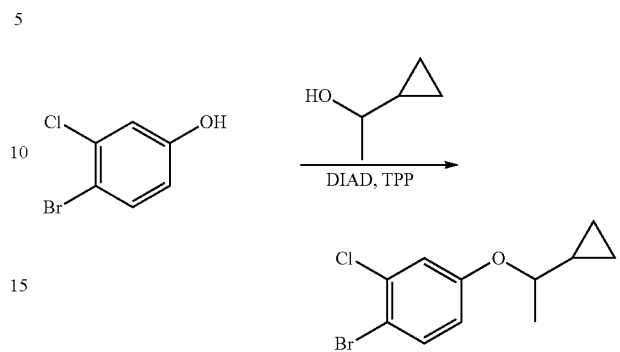

Step 1: 1-bromo-2-chloro-4-(1-cyclopropylethoxy)benzene

A round bottom flask was charged with triphenylphosphine (2.02 g, 7.7 mmol), diisopropyl azodicarboxylate (DIAD) (1.23 mL, 6.3 mmol) in THF (50 mL). Reaction mixture was stirred for 15 min at room temperature. 1-cyclopropylethanol (0.47 mL, 4.8 mmol) followed by 4-bromo-3-chlorophenol (1.00 g, 4.8 mmol) were then added in one portion to the previously formed solution. The reaction mixture was stirred at room temperature overnight. Solvents were evaporated. The residue was purified by flash chromatography (40 g, 0-50% ethyl acetate in hexanes) and the product fractions were collected to give the title compound (purity: 70%) as a colorless oil. Without further purification, the colorless oil was used in the next step.

The intermediates listed below were prepared according to the general procedures described above for Intermediate AA, using starting materials which are commercially-available or readily-available using procedures known to one of ordinary skill in the art.

| Intermediate | $^1$H NMR (CDCl$_3$, 300 MHz) |
|---|---|
| (AA1) | δ 7.45 (d, J = 8.7 Hz, 1H), 6.99 (d, J = 2.4 Hz, 1H), 6.67 (dd, J = 9.3 and 2.7 Hz, 1H), 4.29-4.19 (m, 1H), 1.77-1.57 (m, 2H), 1.28 (d, J = 6.3 Hz, 3H), 0.96 (t, J = 7.5 Hz, 3H). |
| (AA2) | δ 7.45 (d, J = 9.3 Hz, 1H), 6.99 (d, J = 2.1 Hz, 1H), 6.67 (dd, J = 8.8 and 2.8 Hz, 1H), 4.29-4.19 (m, 2H), 1.28 (d, J = 5.7 Hz, 3H), 0.99 (t, J = 7.5 Hz, 3H). |
| (AA3) | δ 7.41 (d, J = 8.7 Hz, 1H), 6.97 (d, J = 3.0 Hz, 1H), 6.65 (dd, J = 8.7, and 3.0 Hz, 1H), 3.84 (s, 2H), 3.55 (s, 2H), 2.39 (m, 1H), 0.58 (m, 4H)., |

| Intermediate | ¹H NMR (CDCl₃, 300 MHz) |
|---|---|
| 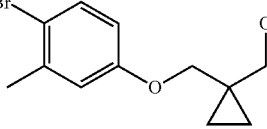<br>(AA4) | δ 7.38 (d, J = 8.1 Hz, 1H), 6.79 (d, J = 2.7 Hz, 1H), 6.60 (dd, J = 9.0 and 3.0 Hz, 1H), 3.88 (s, 2H), 3.62 (s, 2H), 2.35 (s, 3H), 2.18 (bs, 1H), 0.63 (s, 4H). |

Intermediate BB: (3-(4-bromo-3-chlorophenoxy)-2,2-dimethylpropoxy)(tert-butyl)dimethylsilane was Prepared According to the Following Scheme

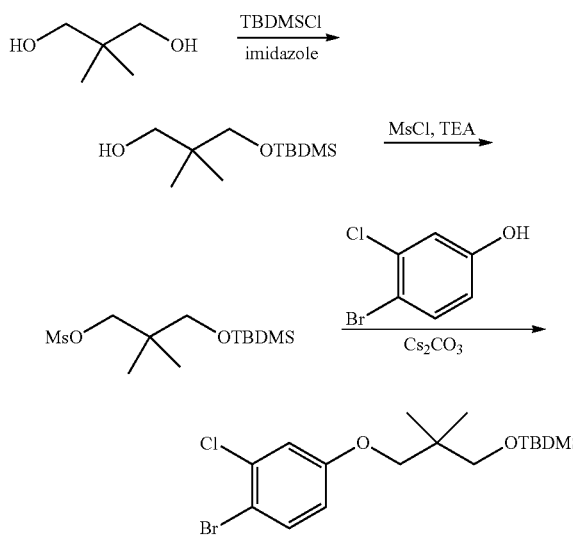

Step 1: 3-((tert-butyl dim ethyl silyl)oxy)-2,2-dimethyl propan-1-ol

To an ice-cold solution of 2,2-dimethylpropane-1,3-diol (1.0 g, 9.6 mmol) in DMF 15 mL) were added imidazole (1.0 g, 14.4 mmol) and tert-butyldimethylsilyl chloride (1.45 g, 9.6 mmol). After stirring for 1 hour, the mixture was diluted with ether (30 mL), washed with water, dried over sodium sulfate. The solvents were concentrated and the residue was purified by flash chromatography (40 g silica, 0-20% ethyl acetate in hexanes) to give a colorless oil (1.2 g). ¹H NMR (300 MHz, CDCl₃): δ 3.46 (s, 4H), 2.83 (t, J=5.6 Hz, 1H), 0.89 (s, 9H), 0.88 (s, 6H), 0.06 (s, 6H).

Step 2: 3-((tert-butyldimethylsilyl)oxy)-2,2-dimethylpropyl methanesulfonate

To the solution of 3-((tert-butyldimethylsilyl)oxy)-2,2-dimethylpropan-1-ol (1.3 g, 6.0 mmol) and triethylamine (1.7 mL, 12.1 mmol) in DCM (15 mL) at 0° C. was added a DCM solution (3 mL) of methanesulfonyl chloride (0.56 mL, 7.3 mmol). The reaction mixture was stirred at 0° C. for 2 hours. Water (10 mL) was added and the organic layer was separated. The aqueous layer was extracted with dichloromethane (2×30 mL). The combined organic layers were washed with diluted aqueous HCl solution, saturated aqueous NaHCO₃ solution, brine and dried over sodium sulfate. The solvents were evaporated to give the product as a yellow oil (1.72 g). ¹H NMR (300 MHz, CDCl₃), δ 3.99 (s, 2H), 3.34 (s, 2H), 2.98 (s, 3H), 0.92 (s, 6H), 0.89 (s, 9H), 0.04 (s, 6H).

Step 3: (3-(4-bromo-3-chlorophenoxy)-2,2-dimethylpropoxy)(tert-butyl)dimethylsilane A microwave vial was charged with 3-((tert-butyldimethylsilyl)oxy)-2,2-dimethylpropyl methanesulfonate (1.0 g, 3.4 mmol), 4-bromo-3-chlorophenol (0.8 g, 3.7 mmol) and cesium carbonate (2.75 g, 8.4 mmol) in DMF (15 mL). The reaction mixture was heated to 120° C. in microwave for 2 hours. The reaction was cooled to room temperature and quenched with water and extracted with ethyl acetate (3×50 mL). The organics were washed with water, brine, and dried over sodium sulfate. The solvents were evaporated. The residue was purified by flash chromatography (24 g silica, 0-10% ethyl acetate in hexanes) to give a colorless oil (175 mg). ¹H NMR (300 MHz, CDCl₃): δ 7.45 (d, J=8.1 Hz, 1H), 7.01 (d, J=3.0 Hz, 1H), 6.71-6.67 (m, 1H), 3.66 (s, 2H), 3.41 (s, 2H), 0.96 (s, 6H), 0.86 (s, 9H), 0.03 (s, 6H).

The intermediates listed below were prepared according to the general procedures described above for Intermediate BB, using starting materials which are commercially-available or readily-available using procedures known to one of ordinary skill in the art.

| Intermediate | ¹H NMR (CDCl₃, 300 MHz) |
|---|---|
| 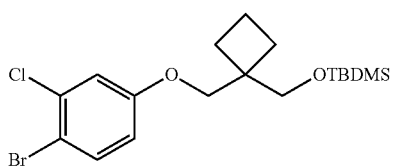<br>(BB1) | δ 7.45 (d, J = 8.7 Hz, 1H), 7.29 (d, J = 2.7 Hz, 1H), 6.71 (dd, J = 9.0, 2.2 Hz, 1H), 3.87 (s, 2H), 3.64 (s, 2H), 1.88-1.87 (m, 6H), 0.86 (s, 9H), 0.01 (s, 6H). |

| Intermediate | $^1$H NMR (CDCl$_3$, 300 MHz) |
|---|---|
| 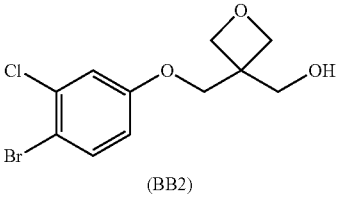<br>(BB2) | δ 7.51 (d, J = 8.7 Hz, 1H), 7.07 (d, J = 3.0 Hz, 1H), 6.75 (dd, J = 9.3 and 3.0 Hz, 1H), 4.60-4.51 (m, 4H), 4.22 (s, 2H), 4.03 (d, J = 4.2 Hz, 2H). |

Intermediate CC: 2-(4-bromo-3-chlorophenoxy)propan-1-ol was Prepared According to the Following Scheme

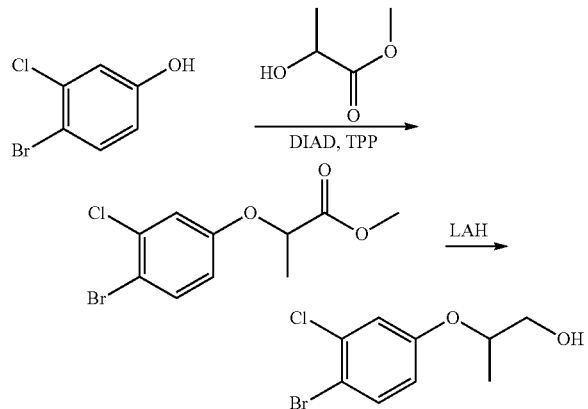

Step 1: Methyl 2-(4-bromo-3-chlorophenoxy)propanoate

A round bottom flask was charged with triphenylphosphine (2.9 g, 11.2 mmol), 4-bromo-3-chlorophenol (2.3 g, 11.2 mmol), 98.0% Methyl DL-lactate (1.2 g, 11.1 mmol) and dry THF (20 mL). Reaction mixture was cooled to 0° C. and DIAD (2.20 mL, 11.2 mmol) was added dropwise. Ice-bath was then removed and the resulting mixture was stirred at room temperature overnight. The mixture was concentrated and purified by flash chromatography (40 g, 0-50% ethyl acetate in hexanes) to afford the title compound as a thick yellow oil (2.53 g, 77%). $^1$H NMR (300 MHz, CDCl$_3$): δ 7.47 (d, J=9.0 Hz, 1H), 6.99 (d, J=2.7 Hz, 1H), 6.66 (dd, J=9.5, 2.8 Hz, 1H), 4.71 (q, J=6.9 Hz, 1H), 3.77 (s, 3H), 1.62 (d, J=6.9 Hz, 3H).

Step 2: 2-(4-bromo-3-chlorophenoxy)propan-1-ol

Methyl 2-(4-bromo-3-chlorophenoxy)propanoate (2.50 g, 8.5 mmol) was dissolved in dry THF (10 mL) under argon and the resulting mixture was cooled to 0° C. Lithium aluminum hydride (0.33 g, 8.6 mmol) was added in one portion. After 1 hour of stirring at 0° C., the reaction was carefully quenched with saturated Rochelle salt solution and extracted with ethyl acetate (3×50 ml). A clear oil was obtained after concentration. $^1$H NMR (300 MHz, CDCl$_3$): δ 7.48 (d, J=8.7 Hz, 1H), 7.20 (t, J=8.6 Hz, 1H), 7.05 (d, J=2.4 Hz, 1H), 6.96-6.94 (m, 1H), 6.84-6.81 (m, 1H), 6.75-6.71 (m, 1H), 4.51-4.42 (m, 2H), 3.79-3.67 (m, 4H), 1.95-1.88 (m, 2H), 1.29-1.26 (m, 6H).

Example 1: 5-(4-(6-(cyclopentyloxy)-2-methylpyridin-3-yl)-1H-pyrazol-1-yl)-1-propylpyridin-2(1H)-one

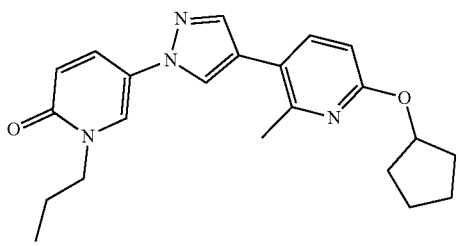 [SMILES: CCCn1cc(-n2cc(-c3ccc(OC4CCCC4)nc3C)cn2)ccc1=O]

Step 1: 5-bromo-1-propylpyridin-2(1H)-one

A round bottom flask was charged with 2-hydroxy-5-bromopyridine (1.00 g, 5.7 mmol), 1-iodopropane (2.81 mL, 28.7), potassium carbonate (3.97 g, 28.7 mmol) and tween 80 (2% w/w in water, 10 mL) and the reaction mixture was heated to 70° C. overnight. The reaction mixture was diluted with water and extracted with ethyl acetate (3×50 mL) and the combined organics were washed with brine and dried over MgSO$_4$. The solvents were evaporated to dryness and the residue purified by flash chromatography (silica gel, 0-50% ethyl acetate in hexanes). The desired fractions were evaporated to dryness to give the compound as colorless oil. LC/MS: [M$^+$] and [M+2]$^+$ 216.1 and 218.1; $^1$H NMR (300 MHz, DMSO-d6): δ 8.00 (d, J=2.7 Hz, 1H), 7.49 (dd, J=9.9 and 3.0 Hz, 1H), 6.34 (d, J=10.2 Hz, 1H), 3.79 (t, J=6.9 Hz, 2H), 1.64-1.57 (m, 2H), 0.82 (t, J=7.5 Hz, 3H).

Step 2: 5-(4-bromo-1H-pyrazol-1-yl)-1-propylpyridin-2(1H)-one

To a stirred solution of 5-bromo-1-propylpyridin-2(1H)-one (1.03 g, 4.8 mmol), cesium carbonate (4.65 g, 14.3 mmol), 3-bromopyrazole (0.70 g, 4.8 mmol), in anhydrous DMA (3 mL) under argon was added and copper(I) iodide (0.18 g, 1.0 mmol). The mixture was stirred at 120° C. overnight. After cooling, the mixture was diluted with water and extracted with ethyl acetate (3×20 mL). The combined organics were washed with brine and dried over MgSO$_4$. The solvents were dried to evaporation and the residue purified by flash chromatography (0-100% ethyl acetate in hexanes). The pure fractions were collected and dried to give the product as a liquid (320 mg, 24%). LC/MS: [M+1]$^+$ 282.1; ¹H NMR (300 MHz, CDCl₃): δ 8.25 (d, J=2.4 Hz, 1H), 7.84-7.76 (m, 2H), 7.66 (dd, J=9.9 and 2.4 Hz, 1H), 7.56 (dd, J=8.7 and 2.4 Hz, 1H) 6.68 (d, J=9.9 Hz, 1H), 6.55 (d, J=8.1 Hz, 1H), 4.51 (bs, 2H), 3.96 (t, J=7.8 Hz, 2H), 1.87-1.80 (m, 2H), 0.99 (t, J=7.5 Hz, 3H).

Step 3: 1-propyl-5-(4-(4,4,5,5-tetramethyl-1,3,2-dioxaborolan-2-yl)-1H-pyrazol-1-yl)pyridin-2(1H)-one A round bottom flask was charged with 5-(4-bromo-1H-pyrazol-1-yl)-1-propylpyridin-2(1H)-one (7.72 g, 27.4 mmol), bis(pinacolato)diboron (13.9 g, 54.7 mmol), potassium acetate (8.1 g, 82.1 mmol) in anhydrous DMSO (35 mL) and the flask was degassed and flushed with argon. [1,1'-Bis(diphenylphosphino)ferrocene]dichloropalladium (II), complex with dichloromethane (1.12 g, 1.4 mmol) was added and the reaction flask was again degassed and flushed with argon. The reaction mixture was then heated to 70° C. overnight. The reaction mixture was cooled to room temperature and quenched with water and extracted with ethyl acetate (3×500 mL). The combined organics were washed with brine and dried over sodium sulfate. The solvents were concentrated and the residue was purified by flash chromatography (80 g silica, 0-70% ethyl acetate in hexanes) to give the product as a pale yellow solid (4.5 g). LC/MS: [M+1]⁺ 330.3. ¹H NMR (300 MHz, DMSO-d6): δ 8.48 (s, 1H), 8.29 (d, J=3.0 Hz, 1H), 7.95-7.91 (m, 1H), 7.80 (s, 1H), 6.48 (d, J=9.9 Hz, 1H), 3.91-3.84 (m, 2H), 1.71-1.64 (m, 2H), 1.26 (s, 12H), 0.86 (t, J=7.7 Hz, 3H).

Step 4: 5-(4-(6-(cyclopentyloxy)-2-methylpyridin-3-yl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl) pyridin-2(1H)-one (0.25 g, 0.8 mmol), 3-bromo-6-(cyclopentyloxy)-2-methylpyridine (0.28 g, 0.8 mmol), potassium carbonate (0.32 g, 2.4 mmol) and 1,4-dioxan (12 mL) and water (3 mL) and the flask was degassed and flushed with argon. Pd(dppf)Cl₂ (0.062 g, 0.1 mmol) was added and the reaction flask was again degassed and flushed with argon. The reaction mixture was then heated to 100° C. in a microwave for 90 minutes. The reaction was cooled to room temperature and quenched with saturated NaHCO₃ and extracted with ethyl acetate (3×50 mL). The combined organics were washed with water, brine and dried over MgSO₄. The solvents were evaporated to dryness and the residue purified by flash chromatography (12 g silica gel, 0-40% ethyl acetate in hexanes) to afford the product as white solid (110 mg, 38%). LC/MS: [M+1]⁺ 379.4; ¹H NMR (300 MHz, CDCl₃): δ 7.80-7.65 (m, 4H), 7.50 (d, J=9.0 Hz, 1H), 6.70 (d, J=9.3 Hz, 1H), 6.58 (d, J=9.1 Hz, 1H), 5.38-5.35 (m, 1H), 3.99 (t, J=7.5 Hz, 2H), 2.54 (s, 3H), 2.01-1.64 (m, 10H), 1.02 (t, J=7.5 Hz, 3H).

The compounds listed below were prepared according to the general procedure described above for Example 1, using starting materials which are commercially-available or readily-available using procedures known to one of ordinary skill in the art.

| Ex No | Structure | ¹H NMR (CDCl₃, 300 MHz) | LC/MS[M + 1] |
|---|---|---|---|
| 2 | 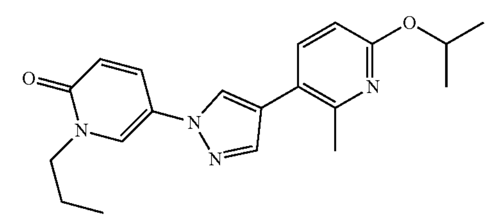 [SMILES: CCCn1cc(-n2cc(-c3ccc(OC(C)C)nc3C)cn2)ccc1=O] | δ 7.80-7.65 (m, 4H), 7.50 (d, J = 8.7 Hz, 1H), 6.70 (d, J = 8.7 Hz, 1H), 6.57 (d, J = 8.1 Hz, 1H), 5.37-5.29 (m, 1H), 3.98 (t, J = 7.4 Hz, 2H), 2.54 (s, 3H), 1.93-1.80 (m, 2H), 1.37 (d, J = 6.3 Hz, 6H), 1.02 (t, J = 7.5 Hz, 3H). | 353.4 |
| 3 | 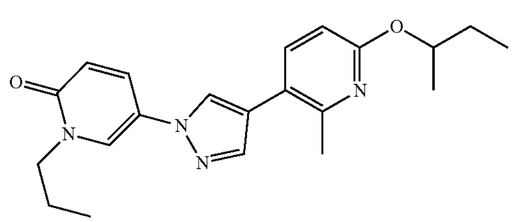 [SMILES: CCCn1cc(-n2cc(-c3ccc(OC(C)CC)nc3C)cn2)ccc1=O] | δ 7.80-7.65 (m, 4H), 7.50 (d, J = 8.7 Hz, 1H), 6.70 (d, J = 9.3 Hz, 1H), 6.58 (d, J = 8.7 Hz, 1H), 5.17-5.13 (m, 1H), 3.98 (t, J = 7.4 Hz, 2H), 2.54 (s, 3H), 1.90-1.64 (m, 4H), 1.33 (d, J = 6.0 Hz, 3H), 1.04-0.96 (m, 6H). | 367.4 |
| 5 | 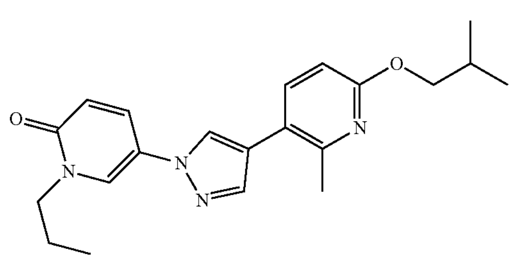 [SMILES: CCCn1cc(-n2cc(-c3ccc(OCC(C)C)nc3C)cn2)ccc1=O] | δ 8.43 (s, 1H), 8.27 (d, J = 3.0 Hz, 1H), 7.98-7.92 (m, 2H), 7.73 (d, J = 8.7 Hz, 1H), 6.69 (d, J = 8.1 Hz, 1H), 6.53 (d, J = 9.9 Hz, 1H), 4.02 (d, J = 6.6 Hz, 2H), 3.90 (t, J = 7.2 Hz, 2H), 2.51 (s, 3H), 2.04-1.99 (m, 1H), 1.73-1.65 (m, 2H), 0.96 (d, J = 6.6 Hz, 6H), 0.88 (t, J = 7.4 Hz, 3H). | 367.4 |

-continued

| Ex No | Structure | ¹H NMR (CDCl₃, 300 MHz) | LC/MS[M + 1] |
|---|---|---|---|
| 6 | 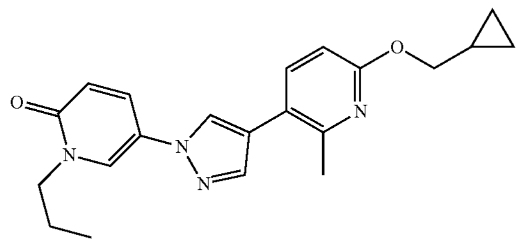 [SMILES: CCCn1cc(-n2cc(-c3ccc(OCC4CC4)nc3C)cn2)ccc1=O] | δ 8.43 (s, 1H), 8.27 (d, J = 3.0 Hz, 1H), 7.98-7.92 (m, 2H), 7.73 (d, J = 8.1 Hz, 1H), 6.70 (d, J = 8.1 Hz, 1H), 6.53 (d, J = 9.3 Hz, 1H), 4.08 (d, J = 6.9 Hz, 2H), 3.90 (t, J = 7.2 Hz, 2H), 2.50 (s, 3H), 1.73-1.65 (m, 2H), 1.25-1.21 (m, 1H), 0.88 (t, J = 7.7 Hz, 3H), 0.56-0.50 (m, 2H), 0.34-0.30 (m, 2H). | 365.4 |
| 7 | 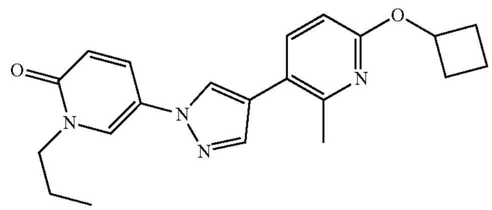 [SMILES: CCCn1cc(-n2cc(-c3ccc(OC4CCC4)nc3C)cn2)ccc1=O] | δ 7.77 (d, J = 2.4 Hz, 1H), 7.73-7.63 (m, 3H), 7.50 (d, J = 5.1 Hz, 1H), 6.69 (d, J = 9.9 Hz, 1H), 6.55 (d, J = 8.1 Hz, 1H), 5.15 (t, J = 7.7 Hz, 1H), 3.97 (t, J = 7.4 Hz, 2H), 2.52 (s, 3H), 2.49-2.43 (m, 2H), 2.20-2.13 (m, 2H), 1.89-1.81 (m, 3H), 1.73-1.64 (m, 1H), 1.01 (t, J = 7.4 Hz, 3H). | 365.3 |
| 9 | 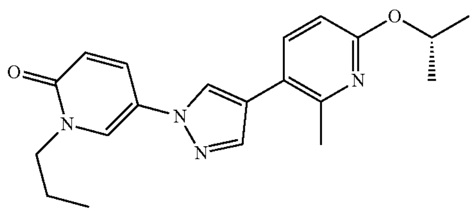 | δ 8.42 (s, 1H), 8.26 (d, J = 2.4 Hz, 1H), 7.97-7.92 (m, 2H), 7.69 (d, J = 8.1 Hz, 1H), 6.63 (d, J = 8.4 Hz, 1H), 6.53 (d, J = 9.3 Hz, 1H), 5.12-5.07 (m, 1H), 3.9 (t, J = 6.9 Hz, 2H), 2.50 (s, 3H), 1.73-1.59 (m, 4H), 1.24 (d, J = 6.6 Hz, 3H), 0.92-0.86 (m, 6H). (DMSO-d6) | 367.4 |
| 10 | 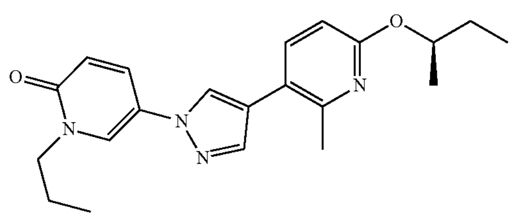 [SMILES: CCCn1cc(-n2cc(-c3ccc(O[C@H](C)CC)nc3C)cn2)ccc1=O] | δ 8.42 (s, 1H), 8.26 (d, J = 3.0 Hz, 1H), 7.97-7.92 (m, 2H), 7.69 (d, J = 8.1 Hz, 1H), 6.63 (d, J = 9.0 Hz, 1H), 6.53 (d, J = 9.9 Hz, 1H), 5.13-5.07 (m, 1H), 3.9 (t, J = 6.9 Hz, 2H), 2.50 (s, 3H), 1.73-1.57 (m, 4H), 1.24 (d, J = 6.6 Hz, 3H), 0.92-0.86 (m, 6H). (DMSO-d6) | 367.4 |
| 11 | 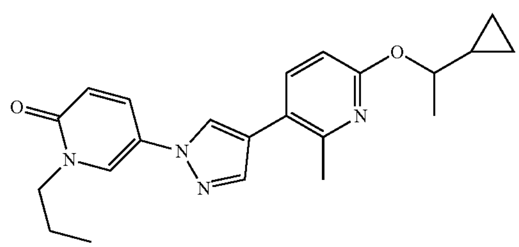 [SMILES: CCCn1cc(-n2cc(-c3ccc(OC(C)C4CC4)nc3C)cn2)ccc1=O] | δ 8.20 (d, J = 3.0 Hz, 2H), 8.03-7.98 (m, 1H), 7.83 (s, 1H), 7.64 (d, J = 8.4 Hz, 1H), 6.67 (d, J = 9.9 Hz, 1H), 6.61 (d, J = 8.1 Hz, 1H), 4.70-4.59 (m, 1H), 4.03 (t, J = 7.4 Hz, 2H), 2.50 (s, 3H), 1.90-1.77 (m, 2H), 1.37 (d, J = 6.0 Hz, 3H), 1.11-1.06 (m, 1H), 0.99 (t, J = 7.2 Hz, 3H), 0.56-0.28 (m, 4H). (CD₃OD) | 379.4 |
| 12 | 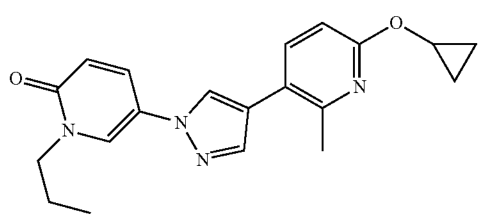 [SMILES: CCCn1cc(-n2cc(-c3ccc(OC4CC4)nc3C)cn2)ccc1=O] | δ 8.44 (s, 1H), 8.28 (d, J = 3.0 Hz, 1H), 7.97-7.94 (m, 2H), 7.75 (d, J = 8.1 Hz, 1H), 6.77 (d, J = 8.1 Hz, 1H), 6.53 (d, J = 9.9 Hz, 1H), 4.21-4.18 (m, 1H), 3.90 (t, J = 7.2 Hz, 2H), 2.52 (s, 3H), 1.73-1.66 (m, 2H), 0.88 (t, J = 7.4 Hz, 3H), 0.76-0.72 (m, 2H), 0.67-0.64 (m, 2H). (DMSO-d6) | 351.5 |
| 13 | 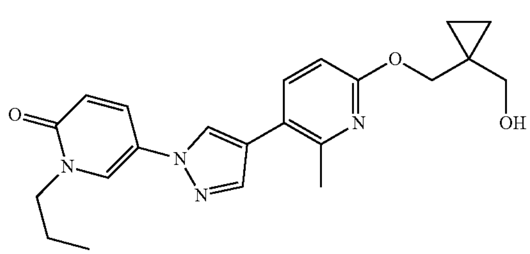 [SMILES: CCCn1cc(-n2cc(-c3ccc(OCC4(CO)CC4)nc3C)cn2)ccc1=O] | δ 7.80-7.65 (m, 4H), 7.56 (d, J = 8.4 Hz, 1H), 6.72-6.67 (m, 2H), 4.43-4.39 (m, 1H), 4.35 (s, 2H), 3.98 (t, J = 7.4 Hz, 2H), 3.42 (d, J = 6.3 Hz, 2H), 2.56 (s, 3H), 1.90-1.82 (m, 2H), 1.02 (t, J = 7.4 Hz, 3H), 0.67-0.58 (m, 4H). | 395.3 |

-continued

| Ex No | Structure | ¹H NMR (CDCl₃, 300 MHz) | LC/MS[M + 1] |
|---|---|---|---|
| 14 | 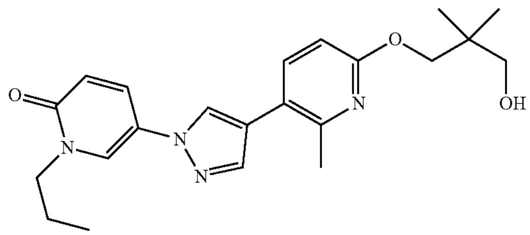 [SMILES: CCCn1cc(-n2cc(-c3ccc(OCC(C)(C)CO)nc3C)cn2)ccc1=O] | δ 7.79-7.65 (m, 4H), 7.56 (d, J = 8.4 Hz, 1H), 6.69 (t, J = 9.3 Hz, 2H), 4.78-4.74 (m, 1H), 4.23 (s, 2H), 3.98 (t, J = 7.2 Hz, 2H), 3.26 (d, J = 6.3 Hz, 2H), 2.54 (s, 3H), 1.90-1.82 (m, 2H), 1.04-1.01 (m, 9H). | 397.3 |
| 15 | 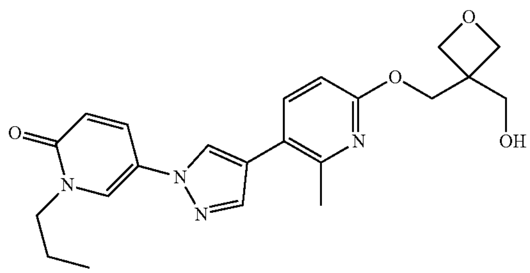 [SMILES: CCCn1cc(-n2cc(-c3ccc(OCC4(CO)COC4)nc3C)cn2)ccc1=O] | δ 7.80 (d, J = 2.1 Hz, 1H), 7.80 (d, J = 1.8 Hz, 2H), 7.64 (dd, J = 9.0 & 2.4 Hz, 1H), 7.57 (d, J = 8.7 Hz, 1H), 6.69 (t, J = 9.9 Hz, 2H), 4.80 (bs, 2H), 4.60-4.51 (m, 5H), 3.98 (t, J = 7.2 Hz, 2H), 3.83 (d, J = 6.9 Hz, 2H), 2.54 (s, 3H), 1.90-1.82 (m, 2H), 1.02 (t, J = 7.4 Hz, 3H). | 411.3 |
| 16 | 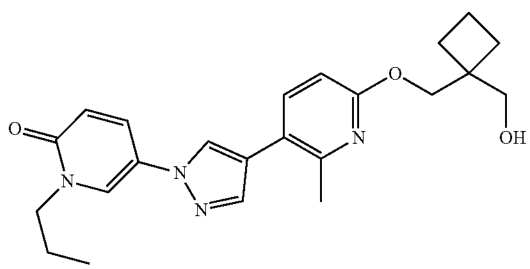 [SMILES: CCCn1cc(-n2cc(-c3ccc(OCC4(CO)CCC4)nc3C)cn2)ccc1=O] | δ 7.78 (d, J = 3 Hz, 1H), 7.71 (d, J = 5.4 Hz, 2H), 7.65 (dd, J = 9.6 Hz, 2.7 Hz, 1H), 7.54 (d, J = 8.7 Hz, 1H), 6.71-6.63 (m, 2H), 4.54 (t, J = 7.1 Hz, 1H), 4.49 (s, 2H), 3.97 (t, J = 7.4 Hz, 2H), 3.53 (d, J = 7.2 Hz, 2H), 2.52 (s, 3H), 2.02-1.81 (m, 8H), 1.00 (t, J = 7.4 Hz, 3H). | 409.0 |
| 17 | 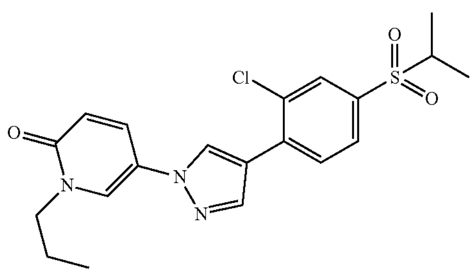 | δ 8.22 (s, 1H), 8.05 (s, 1H), 8.00 (s, 1H), 7.83-7.79 (m, 2H), 7.72-7.66 (m, 2H), 6.71 (d, J = 9.9 Hz, 1H), 3.99 (t, J = 7.2 Hz, 2H), 3.29-3.20 (m, 1H), 1.93-1.81 (m, 2H), 1.36 (d, J = 6.9 Hz, 6H), 1.03 (t, J = 7.4 Hz, 3H). | 420.7 |
| 18 | 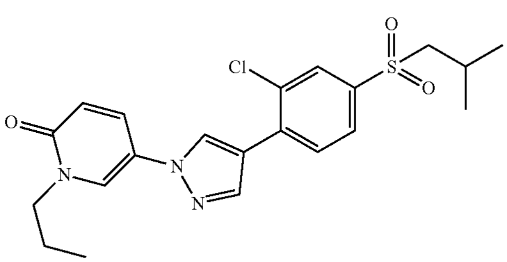 [SMILES: CCCn1cc(-n2cc(-c3ccc(S(=O)(=O)CC(C)C)cc3Cl)cn2)ccc1=O] | δ 8.22 (s, 1H), 8.04 (s, 2H), 7.85-7.82 (m, 2H), 7.72-7.67 (m, 2H), 6.71 (d, J = 9.9 Hz, 1H), 3.99 (t, J = 1.2 Hz, 2H), 3.04 (d, J = 6.3 Hz, 2H), 2.32-2.28 (m, 1H), 1.90-1.83 (m, 2H), 1.11 (d, J = 6.3 Hz, 6H), 1.03 (t, J = 7.4 Hz, 3H). | 434.9 |
| 19 | 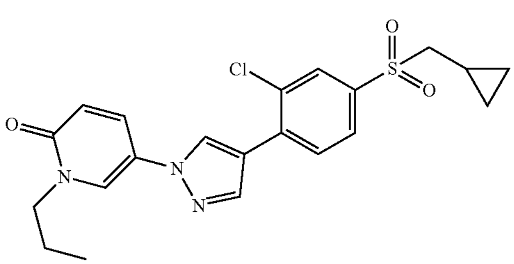 [SMILES: CCCn1cc(-n2cc(-c3ccc(S(=O)(=O)CC4CC4)cc3Cl)cn2)ccc1=O] | δ 8.24 (s, 1H), 8.06 (s, 2H), 7.88-7.82 (m, 2H), 7.72-7.66 (m, 2H), 6.71 (d, J = 9.9 Hz, 1H), 3.99 (t, J = 7.2 Hz, 2H), 3.08 (d, J = 6.9 Hz, 2H), 1.90-1.83 (m, 2H), 1.03 (t, J = 7.4 Hz, 4H), 0.67-0.61 (m, 2H), 0.25-0.19 (m, 2H). | 432.8 |

| Ex No | Structure | ¹H NMR (CDCl₃, 300 MHz) | LC/MS[M + 1] |
|---|---|---|---|
| 20 | 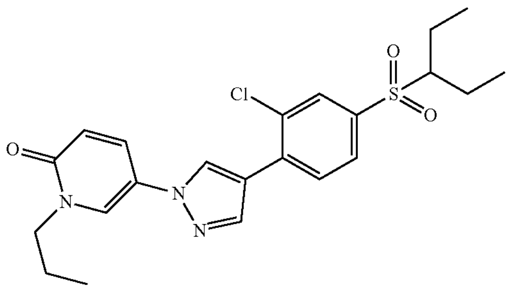 [SMILES: CCCn1cc(-n2cc(-c3ccc(S(=O)(=O)C(CC)CC)cc3Cl)cn2)ccc1=O] | δ 8.22 (s, 1H), 8.05 (s, 1H), 8.00 (s, 1H), 7.82-7.79 (m, 2H), 7.71-7.67 (m, 2H), 6.72 (d, J = 9.3 Hz, 1H), 3.99 (t, J = 7.2 Hz, 2H), 2.88-2.84 (m, 1H), 1.88-1.68 (m, 6H), 1.08-1.00 (m, 9H) | 448.7 |
| 21 | 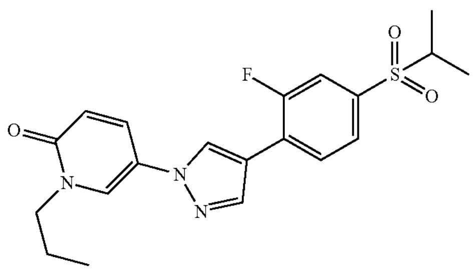 [SMILES: CCCn1cc(-n2cc(-c3ccc(S(=O)(=O)C(C)C)cc3F)cn2)ccc1=O] | δ 8.19 (s, 1H), 8.11 (s, 1H), 7.83-7.68 (m, 5H), 6.72 (d, J = 9.6 Hz, 1H), 3.99 (t, J = 7.2 Hz, 2H), 3.27-3.22 (m, 1H), 1.91-1.83 (m, 2H), 1.35 (d, J = 7.2 Hz, 6H), 1.03 (t, J = 7.4 Hz, 3H). | 404.5 |
| 22 | 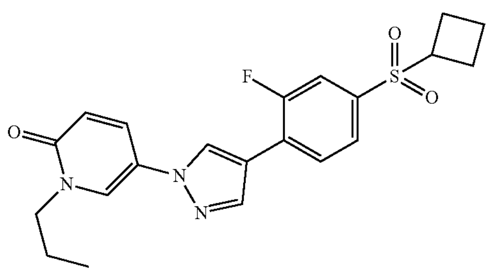 | δ 8.18 (d, J = 2.4 Hz, 1H), 8.10 (s, 1H), 7.83-7.66 (m, 5H), 6.72 (d, J = 9.3 Hz, 1H), 3.99 (t, J = 7.2 Hz, 2H), 3.88-3.82 (m, 1H), 2.65-2.54 (m, 2H), 2.27-1.83 (m, 6H), 1.03 (t, J = 7.4 Hz, 3H). | 416.1 |
| 23 | 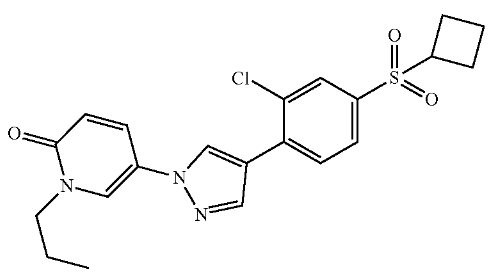 [SMILES: CCCn1cc(-n2cc(-c3ccc(S(=O)(=O)C4CCC4)cc3F)cn2)ccc1=O] | δ 8.21 (s, 1H), 8.04 (s, 1H), 7.99 (d, J = 1.2 Hz, 1H), 7.83-7.66 (m, 4H), 6.71 (d, J = 9.3 Hz, 1H), 3.99 (t, J = 7.2 Hz, 2H), 3.88-3.83 (m, 1H), 2.65-2.54 (m, 2H), 2.27-1.83 (m, 6H), 1.02 (t, J = 7.4 Hz, 3H). | 432.1 |
| 64 | 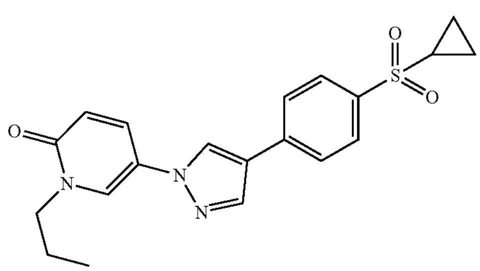 [SMILES: CCCn1cc(-n2cc(-c3ccc(S(=O)(=O)C4CC4)cc3)cn2)ccc1=O] | δ 8.02 (s, 2H), 7.93 (d, J = 9.0 Hz, 2H), 7.81-7.68 (m, 4H), 6.72 (d, J = 9.9 Hz, 1H), 3.99 (t, J = 7.2 Hz, 2H), 2.52-2.48 (m, 1H), 1.90-1.83 (m, 2H), 1.42-1.38 (m, 2H), 1.08-1.00 (m, 5H). | 384.6 |

-continued

| Ex No | Structure | ¹H NMR (CDCl₃, 300 MHz) | LC/MS[M + 1] |
|---|---|---|---|
| 24 | 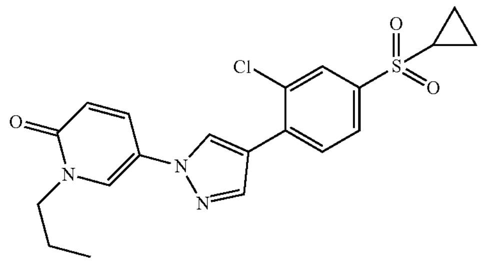 [SMILES: CCCn1cc(-n2cc(-c3ccc(S(=O)(=O)C4CC4)cc3Cl)cn2)ccc1=O] | δ 8.21 (s, 1H), 8.03 (s, 1H), 8.01 (s, 1H), 7.81 (d, J = 3.0 Hz, 2H), 7.71-7.66 (m, 2H), 6.71 (d, J = 9.9 Hz, 1H), 3.98 (t, J = 12 Hz, 2H), 2.52-2.48 (m, 1H), 1.89-1.82 (m, 2H), 1.40-1.36 (m, 2H), 1.10-0.99 (m, 5H). | 418.7 |
| 25 | 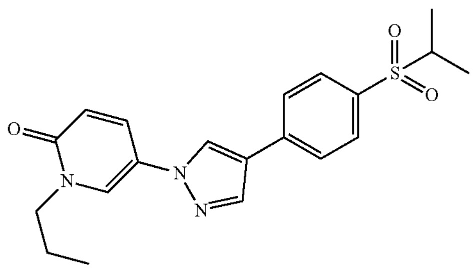 [SMILES: CCCn1cc(-n2cc(-c3ccc(S(=O)(=O)C(C)C)cc3)cn2)ccc1=O] | δ 8.92 (s, 1H), 8.32 (s, 1H), 8.30 (d, J = 3.0 Hz, 1H), 7.97-7.91 (m, 3H), 7.86-7.83 (m, 2H), 6.55 (d, J = 9.9 Hz, 1H), 3.90 (t, J = 7.4 Hz, 2H), 3.44-3.38 (m, 1H), 1.74-1.66 (m, 2H), 1.15 (d, J = 6.3 Hz, 6H), 0.88 (t, J = 7.4 Hz, 3H). (DMSO-d6) | 386.7 |
| 78 | 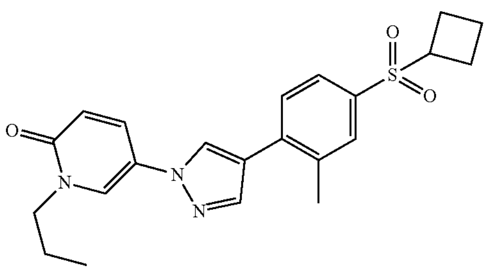 [SMILES: CCCn1cc(-n2cc(-c3ccc(S(=O)(=O)C4CCC4)cc3C)cn2)ccc1=O] | δ 7.86 (s, 2H), 7.83-7.66 (m, 4H), 7.53 (d, J = 5.1 Hz, 1H), 6.71 (d, J = 9.9 Hz, 1H), 3.99 (t, J = 7.5 Hz, 2H), 3.87-3.82 (m, 1H), 2.64-2.57 (m, 2H), 2.53 (s, 3H), 2.25-1.83 (m, 6H), 1.02 (t, J = 7.4 Hz, 3H). | 412.3 |
| 79 | 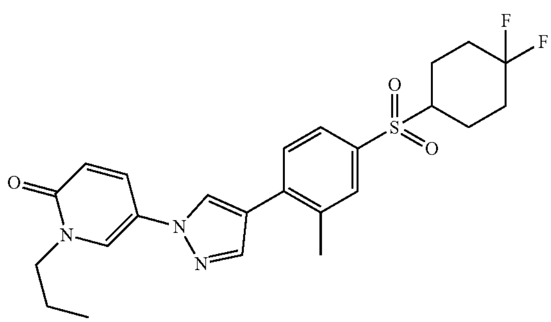 [SMILES: CCCn1cc(-n2cc(-c3ccc(S(=O)(=O)C4CCC(F)(F)CC4)cc3C)cn2)ccc1=O] | δ 7.87-7.65 (m, 6H), 7.57 (d, J = 8.1 Hz, 1H), 6.71 (d, J = 9.3 Hz, 1H), 3.995 (t, J = 7.2 Hz, 2H), 3.04-2.96 (m, 1H), 2.55 (s, 3H), 2.29-1.67 (m, 10H), 1.03 (t, J = 7.4 Hz, 3H). | 476.4 |
| 80 | 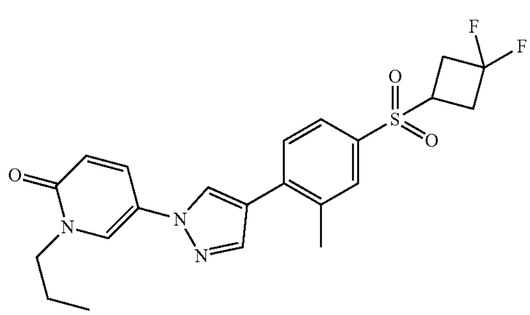 [SMILES: CCCn1cc(-n2cc(-c3ccc(S(=O)(=O)C4CC(F)(F)C4)cc3C)cn2)ccc1=O] | δ 7.86-7.65 (m, 6H), 7.57 (d, J = 8.1 Hz, 1H), 6.71 (d, J = 9.3 Hz, 1H), 3.99 (t, J = 7.5 Hz, 2H), 3.68-3.63 (m, 1H), 3.15-2.76 (m, 4H), 2.55 (s, 3H), 1.91-1.83 (m, 2H), 1.02 (t, J = 7.4 Hz, 3H). | 448.3 |

-continued

| Ex No | Structure | ¹H NMR (CDCl₃, 300 MHz) | LC/MS[M + 1] |
|---|---|---|---|
| 87 | 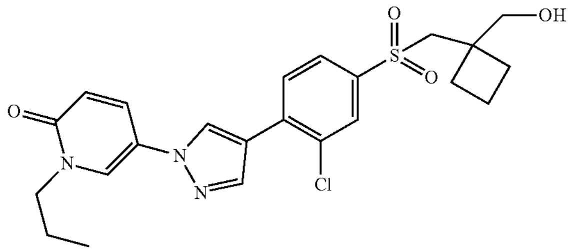 [SMILES: CCCn1cc(-n2cc(-c3ccc(S(=O)(=O)CC4(CO)CCC4)cc3Cl)cn2)ccc1=O] | δ 8.22 (s, 1H), 8.04 (d, J = 2.4 Hz, 2H), 7.86-7.70 (m, 4H), 6.70 (d, J = 9.3 Hz, 1H), 4.03-4.00 (m, 4H), 3.42 (s, 2H), 2.01-1.83 (m, 8H), 1.03 (t, J = 7.4 Hz, 3H). | 476.4 |
| 4 | 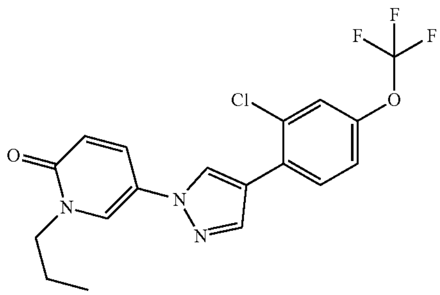 [SMILES: CCCn1cc(-n2cc(-c3ccc(OC(F)(F)F)cc3Cl)cn2)ccc1=O] | δ 8.08 (s, 1H), 7.95 (s, 1H), 7.81 (d, J = 3.0 Hz, 1H), 7.68 (dd, J = 9.9, 3.0 Hz, 1H), 7.52 (d, J = 8.4 Hz, 1H), 7.39 (s, 1H), 7.21-7.19 (m, 1H), 6.71 (d, J = 9.9 Hz, 1H), 3.99 (t, J = 7.5 Hz, 2H), 1.90-1.83 (m, 2H), 1.02 (t, J = 7.7 Hz, 3H) | 398.5 |
| 26 | 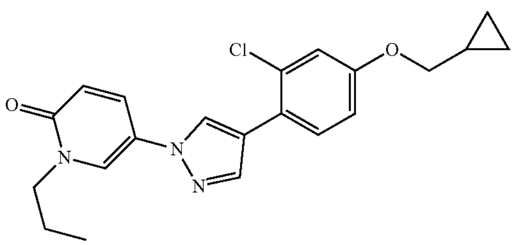 [SMILES: CCCn1cc(-n2cc(-c3ccc(OCC4CC4)cc3Cl)cn2)ccc1=O] | δ 8.00 (s, 1H), 7.89 (s, 1H), 7.78 (d, J = 3.0 Hz, 1H), 7.67 (dd, J = 9.6, 2.7 Hz, 1H), 7.37 (d, J = 8.7 Hz, 1H), 7.02 (d, J = 2.4 Hz, 1H), 6.88 (dd, J = 8.7, 2.4 Hz, 1H), 6.68 (d, J = 9.9 Hz, 1H), 3.97 (t, J = 7.7 Hz, 2H), 3.82 (d, J = 6.6 Hz, 1H), 1.89-1.79 (m, 2H), 1.31-1.26 (m, 1H), 1.01 (t, J = 7.7 Hz, 3H), 0.70-0.64 (m, 2H), 0.39-0.34 (m, 2H). | 384.6 |
| 8 | 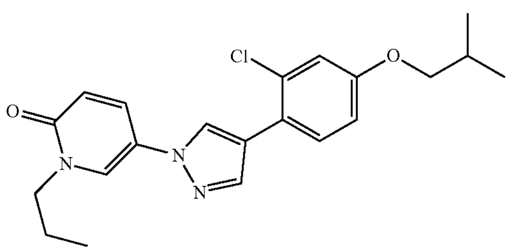 [SMILES: CCCn1cc(-n2cc(-c3ccc(OCC(C)C)cc3Cl)cn2)ccc1=O] | δ 8.55 (s, 1H), 8.29 (d, J = 3.0 Hz, 1H), 8.01 (s, 1H), 7.98-7.93 (m, 1H), 7.54 (d, J = 8.1 Hz, 1H), 7.10 (d, J = 2.4 Hz, 1H), 7.00-6.96 (m, 1H), 6.53 (d, J = 9.3 Hz, 1H), 3.89 (t, J = 7.2 Hz, 2H), 3.78 (d, J = 6.3 Hz, 2H), 2.06-1.96 (m, 1H), 1.73-1.65 (m, 2H), 0.96 (d, J = 6.9 Hz, 6H), 0.88 (t, J = 7.4 Hz, 3H). (DMSO-d6) | 386.6 |
| 27 | 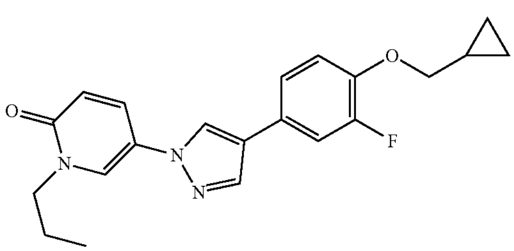 [SMILES: CCCn1cc(-n2cc(-c3ccc(OCC4CC4)c(F)c3)cn2)ccc1=O] | δ 8.67 (s, 1H), 8.23 (d, J = 3.0 Hz, 1H), 8.12 (s, 1H), 7.94-7.89 (m, 1H), 7.54-7.49 (m, 1H), 7.39 (d, J = 9.0 Hz, 1H), 7.15 (t, J = 8.9 Hz, 1H), 6.54 (d, J = 9.9 Hz, 1H), 3.90 (t, J = 5.9 Hz, 4H), 1.73-1.65 (m, 2H), 1.25-1.22 (m, 1H), 0.88 (t, J = 7.4 Hz, 3H), 0.60-0.54 (m, 2H), 0.34-0.31 (m, 2H). (DMSO-d6) | 368.3 |
| 28 | 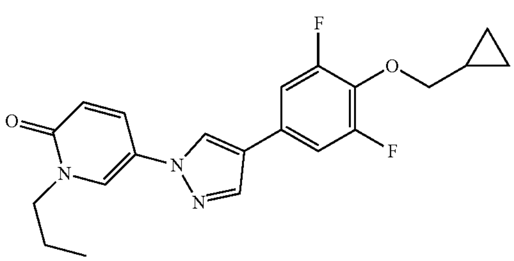 [SMILES: CCCn1cc(-n2cc(-c3cc(F)c(OCC4CC4)c(F)c3)cn2)ccc1=O] | δ 8.76 (s, 1H), 8.22 (t, J = 3.5 Hz, 2H), 7.91-7.87 (m, 1H), 7.46 (d, J = 9.3 Hz, 2H), 6.54 (d, J = 9.6 Hz, 1H), 3.90 (t, J = 8.7 Hz, 4H), 1.70-1.65 (m, 2H), 1.18-1.16 (m, 1H), 0.88 (t, J = 7.4 Hz, 3H), 0.55-0.48 (m, 2H), 0.24 (d, J = 6.0 Hz, 2H). (DMSO-d6) | 386.4 |

| Ex No | Structure | ¹H NMR (CDCl₃, 300 MHz) | LC/MS[M + 1] |
|---|---|---|---|
| 29 | 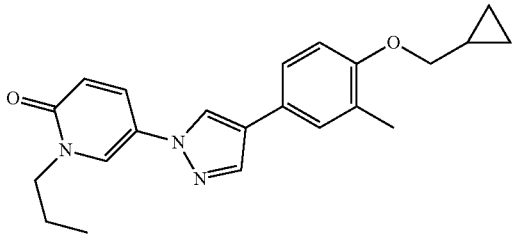 | δ 8.58 (s, 1H), 8.24 (d, J = 3.0 Hz, 1H), 8.04 (s, 1H), 7.96-7.91 (m, 1H), 7.43 (s, 1H), 7.40 (d, J = 8.1 Hz, 1H), 6.90 (d, J = 8.1 Hz, 1H), 6.52 (d, J = 9.9 Hz, 1H), 3.89 (t, J = 5.7 Hz, 2H), 3.83 (d, J = 6.3 Hz, 2H), 2.19 (s, 3H), 1.73-1.66 (m, 2H), 1.23-1.21 (m, 1H), 0.88 (t, J = 7.4 Hz, 3H), 0.59-0.54 (m, 2H), 0.35-0.32 (m, 2H). (DMSO-d6) | 364.6 |
| 30 | 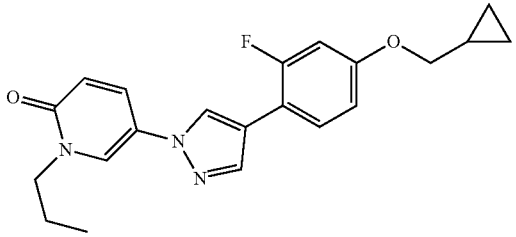 | δ 8.54 (s, 1H), 8.29 (d, J = 3.0 Hz, 1H), 8.06 (s, 1H), 7.97-7.93 (m, 1H), 7.65 (t, J = 8.9 Hz, 1H), 6.92-6.82 (m, 2H), 6.52 (d, J = 9.3 Hz, 1H), 3.92-3.83 (m, 4H), 1.73-1.66 (m, 2H), 1.23-1.21 (s, 1H), 0.88 (t, 7.4 Hz, 3H), 0.56 (d, J = 6.3 Hz, 2H), 0.31 (d, J = 5.7 Hz, 2H). (DMSO-d6) | 368.5 |
| 31 | 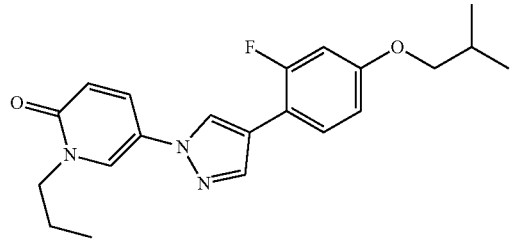 [SMILES: CCCn1cc(-n2cc(-c3ccc(OCC(C)C)cc3F)cn2)ccc1=O] | δ 8.55 (s, 1H), 8.29 (d, J = 2.7 Hz, 1H), 8.06 (s, 1H), 7.97-7.93 (m, 1H), 7.65 (t, J = 8.9 Hz, 1H), 6.93-6.82 (m, 2H), 6.52 (d, J = 9.9 Hz, 1H), 3.89 (t, J = 7.2 Hz, 2H), 3.77 (d, J = 6.6 Hz, 2H), 2.03-1.98 (m, 1H), 1.73-1.65 (m, 2H), 0.96 (d, J = 6.3 Hz, 6H), 0.88 (t, J = 7.4 Hz, 3H). (DMSO-d6) | 370.4 |
| 32 | 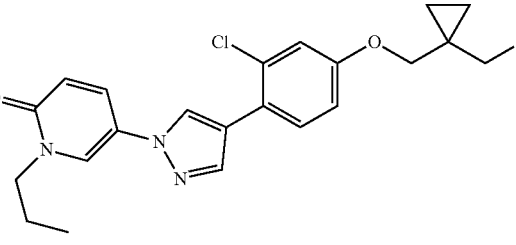 | δ 8.01 (s, 1H), 7.90 (s, 1H), 7.78 (d, J =3.0 Hz, 1H), 7.67 (dd, J = 9.9 and 3.0 Hz, 1H), 7.39 (d, J = 9.0 Hz, 1H), 7.04 (d, J = 2.1 Hz, 1H), 6.88 (dd, J = 8.7 and 2.4 Hz, 1H), 6.69 (d, J = 9.9 Hz, 1H), 4.00-3.97 (m, 4H), 3.66 (bs, 2H), 1.89-1.82 (m, 2H), 1.02 (t, J = 7.4 Hz, 3H), 0.67 (s, 4H). | 414.6 |
| 33 | 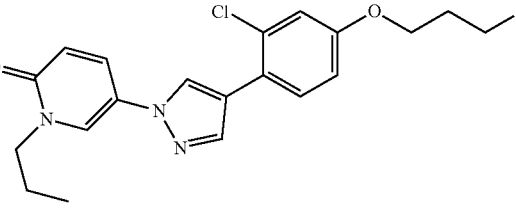 | δ 8.02 (s, 1H), 7.91 (s, 1H), 7.79 (d, J = 2.7 Hz, 1H), 7.68 (dd, J = 9.3 and 2.7 Hz, 1H), 7.39 (d, J = 9.0 Hz, 1H), 7.05 (d, J = 2.4 Hz, 1H), 6.88 (dd, J = 8.7 and 2.4 Hz, 1H), 6.69 (d, J = 9.3 Hz, 1H), 4.16 (t, J = 6.0 Hz, 2H), 3.98 (t, J = 7.4 Hz, 2H), 3.89 (bs, 2H), 2.10-2.06 (m, 2H), 1.90-1.82 (m, 2H), 1.02 (t, J = 7.4 Hz, 3H). | 388.7 |
| 34 | 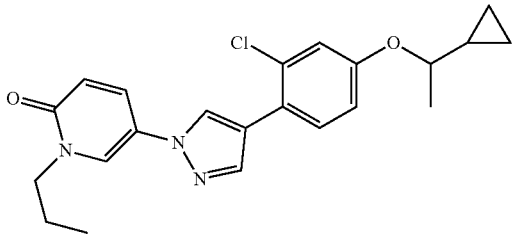 [SMILES: CCCn1cc(-n2cc(-c3ccc(OC(C)C4CC4)cc3Cl)cn2)ccc1=O] | δ 8.01 (s, 1H), 7.90 (s, 1H), 7.79 (d, J = 2.1 Hz, 1H), 7.68 (dd, J = 9.9 and 2.7 Hz, 1H), 7.37 (d, J = 9.0 Hz, 1H), 7.02 (bs, 1H), 6.86 (d, J = 8.1 Hz, 1H), 6.69 (d, J = 9.9 Hz, 1H), 3.98 (t, J = 7.7 Hz, 2H), 3.85 (t, J = 6.5 Hz, 1H), 1.90-1.82 (m, 2H), 1.40 (d, J = 6.3 Hz, 3H), 1.16-1.13 (m, 1H), 1.02 (t, J = 7.4 Hz, 3H), 0.61-0.58 (m, 2H), 0.40-0.31 (m, 2H). | 398.7 |

-continued

| Ex No | Structure | ¹H NMR (CDCl₃, 300 MHz) | LC/MS[M + 1] |
|---|---|---|---|
| 35 | 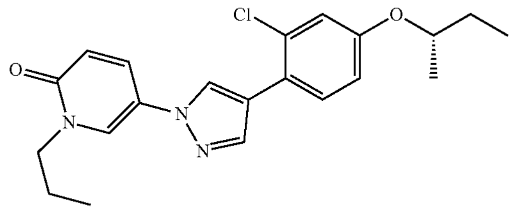 [SMILES: CCCn1cc(-n2cc(-c3ccc(O[C@@H](C)CC)cc3Cl)cn2)ccc1=O] | δ 7.98 (s, 1H), 7.86 (s, 1H), 7.76 (s, 1H), 7.65 (d, J = 9.3 Hz, 1H), 7.33 (d, J = 8.7 Hz, 1H), 6.97 (s, 1H), 6.80 (d, J = 7.8 Hz, 1H), 6.63 (d, J = 9.6 Hz, 1H), 4.31-4.25 (m, 1H), 3.93 (t, J = 7.2 Hz, 2H), 1.84-1.56 (m, 4H), 1.28 (d, J = 5.7 Hz, 3H), 0.98-0.96 (m, 6H). | 386.8 |
| 36 | 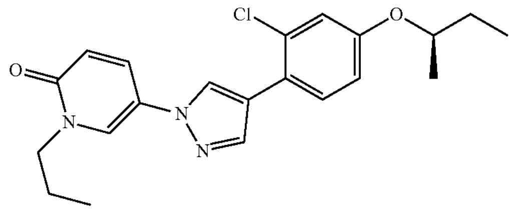 [SMILES: CCCn1cc(-n2cc(-c3ccc(O[C@H](C)CC)cc3Cl)cn2)ccc1=O] | δ 7.99 (s, 1H), 7.88 (s, 1H), 7.78 (d, J = 2.4 Hz, 1H), 7.66 (dd, J = 9.3, 2.4 Hz, 1H), 7.35 (d, J = 8.7 Hz, 1H), 6.99 (d, J = 1.8 Hz, 1H), 6.82 (dd, J = 8.4, 2.1 Hz, 1H), 6.66 (d, J = 9.3 Hz, 1H), 4.32-4.27 (m, 1H), 3.96 (t, J = 7.5 Hz, 2H), 1.87-1.61 (m, 4H), 1.30 (d, J = 6. Hz, 3H), 1.02-0.95 (m, 6H). | 386.8 |
| 37 | 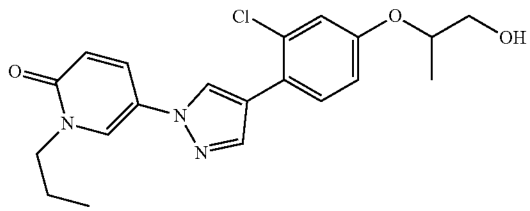 [SMILES: CCCn1cc(-n2cc(-c3ccc(OC(C)CO)cc3Cl)cn2)ccc1=O] | δ 8.01 (s, 1H), 7.90 (s, 1H), 7.78 (d, J = 2.7 Hz, 1H), 7.67 (dd, J = 9.9, 3.0 Hz, 1H), 7.39 (d, J = 9.0 Hz, 1H), 7.06 (d, J = 2.4 Hz, 1H), 6.89 (dd, J = 8.7, 2.4 Hz, 1H), 6.68 (d, J = 8.7 Hz, 1H), 4.55-4.49 (m, 1H), 3.97 (t, J = 7.7 H, 2H), 3.77-3.76 (m, 2H), 2.11 (t, J = 6.4 Hz, 1H), 1.94-1.81 (m, 3H), 1.31 (d, J = 6.3 Hz, 3H), 1.01 (t, J = 7.4 Hz, 3H). | 388.7 |
| 38 | 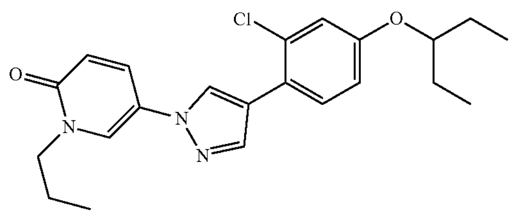 [SMILES: CCCn1cc(-n2cc(-c3ccc(OC(CC)CC)cc3Cl)cn2)ccc1=O] | δ 8.01 (s, 1H), 7.90 (s, 1H), 7.79 (d, J = 3.0 Hz, 1H), 7.68 (dd, J = 10.2, 3.0 Hz, 1H), 7.37 (d, J = 8.7 Hz, 1H), 7.02 (d, J = 2.4 Hz, 1H), 6.86 (dd, J = 8.7, 3.0 Hz, 1H), 6.70 (d, J = 9.9 Hz, 1H), 4.18-4.11 (m, 1H), 3.98 (t, J = 7.2 Hz, 2H), 1.90-1.76 (m, 2H), 1.73-1.66 (m, 4H), 1.04-0.96 (m, 9H). | 400.8 |
| 39 | 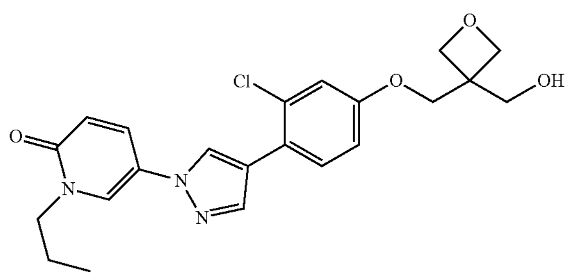 [SMILES: CCCn1cc(-n2cc(-c3ccc(OCC4(CO)COC4)cc3Cl)cn2)ccc1=O] | δ 8.02 (s, 1H), 7.91 (s, 1H), 7.79 (d, J = 2.4 Hz, 1H), 7.67 (dd, J = 9.9 & 3.0 Hz, 1H), 7.41 (d, J = 8.1 Hz, 1H), 7.08 (d, J = 1.5 Hz, 1H), 6.91 (d, J = 9.1 Hz, 1H), 6.68 (d, J = 9.9 Hz, 1H), 4.60 (bs, 4H), 4.30 (s, 2H), 4.06 (d, J = 4.8 Hz, 2H), 3.97 (t, J = 7.2 Hz, 2H), 1.89-1.82 (m, 2H), 1.02 (t, J = 7.4 Hz, 3H). | 430.2 |
| 40 | 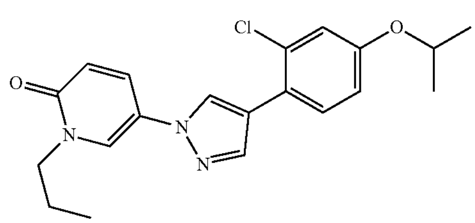 [SMILES: CCCn1cc(-n2cc(-c3ccc(OC(C)C)cc3Cl)cn2)ccc1=O] | δ 8.54 (s, 1H), 8.28 (d, J = 2.4 Hz, 1H), 8.00 (s, 1H), 7.97-7.93 (m, 1H), 7.52 (d, J = 8.7 Hz, 1H), 7.07 (d, J = 2.4 Hz, 1H), 6.98-6.94 (m, 1H), 6.53 (d, J = 6.9 Hz, 1H), 4.69-4.65 (m, 1H), 3.89 (t, J = 7.2 Hz, 2H), 1.73-1.65 (m, 2H), 1.25 (d, J = 6.0 Hz, 6H), 0.87 (t, J = 7.4 Hz, 3H). (DMSO-d6) | 372.7 |
| 41 | 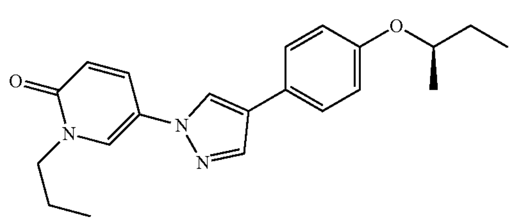 [SMILES: CCCn1cc(-n2cc(-c3ccc(O[C@H](C)CC)cc3)cn2)ccc1=O] | δ 7.86 (s, 1H), 7.82 (s, 1H), 7.76 (d, J = 3.0 Hz, 1H), 7.65 (dd, J = 9.6, 2.7 Hz, 1H), 7.41 (d, J = 8.1 Hz, 2 H), 6.91 (d, J = 8.7 Hz, 2H), 6.67 (d, J = 9.9 Hz, 1H), 4.34-4.28 (m, 1H), 3.96 (t, J = 7.5 Hz, 2H), 1.90-1.58 (m, 4H), 1.30 (d, J = 6.0 Hz, 3H), 1.02-0.96 (m, 6H). | 352.4 |

| Ex No | Structure | ¹H NMR (CDCl₃, 300 MHz) | LC/MS[M + 1] |
|---|---|---|---|
| 42 | 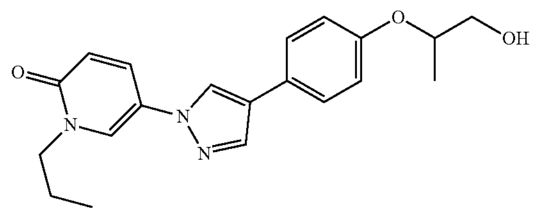 [SMILES: CCCn1cc(-n2cc(-c3ccc(OC(C)CO)cc3)cn2)ccc1=O] | δ 7.87 (s, 1H), 7.83 (s, 1H), 7.76 (d, J = 3.0 Hz, 1H), 7.66 (dd, J = 9.6, 2.7 Hz, 1H), 7.42 (d, J = 9.0 Hz, 2H), 6.96 (d, J = 9.0 Hz, 2H), 6.67 (d, J = 9.9 Hz, 1H), 4.55-4.50 (m, 1H), 3.96 (t, J = 7.4 Hz, 2H), 3.77-3.70 (m, 2H), 1.90-1.78 (m, 2H), 1.70 (bs, 1H), 1.30 (d, J = 6.0 Hz, 3H), 1.00 (t, J = 7.2 Hz, 3H) | 354.5 |
| 43 | 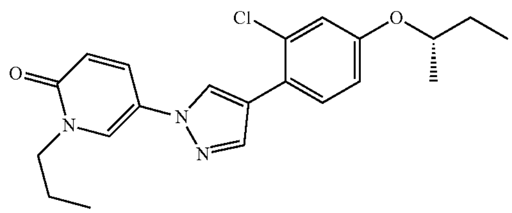 [SMILES: CCCn1cc(-n2cc(-c3ccc(O[C@@H](C)CC)cc3Cl)cn2)ccc1=O] | δ 7.86 (s, 1H, 7.83 (s, 1H), 7.76 (d, J = 3.0 Hz, 1H), 7.66 (dd, J = 9.3, 3.0 Hz, 1H), 7.42 (d, J = 9.0 Hz, 2H), 6.92 (d, J = 9.0 Hz, 2H), 6.68 (d, J = 9.6 Hz, 1H), 4.37-4.27 (m, 1H), 3.96 (t, J = 7.6 Hz, 2H), 1.90-1.56 (m, 4H), 1.31 (d, J = 5.7 Hz, 3H), 1.02-0.94 (m, 6H). | 352.4 |
| 44 | 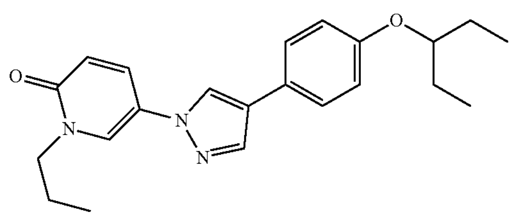 [SMILES: CCCn1cc(-n2cc(-c3ccc(OC(CC)CC)cc3)cn2)ccc1=O] | δ 7.87 (s, 1H), 7.83 (s, 1H), 7.77 (d, J = 3.0 Hz, 1H), 7.67 (dd, J = 9.6, 2.4 Hz, 1H), 7.43 (d, J = 6.3 Hz, 2H), 6.93 (d, J = 9.0 Hz, 2H), 6.69 (d, J = 9.9 Hz, 1H), 4.18-4.11 (m, 1H), 3.98 (t, J = 7.2 Hz, 2H), 1.89-1.75 (m, 2H), 1.73-1.66 (m,4H), 1.04-0.96 (m, 9H). | 366.4 |
| 81 | 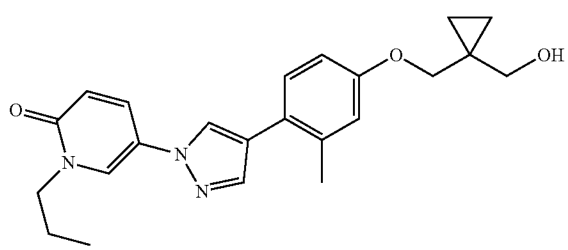 [SMILES: CCCn1cc(-n2cc(-c3ccc(OCC4(CO)CC4)cc3C)cn2)ccc1=O] | δ 7.80 (d, J = 2.7 Hz, 1H), 7.74 (s, 1H), 7.70-7.65 (m, 2H), 7.25 (s, 1H), 6.85 (d, J = 2.4 Hz, 1H), 6.79 (dd, J = 9.1 and 2.4 Hz, 1H), 6.69 (d, J = 9.3 Hz, 1H), 4.01-3.96 (m, 4H), 3.67 (d, J = 5.7 Hz, 2H), 2.39 (s, 3H), 2.00-1.82 (m, 3H), 1.02 (t, J = 7.4 Hz, 3H), 0.67 (s, 4H). | 394.3 |
| 82 | 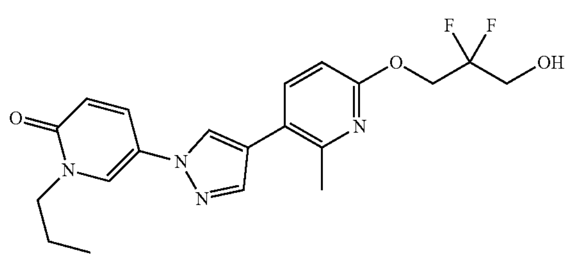 [SMILES: CCCn1cc(-n2cc(-c3ccc(OCC(F)(F)CO)nc3C)cn2)ccc1=O] | δ 7.81-7.62 (m, 5H), 6.78 (d, J = 8.7 Hz, 1H), 6.70 (d, J = 9.9 Hz, 1H), 4.71 (t, J = 7.2 Hz, 2H), 3.99 (t, J = 7.5 Hz, 2H), 3.78 (t, J = 12.3 Hz, 2H), 2.57 (s, 3H), 1.90-1.83 (m, 2H), 1.02 (t, J = 7.4 Hz, 3H). | 405.3 |

Example 45: 5-(4-(2-chloro-4-methoxyphenyl)-1H-pyrazol-1-yl)-1-propylpyridin-2(1H)-one

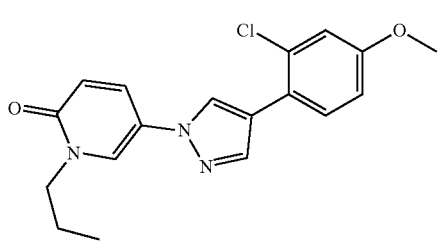 [SMILES: CCCn1cc(-n2cc(-c3ccc(OC)cc3Cl)cn2)ccc1=O]

A micro wave vial was charged with 5-(4-bromo-1H-pyrazol-1-yl)-1-propylpyridin-2(1H)-one (200 mg, 0.7 mmol), 2-chloro-4-methoxyphenylboronic acid (0.26 g, 0.9 mmol), potassium carbonate (0.30 g, 2.1 mmol) and 1,4-dioxan (12 mL) and water (3 mL) and the flask was degassed and flushed with argon. PdCl₂(dppf) (0.050 g, 0.1 mmol) was added and the reaction flask was again degassed and flushed with argon. The reaction mixture was then heated to 100° C. in a microwave for 2 hours. The reaction was cooled to room temperature and quenched with saturated NaHCO₃ and extracted with ethyl acetate (3×50 mL). The combined organics were washed with water, brine and dried over MgSO₄. The solvents were evaporated to dryness and the residue purified by flash chromatography (12 g silica gel, 0-40% ethyl acetate in hexanes) and again by reverse phase HPLC to afford the product as colorless oil (60 mg, 25%).

LC/MS: 344.5 [M+1]+, 1H NMR (300 MHz, CDCl3): δ 8.00 (s, 1H), 8.05 (s, 1H), 7.89 (s, 1H), 7.78 (d, J=2.7 Hz, 1H), 7.67 (dd, J=9.9 and 3.0 Hz, 1H), 7.39 (d, J=9.0 Hz, 1H), 7.02 (d, J=3.0 Hz, 1H0, 6.86 (dd, J=8.1 and 3.0 Hz, 1H), 6.69 (d, J=9.3 Hz, 1H), 3.97 (t, J=7.2 Hz, 2H), 3.83 (s, 3H), 1.88-1.81 (m, 2H), 1.01 (t, J=6.9 Hz, 3H).

Example 46: 5-(4-(4-methoxyphenyl)-1H-pyrazol-1-yl)-1-propylpyridin-2(1H)-one

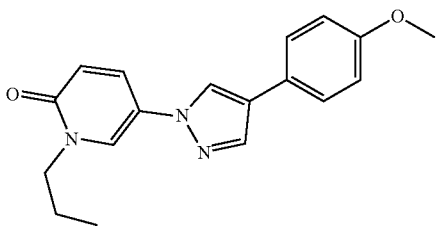 [SMILES: CCCn1cc(-n2cc(-c3ccc(OC)cc3)cn2)ccc1=O]

The above compound was prepared as described in Example 45, using the appropriate starting materials. LC/MS: 310.4 [M+1]+; 1H NMR (300 MHz, DMSO-d6): δ 8.61 (s, 1H), 7.24 (d, J=3.0 Hz, 1H), 8.06 (s, 1H), 7.96-7.91 (m, 1H), 7.57 (d, J=8.1 Hz, 2H), 6.95 (d, J=8.1 Hz, 2H), 6.53 (d, J=9.3 Hz, 1H), 3.90 (t, J=7.2 Hz, 2H), 3.76 (s, 3H), 1.73-1.65 (m, 2H), 0.88 (t, J=7.4 Hz, 3H).

Example 47: 5-(4-(2-chloro-4-((4-hydroxybutan-2-yl)oxy)phenyl)-1H-pyrazol-1-yl)-1-propylpyridin-2(1H)-one

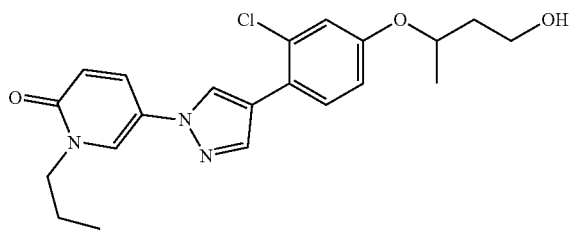 [SMILES: CCCn1cc(-n2cc(-c3ccc(OC(C)CCO)cc3Cl)cn2)ccc1=O]

Step 1: 5-(4-(4-(((tert-butyldimethylsilyl)oxy)butan-2-yl)oxy)-2-chlorophenyl)-1H-pyrazol-1-yl)-1-propylpyridin-2(1H)-one A micro wave vial was charged with 1-propyl-5-(4-(4,4,5,5-tetramethyl-1,3,2-dioxaborolan-2-yl)-1H-pyrazol-1-yl)pyridin-2(1H)-one (0.21 g, 0.6 mmol), 90.0% (3-(4-bromo-3-chlorophenoxy)butoxy)(tert-butyl)dimethylsilane (0.30 g, 0.7 mmol), potassium carbonate (0.26 g, 1.9 mmol) and 1,4-dioxan (12 mL) and water (3 mL) and the flask was degassed and flushed with argon. PdCl2(dppf) (0.05 g, 0.1 mmol) was added and the reaction flask was again degassed and flushed with argon. The reaction mixture was then heated to 100° C. in a microwave for 1.5 hours. The mixture was diluted with ethyl acetate (30 mL) and washed with water, brine, dried over anhydrous sodium sulfate, filtered and concentrated. The resulting black residue was dissolved in DCM and loaded on to a silica gel loading cartridge and filtered with 90% ethyl acetate in hexanes. All compound fractions were collected and concentrated which was used for deprotection without further purification. 1H NMR (300 MHz, CDCl3): δ 8.00 (s, 1H), 7.89 (s, 1H), 7.78 (d, 1H), 7.67 (dd, 1H), 7.36 (d, J=8.7 Hz, 1H), 7.04 (d, 1H), 6.87 (dd, 1H, 6.68 (d, J=9.9H, 1H), 4.62-4.57 (m, 1H), 4.00-3.95 (m, 2H), 3.78-3.64 (m, 2H), 2.00-1.73 (m, 4H), 1.34 (d, J=6.9 Hz, 3H), 1.30-1.24 (m, 3H), 0.89 (s, 9H), 0.04-0.02 (d, 6H).

Step 2: 5-(4-(2-chloro-4-(4-hydroxybutan-2-yl)oxy)phenyl)-1H-pyrazol-1-yl)-1-propylpyridin-2(1H)-one To the crude 5-(4-(4-(((tert-butyldimethylsilyl)oxy)butan-2-yl)oxy)-2-chlorophenyl)-1H-pyrazol-1-yl)-1-propylpyridin-2(1H)-one (0.30 g, 0.6 mmol) was added tetrabutyl ammonium fluoride (1.0 M in THF) (0.65 ml, 0.6 mmol) and stirred at room temperature for 1 hour. The reaction was concentrated and dissolved in acetonitrile and purified on reverse phase HPLC (10-90% acetonitrile/water, 20 min) to afford the title compound as a colorless oil (62 mg, 27%). LC/MS: 402.8 [M+1]+, 1H NMR (300 MHz, CDCl3): δ 8.00 (s, 1H), 7.89 (s, 1H), 7.78 (d, J=3.0 Hz, 1H), 7.66 (dd, J=9.9, 3.0 Hz, 1H), 7.37 (d, J=8.7 Hz, 1H), 7.05 (d, J=2.4 Hz, 1H), 6.87 (dd, J=8.6, 2.5 Hz, 1H), 6.68 (d, J=9.3 Hz, 1H), 4.67-4.61 (m, 1H), 3.97 (t, J=7.4 Hz, 2H), 3.86-3.80 (m, 2H), 2.01-1.78 (m, 4H), 1.73 (b s, 1H), 1.36 (d, J=6.3 Hz, 3H), 1.00 (t, J=7.4 Hz, 3H).

Example 48: 5-(4-(2-chloro-4-(3-hydroxy-2,2-dimethylpropoxy)phenyl)-1H-pyrazol-1-yl)-1-propylpyridin-2(1H)-one

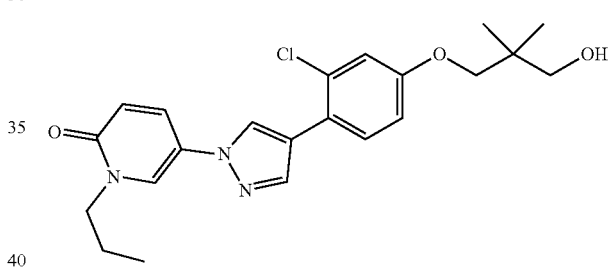

The above compound was prepared as described in example 47, using the appropriate starting materials. LC/MS: 416.8 [M+1]+, 1H NMR (300 MHz, CD3OD): δ 8.34 (s, 1H), 8.18 (d, J=3.0 Hz, 1H), 8.02-7.97 (m, 2H), 7.48 (d, J=8.1 Hz, 1H), 7.07 (d, J=2.1 Hz, 1H), 6.96-6.92 (m, 1H), 6.68 (d, J=10.2 Hz, 1H), 4.03 (t, J=7.6 Hz, 2H), 3.77 (s, 2H), 3.45 (s, 2H), 1.87-1.79 (m, 2H), 1.01-0.97 (m, 9H).

Example 49: 5-(4-(2-chloro-4-((1-(hydroxymethyl)cyclobutyl)methoxy)phenyl)-1H-pyrazol-1-yl)-1-propylpyridin-2(1H)-one

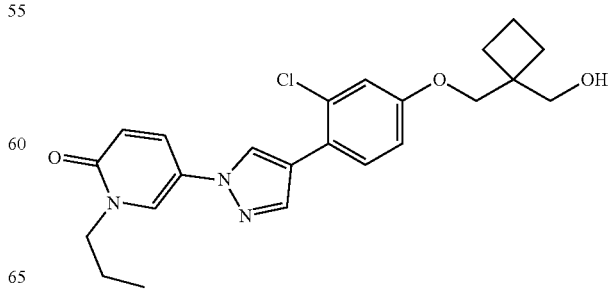

The above compound was prepared as described in example 47, using the appropriate starting materials. LC/MS: 428.2, 430.2 [M+1]+, $^1$H NMR (300 MHz, CDCl$_3$), δ 8.01 (s, 1H), 7.90 (s, 1H), 7.78 (d, J=2.7 Hz, 1H), 7.67 (dd, J=9.6, 2.7 Hz, 1H), 7.38 (d, J=8.4 Hz, 1H), 7.06 (d, J=2.4 Hz, 1H), 6.88 (dd, J=8.4, 2.4 Hz, 1H), 6.68 (d, J=9.9 Hz, 1H), 4.03 (s, 2H), 3.97 (t, J=7.4 Hz, 2H), 3.78 (s, 2H), 2.02-1.94 (m, 6H), 1.88-1.78 (m, 2H), 1.01 (t, J=7.1 Hz, 3H).

Example 50: 5-(4-(6-(cyclopentyloxy)-2-methylpyridin-3-yl)-1H-pyrazol-1-yl)-1-isobutylpyridin-2(1H)-one

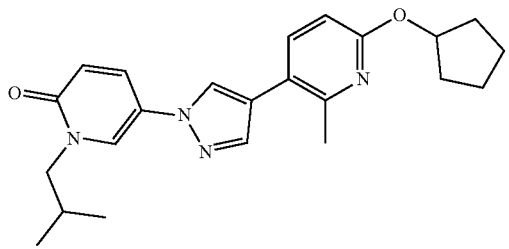 [SMILES: Cc1nc(OC2CCCC2)ccc1-c1cnn(-c2ccc(=O)n(CC(C)C)c2)c1]

Step 1: 5-bromo-1-isobutylpyridin-2(1H)-one

A round bottom flask was charged with 2-hydroxy-5-bromopyridine (4.30 g, 24.7 mmol), 1-iodo-2-methylpropane (8.53 mL, 74.1 mmol), potassium carbonate (17.08 g, 123.6 mmol) and tween 80 (2% W in water, 160 mL) and the reaction mixture heated to 70° C. for 5 days. The reaction mixture was diluted with water and extracted with ethyl acetate (3×50 mL) and the combined organics were washed with brine and dried over Na$_2$SO$_4$ and concentrated. The resulting residue was purified by flash chromatography (40 g silica, 0-50% ethyl acetate in hexanes). The title compound was obtained as a light yellow oil (3.85 g, 68%). LC/MS: [M+1]+ 230; $^1$H NMR (300 MHz, CDCl$_3$): δ 7.35-7.33 (m, 2H), 6.49 (d, J=10.5 Hz, 1H), 3.71 (d, J=7.5 Hz, 2H), 2.19-2.14 (m, 1H), 0.95 (d, J=6.6 Hz, 6H).

Step 2: 5-(4-bromo-1H-pyrazol-1-yl)-1-isobutylpyridin-2(1H)-one

A round bottom flask was charged with 5-bromo-1-isobutylpyridin-2(1H)-one (3.85 g, 16.7 mmol), 4-bromopyrazole (2.46 g, 16.7 mmol) and cesium carbonate (16.35 g, 50.2 mmol), anhydrous DMA (15 mL). Copper(I) iodide (0.319 g, 1.7 mmol) was added and the reaction flask was degassed and flushed with argon. This was repeated three times. The mixture was then stirred at 130° C. for 3 hours. After cooling, the mixture was partitioned between ethyl acetate and water. The layers were separated and the aqueous layer was extracted twice with ethyl acetate (50 mL). The combined organics were washed with brine and dried over MgSO$_4$. The solvents were evaporated to dryness and resulting residue was purified by flash chromatography (40 g silica, 0-40% ethyl acetate in hexanes). The title compound was obtained as a thick oil (1.5 g, 30%). LC/MS: [M+1]+ 296.1/298.0; $^1$H NMR (300 MHz, CDCl$_3$): δ 7.71 (s, 1H), 7.66-7.64 (m, 2H), 7.57 (dd, J=9.3, 2.7 Hz, 1H), 6.67 (d, J=9.3 Hz, 1H), 3.81 (d, J=7.5 Hz, 2H), 2.25-2.20 (m, 1H), 0.97 (d, J=6.3 Hz, 6H).

Step 3: 1-isobutyl-5-(4-(4,4,5,5-tetramethyl-1,3,2-dioxaborolan-2-yl)-1H-pyrazol-1-yl)pyridin-2(1H)-one A round bottom flask was charged with 5-(4-bromo-1H-pyrazol-1-yl)-1-isobutylpyridin-2(1H)-one (1.50 g, 5.1 mmol), 4,4,4',4',5,5,5',5'-octamethyl-2,2'-bi(1,3,2-dioxaborolane) (2.57 g, 10.1 mmol), potassium acetate (1.49 g, 15.2 mmol) and DMSO (14 mL) and the flask was degassed and flushed with argon. PdCl$_2$(dppf) (0.218 g, 0.3 mmol) was added and the reaction flask was again degassed and flushed with argon. This process was repeated three times. The reaction mixture was then heated to 70° C. overnight under argon. The reaction mixture was cooled to room temperature and quenched with saturated NaHCO$_3$ solution and extracted with ethyl acetate (3×100 mL). The combined organics were washed with water, brine, and dried over MgSO$_4$. The solvents were concentrated to dryness and the residue purified by flash chromatography (40 g silica, 0-100% ethyl acetate in hexanes) to get the product as pale red oil (1.0 g, 57%). LC/MS: [M+1]+: 344.3; $^1$H NMR (300 MHz, CDCl$_3$): δ 7.99 (s, 1H), 7.93 (s, 1H), 7.71-7.63 (m, 2H), 6.67 (d, J=9.9 Hz, 1H), 3.89 (d, J=7.5 Hz, 2H), 2.25-2.23 (m, 1H), 1.27-1.25 (m, 12H), 0.97 (d, J=6.3 Hz, 6H).

Step 4: 5-(4-(6-(cyclopentyloxy)-2-methylpyridin-3-yl)-1H-pyrazol-1-yl)-1-isobutylpyridin-2(1H)-one A micro wave vial was charged with 1-isobutyl-5-(4-(4,4,5,5-tetramethyl-1,3,2-dioxaborolan-2-yl)-1H-pyrazol-1-yl)pyridin-2(1H)-one (0.12 g, 0.3 mmol), 3-bromo-6-(cyclopentyloxy)-2-methylpyridine (0.13 g, 0.4 mmol), potassium carbonate (0.15 g, 1.1 mmol) and 1,4-dioxan (12 mL) and water (3 mL) and the flask was degassed and flushed with argon. PdCl$_2$(dppf) (0.03 g, 0.04 mmol) was added and the reaction flask was again degassed and flushed with argon. This was repeated three times. The reaction mixture was then heated to 100° C. in a microwave for 120 minutes. The reaction was cooled to room temperature and quenched with sat. NaHCO$_3$ and extracted with ethyl acetate (3×50 mL). The combined organics were washed with water, brine and dried over MgSO$_4$. The solvents were evaporated to dryness and the residue purified by flash chromatography (4 g silica gel, 0-10% methanol in DCM) to afford the product as light brown oil (35 mg, 25%). LC/MS: 393.5 [M+1]+, $^1$H NMR (300 MHz, CDCl$_3$): δ 7.75-7.66 (m, 4H), 7.50 (d, J=8.1 Hz, 1H), 6.69 (d, J=9.9 Hz, 1H), 6.57 (d, J=8.1 Hz, 1H), 3.84 (d, J=6.9 Hz, 2H), 2.54 (s, 3H), 2.26-1.64 (m, 10H), 1.01 (d, J=6.0 Hz, 6H).

Example 51: 5-(4-(4-(ethylsulfonyl)phenyl)-1H-pyrazol-1-yl)-1-propylpyridin-2(1H)-one

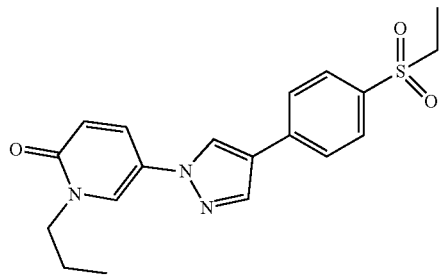 [SMILES: CCCn1cc(-n2cc(-c3ccc(S(=O)(=O)CC)cc3)cn2)ccc1=O]

A microwave vial was charged with 5-(4-bromo-1H-pyrazol-1-yl)-1-propylpyridin-2(1H)-one (0.20 g, 0.7 mmol), 4-(ethylsulfonyl)phenylboronic acid (0.15 g, 0.7 mmol), potassium carbonate (0.29 g, 2.1 mmol), 1,4-dioxane (10 mL) and water (1 mL). The vial was degassed and flushed with argon. [1,1'-bis(diphenylphosphino)ferrocene]dichloropalladium(II), complex with dichloromethane (0.06 g, 0.1 mmol) was added and the microwave vial was again degassed and flushed with argon. The reaction mixture was then heated to 100° C. in a microwave for 90 minutes. The reaction mixture was cooled to room temperature and quenched with water and extracted with ethyl acetate (3×25 mL). The combined organics were washed with brine and dried over sodium sulfate. The solvents were concentrated. The residue was purified by flash chromatography (24 g silica, 0-100% ethyl acetate in hexanes). The product was purified again by reverse phase HPLC (20-80% Acetonitrile/water (0.1% DEA) to give a white solid (130 mg). LC/MS: 372.6 [M+1]$^+$, $^1$H NMR (300 MHz, CD$_3$OD): δ 8.64 (s, 1H), 8.23-8.19 (m, 2H), 8.04-7.99 (m, 1H), 7.91 (s, 4H), 6.69 (d, J=9.3 Hz, 1H), 4.04 (t, J=7.4 Hz, 2H), 3.29-3.19 (m, 2H), 1.88-1.80 (m, 2H), 1.24 (t, J=7.4 Hz, 3H), 1.01 (t, J=7.5 Hz, 3H).

Example 52: 5-(4-(6-(isopropylsulfonyl)-2-methylpyridin-3-yl)-1H-pyrazol-1-yl)-1-propylpyridin-2(1H)-one

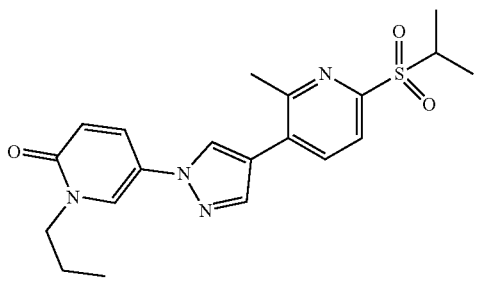 [SMILES: CCCn1cc(-n2cc(-c3ccc(S(=O)(=O)C(C)C)nc3C)cn2)ccc1=O]

Step 1: 3-bromo-6-(isopropylthio)-2-methylpyridine

A microwave vial was charged with 3,6-dibromo-2-methylpyridine (1.0 g, 4.0 mmol), cesium carbonate (2.6 g, 8.0 mmol), DMSO (8 mL) and propane-2-thiol (1.9 mL, 19.9 mmol). The reaction was stirred at room temperature overnight. The reaction mixture was quenched with water and extracted with ethyl acetate (3×50 mL). The solvents were evaporated to dryness and the residue used in the next reaction without purification. $^1$H NMR (300 MHz, CDCl$_3$): δ 7.56 (d, J=8.4 Hz, 1H), 6.87 (d, J=8.1 Hz, 1H), 3.96-3.91 (m, 1H), 2.61 (s, 3H), 1.39 (d, J=6.9 Hz, 6H).

Step 2: 3-bromo-6-(isopropylsulfonyl)-2-methylpyridine

To a solution of 50.0% 3-bromo-6-(isopropylthio)-2-methylpyridine (1.0 g, 2.0 mmol) in DCM (20 ml) was added 75.0% m-chloroperoxybenzoic acid (1.4 g, 6.1 mmol). The reaction mixture was stirred at room temperature overnight. The solid was filtered off, and the filtrate was concentrated to dryness and the residue purified by flash chromatography (0-15% ethyl acetate in hexanes) to give the product as light yellow oil. $^1$H NMR (300 MHz, CDCl$_3$): δ 8.06 (d, J=8.4 Hz, 1H), 7.80 (d, J=8.1 Hz, 1H), 3.83-3.74 (m, 1H), 2.76 (s, 3H), 1.34 (d, J=6.6 Hz, 6H).

Step 3: 5-(4-(6-(isopropylsulfonyl)-2-methylpyridin-3-yl)-1H-pyrazol-1-yl)-1-propylpyridin-2(1H)-one A micro wave vial was charged 1-propyl-5-(4-(4,4,5,5-tetramethyl-1,3,2-dioxaborolan-2-yl)-1H-pyrazol-1-yl)pyridin-2(1H)-one (0.14 g, 0.4 mmol), 3-bromo-6-(isopropylsulfonyl)-2-methylpyridine (0.2 g, 0.4 mmol), potassium carbonate (0.18 g, 1.3 mmol) and 1,4-dioxan (12 mL) and water (3 mL) and the flask was degassed and flushed with argon. PdCl$_2$(dppf) (0.035 g, 0.04 mmol) was added and the reaction flask was again degassed and flushed with argon. The reaction mixture was then heated to 100° C. in a microwave for 90 minutes. The reaction was cooled to room temperature and quenched with water and extracted with ethyl acetate (3×50 mL). The combined organics were washed with water, brine and dried over MgSO$_4$. The solvents were evaporated to dryness and the residue purified by flash chromatography (12 g silica gel, 0-80% ethyl acetate in hexanes) to afford the product as light yellow solid. LC/MS: 401.6 [M+1]$^+$, $^1$H NMR (300 MHz, CDCl$_3$): δ 8.00-7.83 (m, 5H), 7.68 (d, J=9.0 Hz, 1H), 6.72 (d, J=10.2 Hz, 1H), 4.00 (t, J=7.2 Hz, 2H), 3.86-3.81 (m, 1H), 2.78 (s, 3H), 1.91-1.83 (m, 2H), 1.37 (d, J=6.9 Hz, 6H), 1.03 (t, J=7.4 Hz, 3H).

Example 53: 5-(4-(2-isopropoxypyrimidin-5-yl)-1H-pyrazol-1-yl)-1-propylpyridin-2(1H)-one

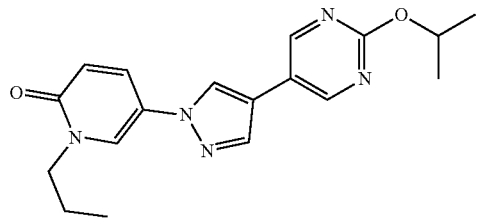 [SMILES: CCCn1cc(-n2cc(-c3cnc(OC(C)C)nc3)cn2)ccc1=O]

Step 1: 5-bromo-2-isopropoxypyrimidine

A microwave vial was charged with 5-Bromo-2-chloropyrimidine (1.0 g, 5.2 mmol), DMF (8 mL), cesium carbonate (3.4 g, 10.3 mmol) and 2-propanol (2.4 mL, 25.8 mmol). The reaction was stirred at 90° C. for 3 hours in a microwave reactor. The reaction mixture was quenched with water and extracted with ethyl acetate (3×50 mL). The combined organics were washed with brine and dried over sodium sulfate. The solvents were evaporated to dryness and the residue used in the next reaction without purification. $^1$H NMR (300 MHz, CDCl$_3$): δ 8.51 (s, 2H), 5.26-5.18 (m, 1H), 1.40 (d, J=5.7 Hz, 6H).

Step 2: 5-(4-(2-isopropoxypyrimidin-5-yl)-1H-pyrazol-1-yl)-1-propylpyridin-2(1H)-one A micro wave vial was charged 1-propyl-5-(4-(4,4,5,5-tetramethyl-1,3,2-dioxaborolan-2-yl)-1H-pyrazol-1-yl)pyridin-2(1H)-one (0.2 g, 0.6 mmol), 5-bromo-2-isopropoxypyrimidine (0.15 g, 0.6 mmol), potassium carbonate (0.25 g, 1.8 mmol) and 1,4-dioxan (12 mL) and water (3 mL) and the flask was degassed and flushed with argon. PdCl$_2$ (dppf)

(0.05 g, 0.1 mmol) was added and the reaction flask was again degassed and flushed with argon. The reaction mixture was then heated to 100° C. in a microwave for 90 minutes. The reaction was cooled to room temperature and quenched with water and extracted with ethyl acetate (3×50 mL). The combined organics were washed with water, brine and dried over MgSO$_4$. The solvents were evaporated to dryness and the residue purified by flash chromatography (12 g silica gel, 0-70% ethyl acetate in hexanes) to afford the product as brown solid. LC/MS: 340.3 [M+1]$^+$, $^1$H NMR (300 MHz, CDCl$_3$): δ 8.65 (s, 2H), 7.91 (d, J=2.4 Hz, 2H), 7.79 (s, 1H), 6.67 (d, J=9.9 Hz, 1H), 6.71 (d, J=9.3 Hz, 1H), 5.33-5.29 (m, 1H), 3.98 (t, J=7.4 Hz, 2H), 1.90-1.82 (m, 2H), 1.43 (d, J=6.6 Hz, 6H), 1.02 (t, J=7.4 Hz, 3H).

Example 54: 5-(4-(2-(isopropylsulfonyl)pyrimidin-5-yl)-1H-pyrazol-1-yl)-1-propylpyridin-2(1H)-one

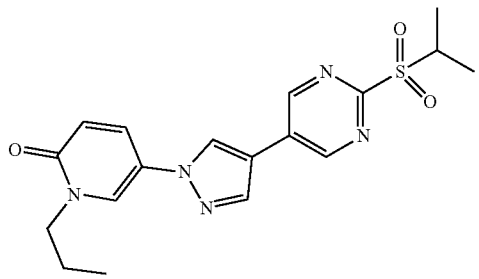 [SMILES: CCCn1cc(-n2cc(-c3cnc(S(=O)(=O)C(C)C)nc3)cn2)ccc1=O]

Step 1: 5-bromo-2-(isopropylthio)pyrimidine

A microwave vial was charged with 5-bromo-2-chloropyrimidine (1.0 g, 4.3 mmol), ethanol (8 mL), cesium carbonate (2.8 g, 8.7 mmol) and propane-2-thiol (2.0 mL, 21.7 mmol). The reaction was stirred at 55° C. overnight. The reaction mixture was quenched with water and extracted with ethyl acetate (3×50 mL). The solvents were evaporated to dryness and the residue used in the next reaction without purification. $^1$H NMR (300 MHz, CDCl$_4$): δ 8.56 (s, 2H), 3.93-3.84 (m, 1H), 1.43 (d, J=7.2 Hz, 6H).

Step 2: 5-bromo-2-(isopropylsulfonyl)pyrimidine

To a solution of 5-bromo-2-(isopropylthio)pyrimidine (1.1 g, 4.2 mmol) in DCM (20 mL) was added m-chloroperoxybenzoic acid (2.9 g, 12.7 mmol). The reaction mixture was stirred at room temperature overnight. The solid was filtered off, and the filtrate was concentrated to dryness and the residue purified by flash chromatography (12 g silica, 0-20% ethyl acetate in hexanes) to give the product as tan colored solid. $^1$H NMR (300 MHz, CDCl$_3$): δ 9.02 (s, 2H), 3.94-3.87 (m, 1H), 1.42 (d, J=7.2 Hz, 6H).

Step 3: 5-(4-(2-(isopropylsulfonyl)pyrimidin-5-yl)-1H-pyrazol-1-yl)-1-propylpyridin-2(1H)-one A micro wave vial was charged 1-propyl-5-(4-(4,4,5,5-tetramethyl-1,3,2-dioxaborolan-2-yl)-1H-pyrazol-1-yl)pyridin-2(1H)-one (0.2 g, 0.6 mmol), 5-bromo-2-(isopropylsulfonyl)pyrimidine (0.18 g, 0.6 mmol), potassium carbonate (0.25 g, 1.8 mmol) and 1,4-dioxan (12 mL) and water (3 mL) and the flask was degassed and flushed with argon. PdCl$_2$(dppf) (0.05 g, 0.1 mmol, 0.1 equiv.) was added and the reaction flask was again degassed and flushed with argon. The reaction mixture was then heated to 100° C. in a microwave for 90 minutes. The reaction was cooled to room temperature and quenched with water and extracted with ethyl acetate (3×50 mL). The combined organics were washed with water, brine and dried over MgSO$_4$. The solvents were evaporated to dryness and the residue purified by flash chromatography (12 g silica gel, 0-100% ethyl acetate in hexanes) to afford the product as brown solid. LC/MS: 388.6 [M+1]$^+$, $^1$H NMR (300 MHz, CDCl$_3$): δ 9.09 (s, 2H), 8.18 (s, 1H), 8.08 (s, 1H), 7.85 (s, 1H), 7.70 (d, J=8.1 Hz, 1H), 6.72 (d, J=9.6 Hz, 1H), 4.02-3.91 (m, 3H), 1.90-1.83 (m, 2H), 1.44 (d, J=6.9 Hz, 6H), 1.03 (t, J=7.4 Hz, 3H).

Example 55: 5-(4-(2-chloro-4-(ethylsulfonyl)phenyl)-1H-pyrazol-1-yl)-1-propylpyridin-2(1H)-one

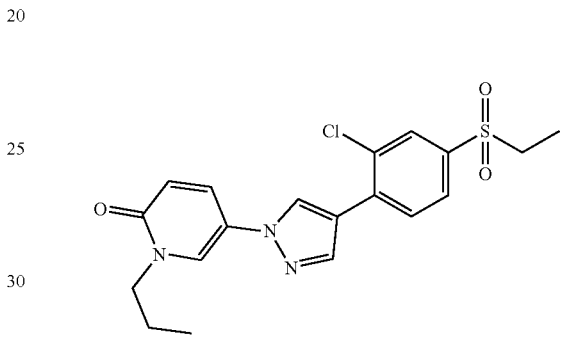

A micro wave vial was charged with 1-propyl-5-(4-(4,4,5,5-tetramethyl-1,3,2-dioxaborolan-2-yl)-1H-pyrazol-1-yl) pyridin-2(1H)-one (0.25 g, 0.8 mmol), prepared as described above for Example 1, 1-bromo-2-chloro-4-(ethylsulfonyl) benzene (0.308 g, 0.8 mmol), prepared as described above for Intermediate A, potassium carbonate (0.315 g, 2.3 mmol) and 1,4-dioxan (12 mL) and water (3 mL) and the flask was degassed and flushed with argon. PdCl$_2$(dppf) (0.062 g, 0.1 mmol) was added and the reaction flask was again degassed and flushed with argon. This process was done three times. The reaction mixture was then heated to 100° C. in a microwave for 90 minutes. The reaction was cooled to room temperature and quenched with sat. NaHCO$_3$ and extracted with ethyl acetate (3×50 mL). The combined organics were washed with water, brine and dried over MgSO$_4$. The solvents were evaporated to dryness and the residue purified by flash chromatography (12 g silica gel, 0-40% ethyl acetate in hexanes) to afford the product as light yellow solid (55 mg, 18%). LC/MS: 406.6 [M+1]$^+$, $^1$H NMR (300 MHz, CDCl$_3$): δ 8.23 (s, 1H), 8.05 (s, 1H), 8.03 (s, 1H), 7.84-7.82 (m, 2H), 7.71 (d, J=7.5 Hz, 1H), 7.67 (d, J=2.7 Hz, 1H), 6.71 (d, J=9.9 Hz, 1H), 3.99 (t, J=7.2 Hz, 2H), 3.17 (q, J=7.6 Hz, 2H), 1.90-1.83 (m, 2H), 1.34 (t, J=7.5 Hz, 3H), 1.03 (t, J=7.4 Hz, 3H).

Additional compounds of the invention (Embodiment A), which can be prepared using methods disclosed herein and known to one of ordinary skill in the art and using readily-obtainable or commercially-available starting materials, include the following:

Embodiment A
(56) 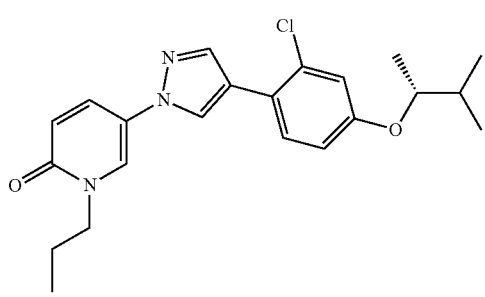
(57) 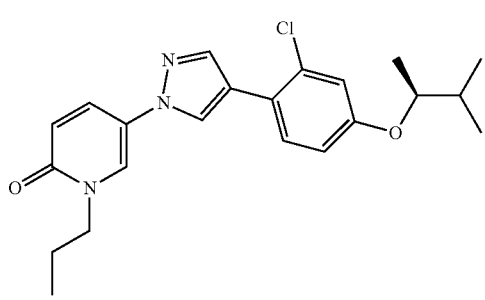
(58) 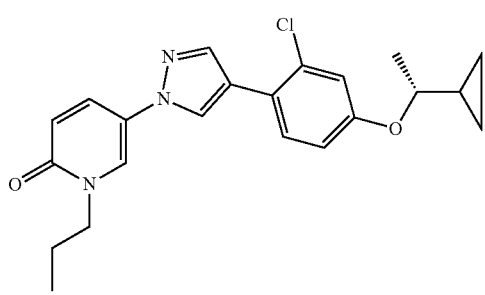
(59) 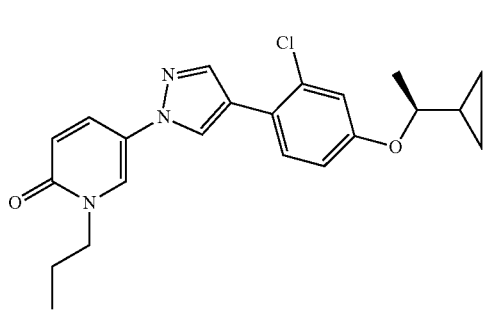
(60) 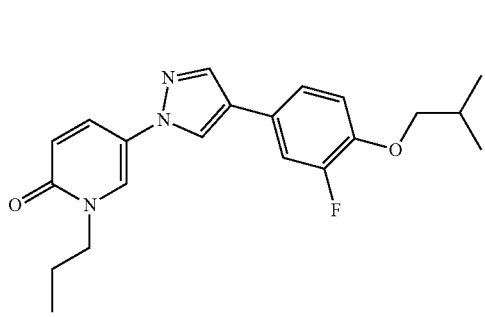
(61) 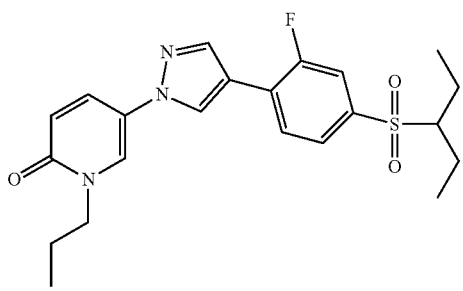
(62) 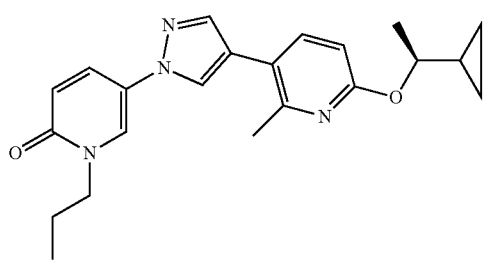
(63) 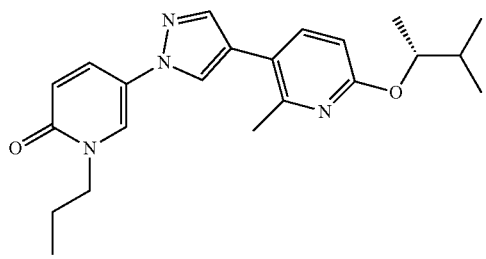
(65) 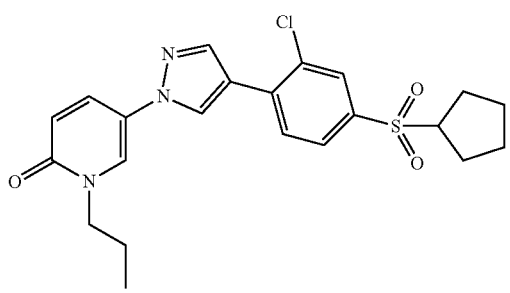
(66) 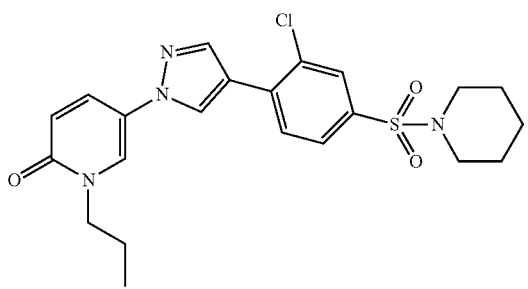

(67)
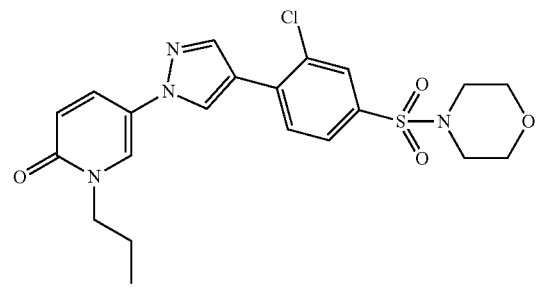
(68)
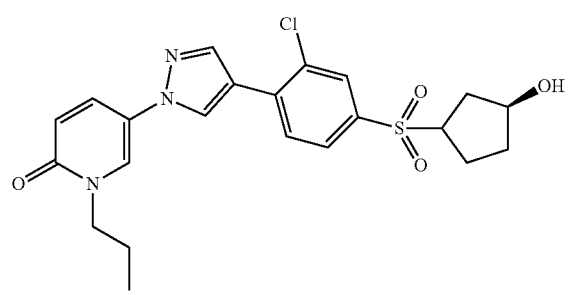
(69)
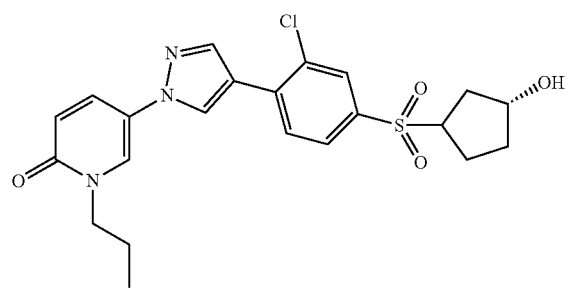
(70)
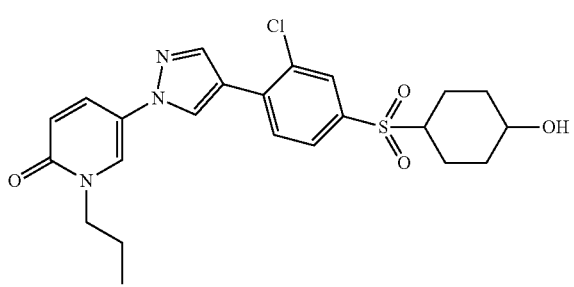
(71)
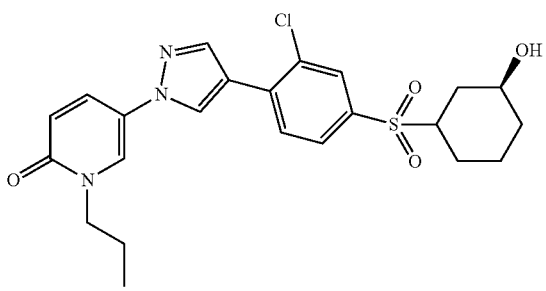
(72)
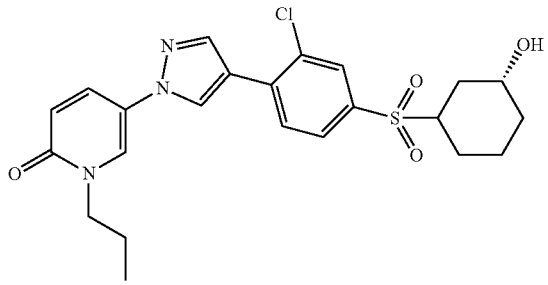
(73)
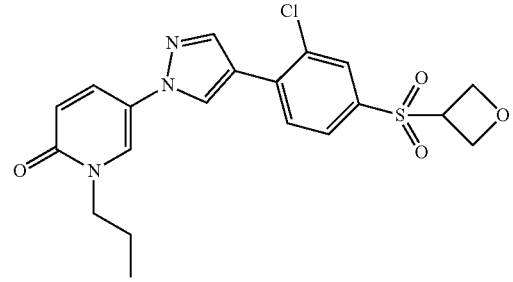
(74)
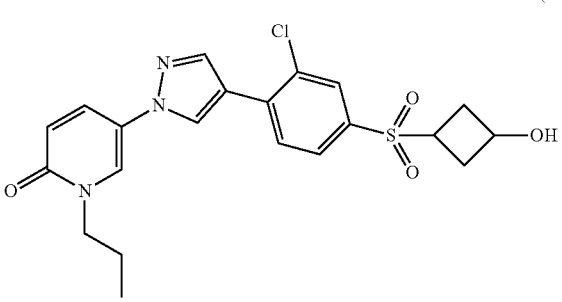
(75)
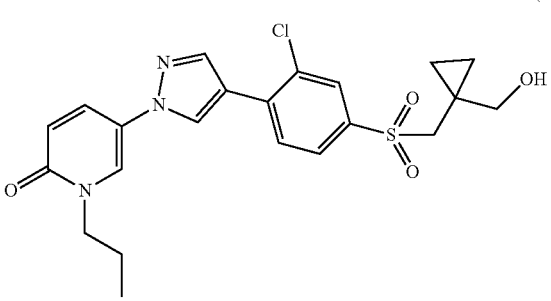
(76)
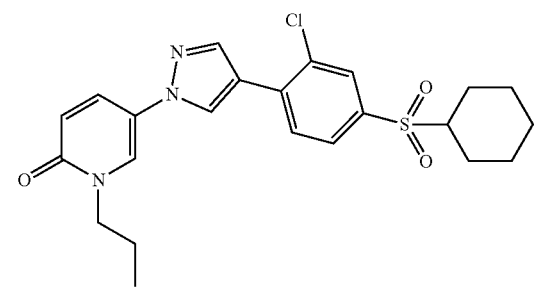

-continued

(77)
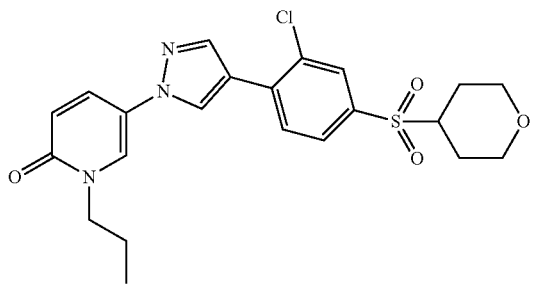

(83)
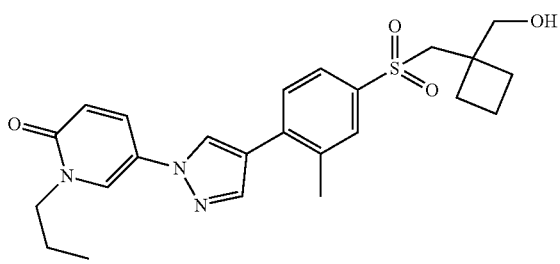

(84)
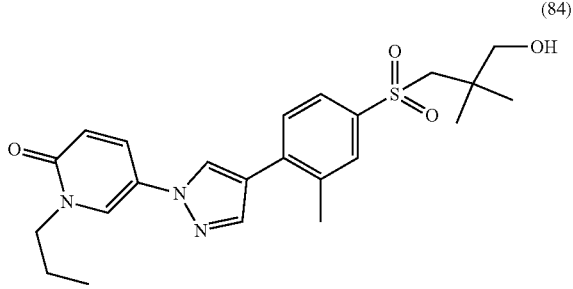

(85)
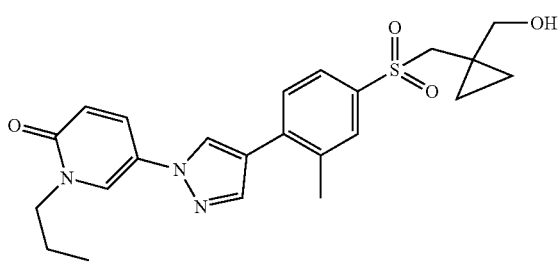

(86)
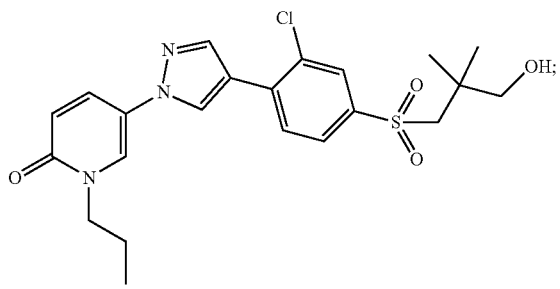

or a stereoisomer, a mixture of stereoisomers, and/or a pharmaceutically acceptable salt thereof.

Biological Example 1a

Inhibition Assay

Quantitative PCR (qPCR)

Hep G2 cells were obtained from ATCC and grown in DMEM supplemented with 10% FBS in a 5% $CO_2$ incubator at 37° C. For the assay the cells were plated in 96 well plates at a concentration of 75,000 cells/well in DMEM with 5% FBS. The compounds were serially diluted in DMSO from 30 to 0.1 mM and then diluted 1:1000 in growth medium. The medium was added to the cells in duplicate 24 hours after plating. After 24 hours of incubation the RNA was isolated from the cells using the RNAqueous®-96 Total RNA Isolation Kit (Ambion). The eluted RNA was reverse transcribed using the Cells-to-Ct kit reverse transcriptase (Ambion). For the quantitative PCR the cDNA was analyzed using the Power SYBR® Green PCR Master Mix (Applied Biosystems) and gene specific primers. The reaction was run on an ABI7300 thermocycler and the instrument software was used to determine the Ct values. The fold change of mRNA expression relative to the vehicle control was calculated using the method by Livak. Primer sequence was as follows: SCD1, 5'-cctggtatttctggggtgaa-3'/5'-gggggct aatgttcttgtca-3'.

Biological Example 1b

Inhibition Assay

Quantitative PCR (qPCR)

Hep G2 cells were obtained from ATCC and grown in DMEM supplemented with 5% FBS in a 5% $CO_2$ incubator at 37° C. For the assay the cells were plated in 24 well plates at a concentration of 100,000 cells/well in DMEM with 5% FBS. The compounds were serially diluted in DMSO from 0.1 to 20 mM and then diluted 1:1000 in growth medium. The medium was added to the cells in duplicate 24 hours after plating. After 24 hours of incubation the RNA was isolated from the cells using the illustra RNAspin Mini kit (GE Healthcare). For the quantitative PCR the RNA was analyzed using the Power SYBR® Green PCR Master Mix (Applied Biosystems) and gene specific primers. The reaction was run on a StepOnePlus Real-Time PCR System (Thermo Fisher Scientific) and the instrument software was used to determine the Ct values. The fold change of mRNA expression relative to the vehicle control was calculated. Primer sequence was as follows: PCSK9, 5'-cagcctggtg-gaggtgtatc-3'/5'-gccatgactgtcacacttgc-3'.

All data for Biological Examples 1a and 1b were measured in HepG2 cells. % inhibition of SCD1 expression, % inhibition of PCSK9 expression, and PCSK9 $IC_{50}$ data are provided in Table 1. NA means the compound was not active at the concentration tested. A means the compound provided a percent inhibition of ≥40%; and B means the compound provided a percent inhibition of greater than or equal to 10% but less than 40%. C means the compound provided an $IC_{50}$ of ≤150 nM; and D means the compound provided an $IC_{50}$ of greater than 150 nM but less than or equal to 600 nM.

TABLE 1

| Ex. No. | SCD1 Inhibition Percentage (%) at 1 μM | PCSK9 Inhibition Percentage (%) at 320 nM | PCSK9 IC$_{50}$ (nM) |
|---|---|---|---|
| 1 | A | — | — |
| 2 | A | — | — |
| 3 | A | B | — |
| 4 | A | — | — |
| 5 | A | A | — |
| 6 | A | B | D |
| 7 | A | — | — |
| 8 | — | A | D |
| 9 | A | A | — |
| 10 | A | A | — |
| 11 | A | — | — |
| 12 | B | — | — |
| 13 | — | A | C |
| 14 | — | A | C |
| 15 | — | A | C |
| 16 | — | A | C |
| 17 | A | A | D |
| 18 | B | B | — |
| 19 | A | — | — |
| 20 | A | — | — |
| 21 | A | — | — |
| 22 | A | — | D |
| 23 | A | — | C |
| 25 | A | — | — |
| 26 | — | A | — |
| 27 | — | NA | — |
| 28 | — | NA | — |
| 29 | — | NA | — |
| 30 | — | B | — |
| 31 | — | B | — |
| 32 | A | — | — |
| 33 | A | — | — |
| 34 | A | — | — |
| 35 | A | — | — |
| 36 | A | — | — |
| 37 | A | — | — |
| 38 | — | A | — |
| 39 | — | A | D |
| 40 | B | — | — |
| 41 | A | — | — |
| 42 | B | — | — |
| 43 | NA | — | — |
| 45 | B | — | — |
| 46 | B | — | — |
| 47 | A | — | — |
| 48 | A | — | — |
| 49 | — | A | C |
| 50 | A | — | — |
| 51 | A | — | — |
| 52 | — | NA | — |
| 53 | — | NA | — |
| 54 | — | NA | — |
| 55 | A | — | — |
| 64 | A | — | — |
| 78 | — | A | C |
| 79 | — | B | — |
| 80 | — | B | — |
| 81 | — | A | C |
| 82 | — | A | — |

Biological Example 2

Cell Viability Assay

HepG2 cells were cultured in DMEM containing 5% FBS and antibiotic-antimycotic and were grown in a humidified incubator at 37° C. with 5% CO$_2$. For the assay, 2,000 HepG2 cells were seeded into each well of 96 well plates. After one day (24 h) in culture, cells were treated with test compound B, C or D, or at concentrations of 0, 1, 10, 32, 100, 320, 1000, 3200, 10,000, and 20,000 nM or with test compound A at concentrations of 0, 1000, 3000, 10,000 and 30,000 nM. for 48 and 72 hr. The cell viability was assessed using Thiazolyl Blue Tetrazolium Bromide (MTT) assay (n=3 for each dose). 5 mg/mL MTT is added in an amount equal to 10% of the culture medium volume after 48- and 72-hr treatment with the test compound. After the plates were incubated at 37° C. for 3.5 hours, the medium was removed and formazan crystals were dissolved in isopropanol. The absorbance was measured on a Cytation 5 epi-fluorescence microscope at a wavelength of 550 nm and 690 nm. The absorbance at 690 nm was subtracted from the absorbance at 550 nm and the result was used for graphing.

See Table 2 for IC$_{50}$ for Compounds A, B, C, and D, compounds within the scope of the invention and specifically recited herein.

| Compound | IC$_{50}$ (μM) in HePG2 cells, after 48 h treatment | IC$_{50}$ (μM) in HePG2 cells, after 72 h treatment |
|---|---|---|
| A | 0.87 | 0.25 |
| B | 0.6 | 0.21 |
| C | 1.2 | 0.39 |
| D | 1.5 | 0.89 |

The above procedure can be followed for determining activity in Huh7, MDA-MB-231, T47D, MCF7, and DU145 cells.

Biological Example 3

Immunoblotting Assay

For the experiment, 1*10$^6$ cells are seeded in 6 well plates cultured in DMEM with 5% fetal bovine serum at 37° C., 5% CO$_2$, 95% air and 100% relative humidity for 24 hrs, then treated with different dosage of the test compound for another 24 hr. After treatment, cells are washed once with ice-cold PBS and scraped into radioimmunoprecipitation assay (RIPA) lysis buffer containing protease and phosphatase inhibitor cocktail. The extract is sonicated (3*10 sec) and centrifuged at 14,000 rpm for 10 min. The protein concentration of each total cell extract is measured by Protein Assay Reagent A (Bio-rad). Equal amounts of protein extracts are separated on 10% Tris-glycine SDS-PAGE gel (Fisher Scientific) and then transferred to a PVDF membrane. After blocking for 1 hour in Odyssey blocking buffer in PBS, the membrane is probed with indicated antibodies, followed by secondary antibodies conjugated to IRDye 800CW or IRDye 680LT and then imaged in an ODYSSEY imaging system to detect SREBP-1, MVD, SCD1, SREBP1, SREBP2, PCSK9, and/or LDLR. We used software Image Studio Lite Ver 5.2 to quantify the intensity of specific protein bands including actin for normalization.

Biological Example 4

Effect of Compounds A, B and C on Protein Levels of PCSK9 and LDL Receptor (LDLR) in HePG2 Cells.

Figure 1B:
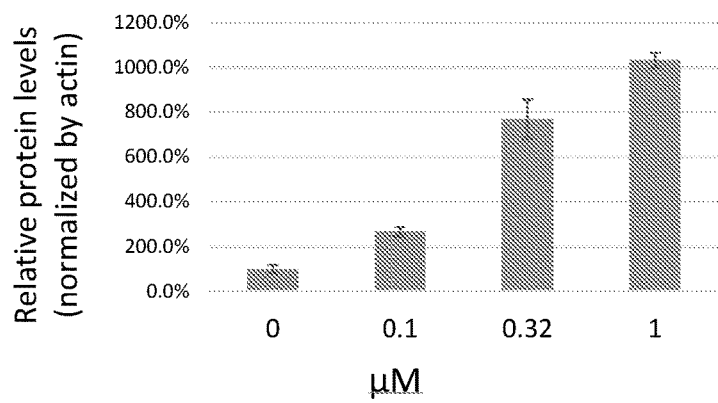
FIG. 1B shows a histogram indicating increased LDLR protein levels with a dose-response for compound A.
Figure 1C:
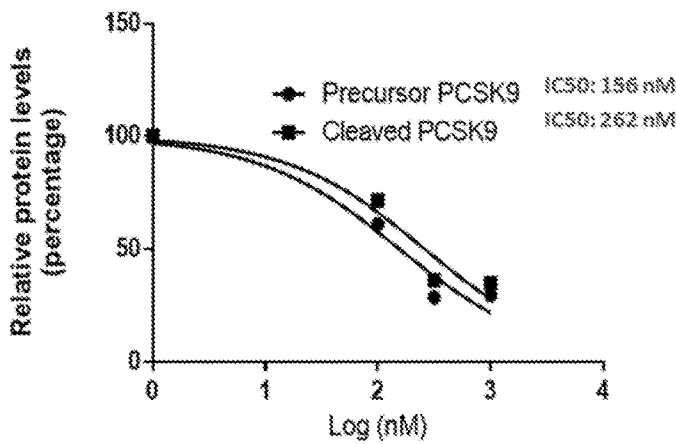
FIG. 1C shows $IC_{50}$ curves for Compound A against PCSK9.

PCSK9 is one of several genes that is positively regulated by SREBP. Compounds A, B, and C, compounds within the scope of the invention and specifically recited herein, down regulated mRNA levels of PCSK9 in HePG2 cells. Using Western blot method, changes in protein levels of PCSK9 in response to different doses of compounds A, B and C after 24 hours treatment were determined. As shown in FIG. 1A both the precursor and the cleaved forms of PCSK9 were highly expressed in control HePG2 cells, and their levels decreased in a dose dependent manner. The $IC_{50}$ for precursor and cleaved PCSK9 were 156 and 262 nM, respectively (FIG. 1C).

Figure 2A:
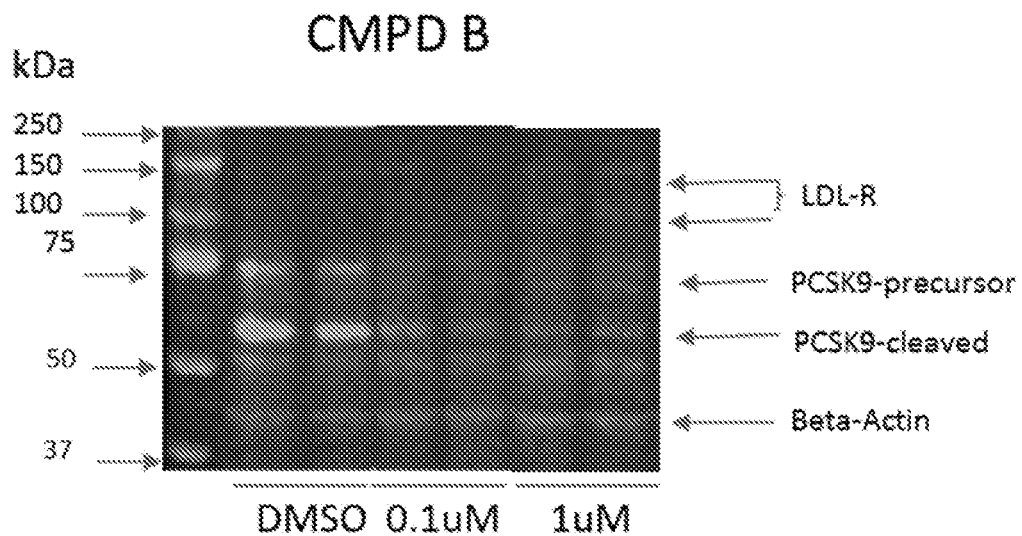
FIGS. 2A and 2B show Western blots from liver extracts using control and Compound B (FIG. 2A) or Compound C (FIG. 2C) treated HepG2 cells after 24 h, where Compounds B and C down-regulated PCSK9 in a dose-dependent manner.
Figure 2B:
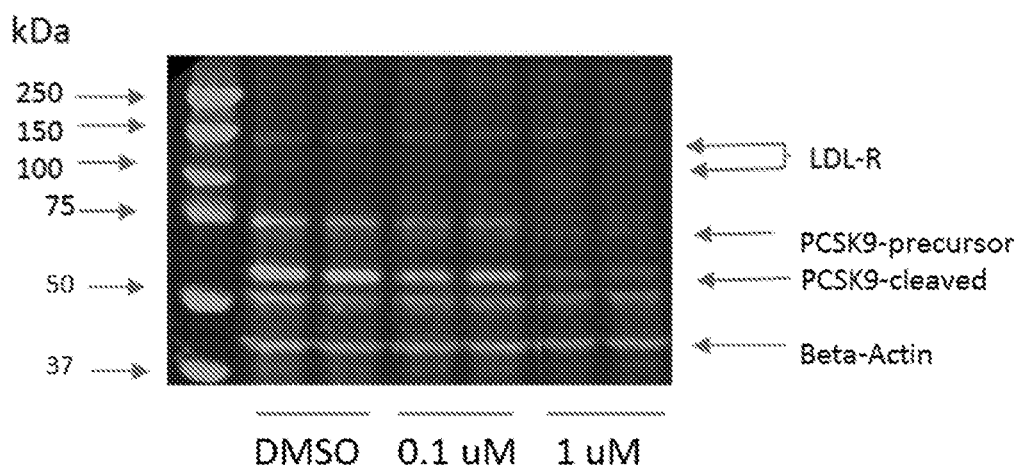

Numerous studies have shown that the protein level of LDLR is negatively regulated by PCSK9, through proteolytic mechanism. LDLR protein was very low (almost undetectable) in control HePG2 cells (FIG. 1A). On the other hand, there was a significant increase in the protein level of LDLR in parallel with the decrease in PCSK9 protein in compound-treated cells. The LDLR protein levels increased by 200, 800 and 1000% at 0.1, 0.32 and respectively, of Compound A (FIG. 1B). Similarly, Compounds B and C also significantly decreased the level of PCSK9 protein and increased LDLR protein in a dose dependent manner (FIGS. 2A and 2B). Both compounds were very effective in reducing PCSK9 protein level at 0.1 μM which was accompanied by an increase in LDLR protein levels. These results are consistent with the down regulation of PCSK9 mRNA by these compounds.

Biological Example 5

In Vivo Model

Sprague-Dawley rats (100-200 gm) will be obtained from Charles River Breeding Laboratories, Wilmington, Mass. Commercial laboratory chow and water will be provided ad libitum. ob/ob Mice (10 per group) are fed normal chow (control diet) or chow that contains 100 mg/kg, 200 mg/kg, 300 mg/kg or 400 mg/kg of the test compound. The test compound is administered orally to ob/ob mice daily over a period of 8 weeks. Daily food intake and water consumption are carefully monitored. Mice are weighed daily, and fat and lean body content are determined by dual-energy X-ray absorptiometry (DEXA). % fat is calculated as fat weight/ fat+lean weight. Blood constituents are determined using standard procedures. Glucose tolerance is measured in order to investigate the ability of treated mice to clear blood glucose compared to control animals. Three groups (10 per group) of mice are fasted overnight and blood glucose levels are measured at 0, 30, 60, and 120 min after the injection of glucose (2 g/kg body weight).

Biological Example 6

In Vivo Model

Sprague-Dawley rats have been used to study human obesity induced by a Western diet (WD) (high-fat, high-carbohydrate diet). Twenty 5- to 6-week-old male rats are fed a WD ad libitum for 3 weeks. Food consumption and body weight are measured every 3 days. Obesity and weight gain are first seen after 2 weeks and become most apparent after 4-5 weeks of this diet. This diet brings about insulin resistance in about 2 weeks. After 3 weeks of feeding WD, the test compound is administered daily at 10 mg/kg to the experimental group (20 rats) by oral gavage. The control group (n=20) is given vehicle only at the same time. Animals are treated for 2 months.

Food intake, water consumption, and body weight are determined and recorded every 3 days for the duration of the experiment. Rats are fed the WD diet for a total of 2 months and 3 weeks. The first 3 weeks are WD alone. After the first 3 weeks, the experimental groups receives the test compound daily.

Before the start of dosing with the test compound, baseline blood constituents are determined. The animals are fasted for 8 hours, and TG, HDL, LDL, VLDL, cholesterol, glucose and insulin levels are determined using standard methods. A glucose tolerance test (GTT) is carried out using standard methods. Body composition (lean and body fat) is determined using dual-energy X-ray absorptiometry on live animals, using standard methods. Body weight and food intake are measured every week, and 1 month after the start of the treatment, blood constituents are determined to measure glucose, TG, HDL, LDL and VLDL in addition to the liver enzymes: aspartate aminotransferase (AST) and alanine aminotransferase (ALT). GTT is also performed in order to assess the insulin-resistant state 4 and 8 weeks after the start of the treatment. Fat and lean body mass are assessed by $^1H$ magnetic resonance spectroscopy (Bruker BioSpin, Billerica, Mass., USA) before and after 4 weeks of treatment. A comprehensive animal metabolic monitoring system (CLAMS: Columbus Instruments, Columbus, Ohio, USA) is used to evaluate activity, food consumption and energy expenditure before and after 4 weeks of treatment. Energy expenditure and food intake data is normalized with respect to body weight. Energy expenditure and respiratory quotient (RQ) are calculated from the gas exchange data. Energy expenditure=$(3.815+1.232*RQ)*VO_2$. RQ is the ratio of $VCO_2$ to $VO_2$, which changes depending on the energy source the animal is using. When carbohydrates are the only substrate being oxidized, the RQ is 1.0, and it is 0.7 when only fatty acids are oxidized. Activity is measured on an x and z-axis using infrared beams to count the amount of beam breaks during the specified measurement period. Feeding is measured by recording the difference in the scale measurement of the Center-Feeder from one time point to another.]

Following the 2 months of treatment, rats are sacrificed to determine the biochemical and histopathological impact of the test compound on liver, muscle, heart and adipose tissues. The tissues are collected, weighed and kept at $-80°$ C. for further analyses, as follows:

Histological staining for lipid, glycogen and general tissue structure.

TG and cholesterol levels using biochemical methods.

Assays for lipogenic enzymes, such as fatty acid synthase (FAS), acetyl-CoA carboxylases (ACC1 and ACC2), stearoyl-CoA desaturase (SCD1), and enzymes of cholesterol synthesis, 3-hydroxy 3-methyl glutaryl-CoA synthase and reductase, among others.

Expression level of genes previously found to be modulated by fatostatin in both cell culture and mouse studies, including SREBP1 and -2, done using real-time PCR for RNA levels and Western blot assays for protein.

Statistical analyses are performed with commercially available software. Data are expressed as mean+SD. Statistical comparison of changes between control and treated animals are analyzed by one-way ANOVA. Unpaired Student t-test is used to compare the treated animals and the controls. Values of $P<0.05$ are considered statistically significant.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof

What is claimed is:

1. A Compound of Formula (Ib):

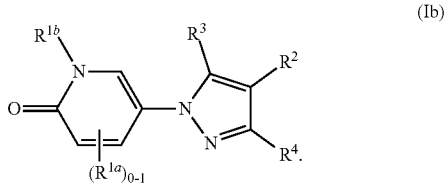

where
R$^{1a}$, when present, is halo, alkyl, alkenyl, haloalkyl, cycloalkyl, cycloalkylalkyl, heterocycloalkyl, or heterocycloalkylalkyl;
R$^{1b}$ is hydrogen, alkyl, alkenyl, haloalkyl, cycloalkyl, cycloalkylalkyl, heterocycloalkyl, or heterocycloalkylalkyl;
R$^2$ is

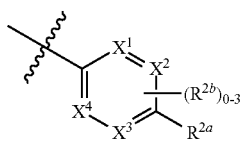

where 0, 1, or 2 of X$^1$-X$^4$ are nitrogen and the remaining are CH or CR$^{2b}$;
R$^{2a}$ is —OR$^5$, —S(O)R$^6$, or —S(O)$_2$R$^7$;
each R$^{2b}$, when present, is independently halo, alkyl, haloalkyl, —NO$_2$, or cyano;
R$^3$ is hydrogen, halo, alkyl, or haloalkyl;
R$^4$ is hydrogen, halo, alkyl, or haloalkyl; and
R$^5$, R$^6$, and R$^7$ are independently alkyl; haloalkyl; hydroxyalkyl; haloalkyl further substituted with 1 or 2 hydroxy; cycloalkyl; cycloalkylalkyl; heterocycloalkyl; or heterocycloalkylalkyl, where the cycloalkyl, alone or as part of cycloalkylalkyl, and heterocycloalkyl, alone or as part of heterocycloalkylalkyl, are optionally substituted with 1, 2, or 3 groups independently selected from alkyl, hydroxy, halo, and hydroxyalkyl; or
a stereoisomer, a mixture of stereoisomers, and/or a pharmaceutically acceptable salt thereof.

2. The Compound of claim 1, where R$^3$ and R$^4$ are hydrogen.

3. The Compound of claim 1 where R$^2$ is

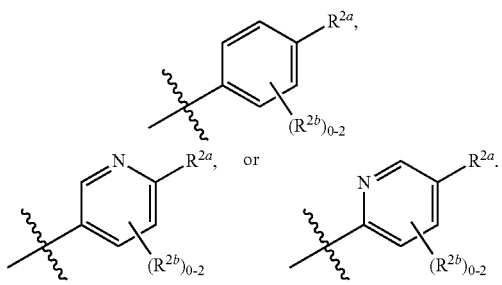

4. The Compound of claim 3 where the R$^2$ ring is substituted with a first R$^{2b}$.

5. The Compound of claim 4 where the first R$^{2b}$ is halo or alkyl.

6. The Compound of claim 4 where the R$^2$ ring is substituted with a second R$^{2b}$.

7. The Compound of claim 6 where the second R$^{2b}$ is halo or —CH$_3$.

8. The Compound of claim 1 where R$^5$, R$^6$, and R$^7$ are independently selected from the group consisting of alkyl; haloalkyl; cycloalkyl, where the cycloalkyl is optionally substituted with 1 or 2 groups that are independently hydroxyalkyl; cycloalkylalkyl, where the cycloalkyl is optionally substituted with 1 or 2 groups that are independently hydroxyalkyl; hydroxyalkyl; haloalkyl further substituted with 1 or 2 hydroxy; heterocycloalkyl which is optionally substituted with 1 or 2 groups that are independently halo; and heterocycloalkylalkyl, where the heterocycloalkyl of heterocycloalkylalkyl is optionally substituted with 1 or 2 groups that are independently hydroxyalkyl.

9. The Compound of claim 1 where R$^{2a}$ is selected from the group consisting of —S(O)$_2$R$^7$ and —OR$^5$.

10. The Compound of claim 9 where R$^5$ is cycloalkylalkyl where the cycloalkyl is optionally substituted with 1 or 2 groups independently selected from alkyl, hydroxy, halo, and hydroxyalkyl.

11. The Compound of claim 1 where R$^{1a}$, when present, is alkyl.

12. The Compound of claim 1 where R$^{1b}$ is alkyl, alkenyl, haloalkyl, cycloalkyl, cycloalkylalkyl, heterocycloalkyl, or heterocycloalkylalkyl.

13. The Compound of claim 1 selected from

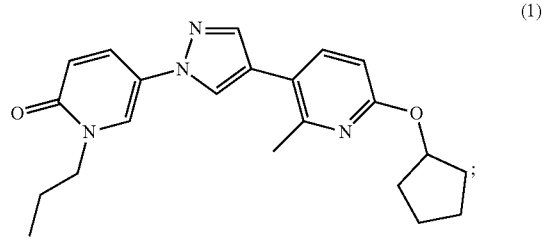

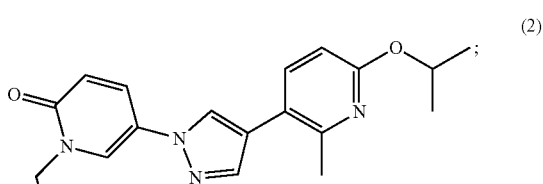

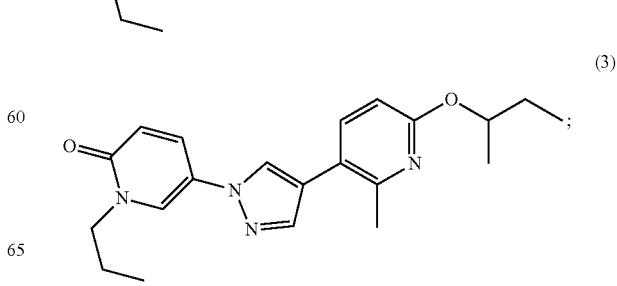

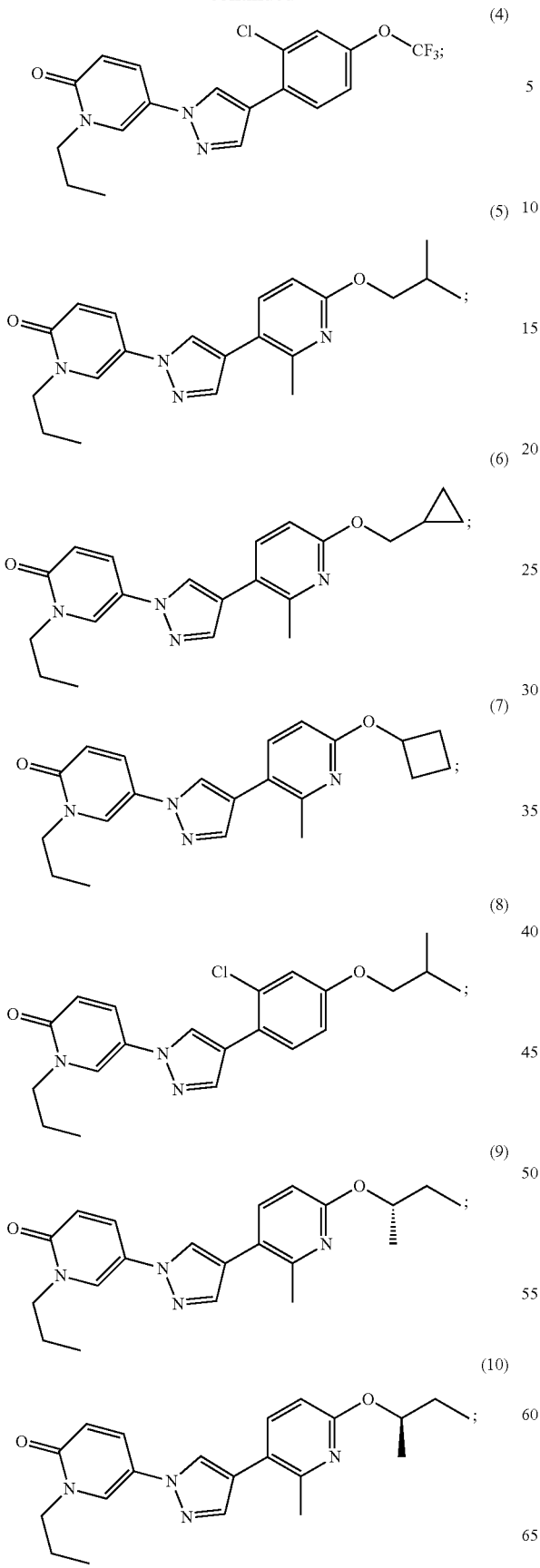
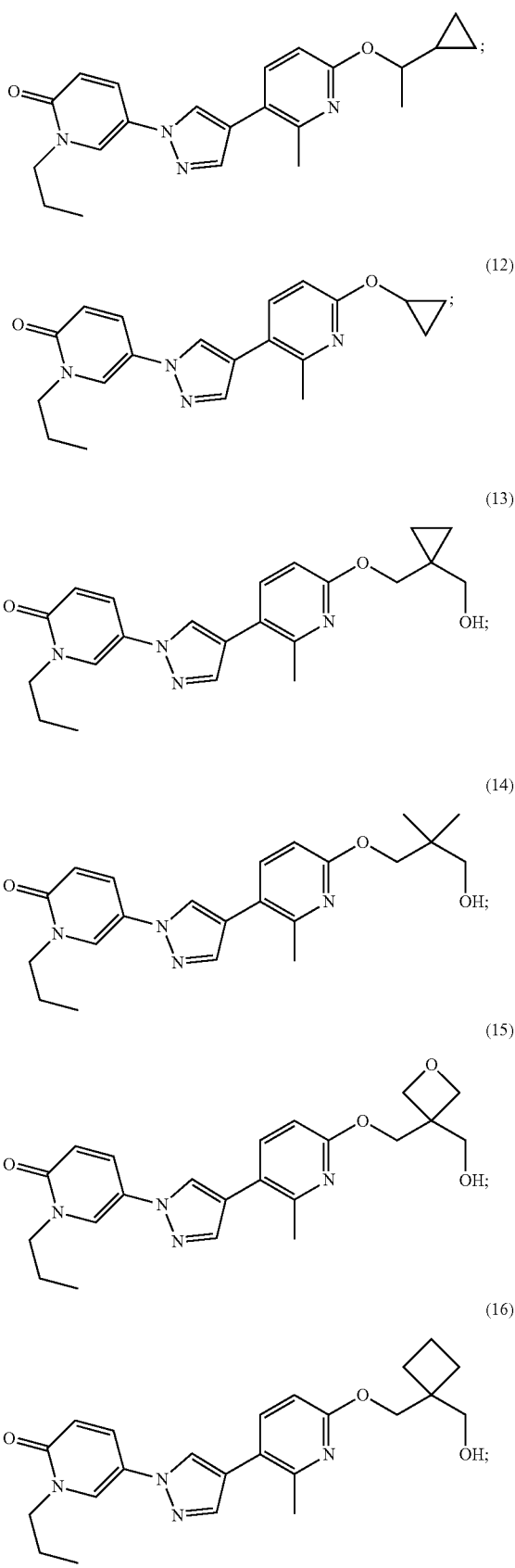

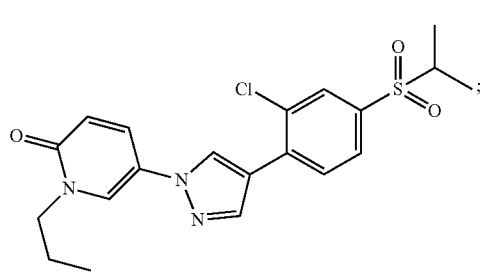
(17)
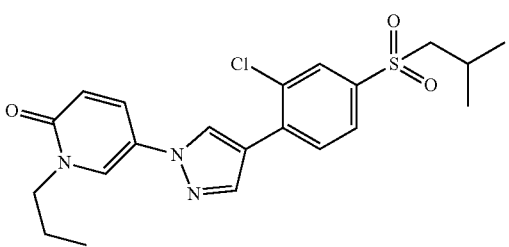
(18)
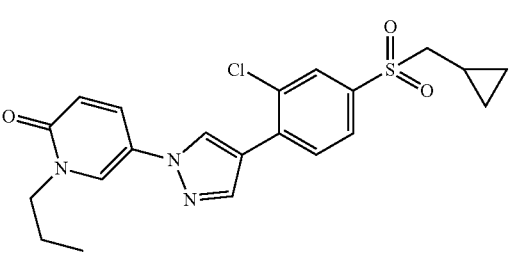
(19)
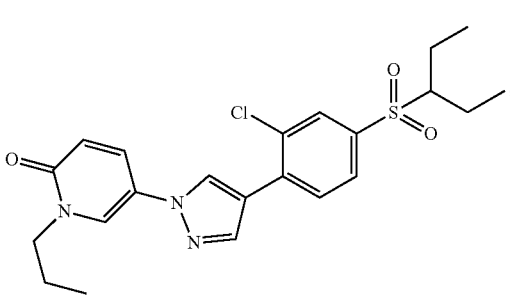
(20)
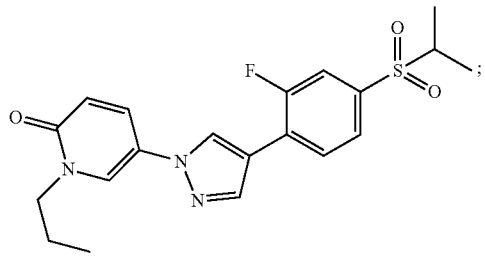
(21)
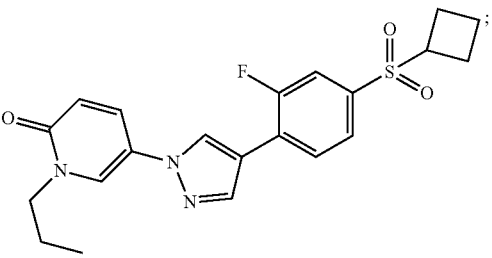
(22)
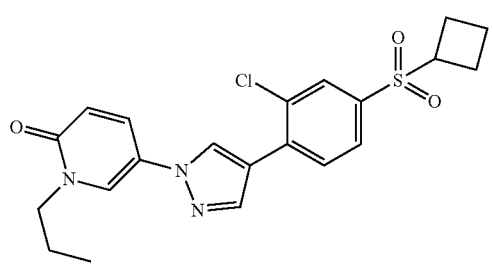
(23)
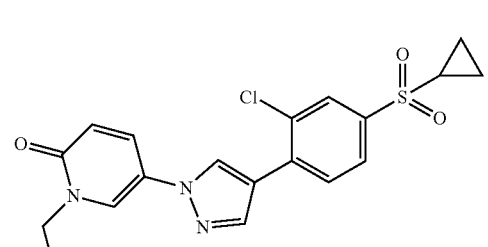
(24)
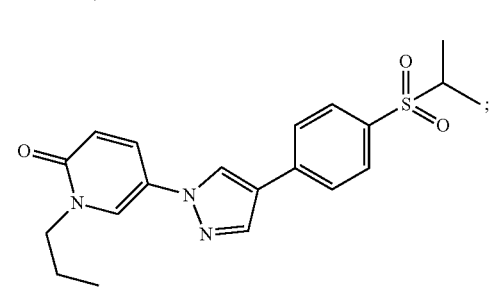
(25)
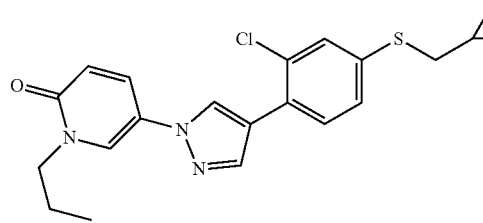
(26)
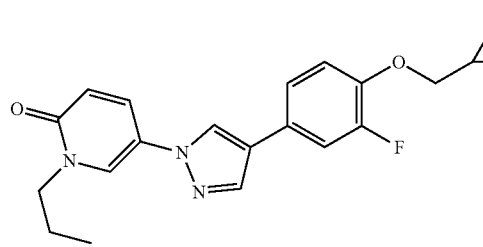
(27)
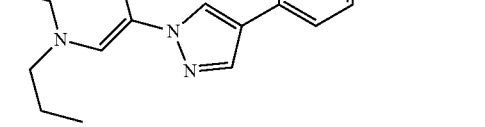
(28)

153
-continued
(29)
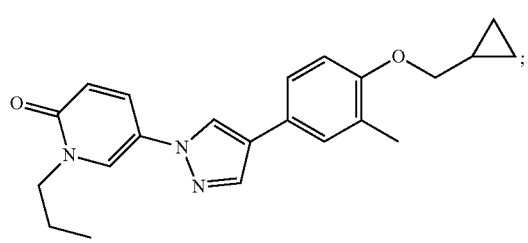
(30)
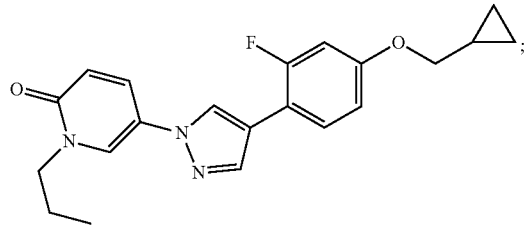
(31)
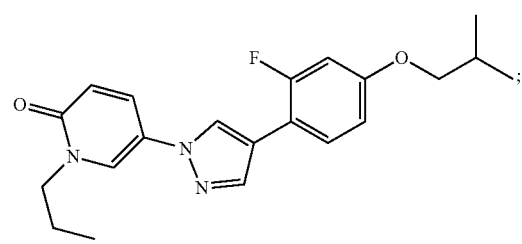
(32)
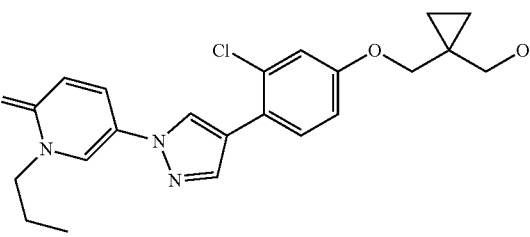
(33)
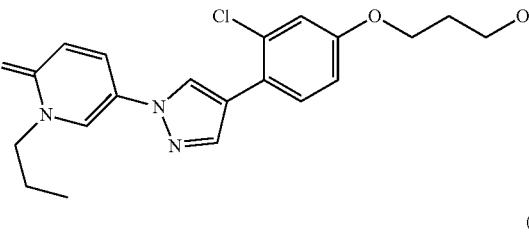
(34)
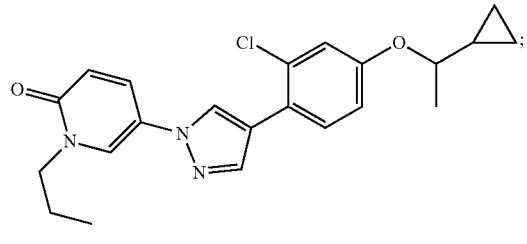
154
-continued
(35)
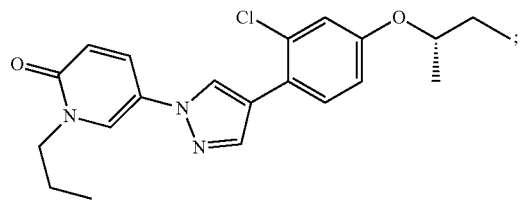
(36)
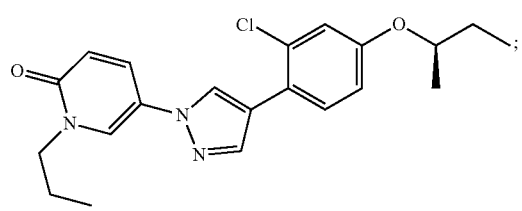
(37)
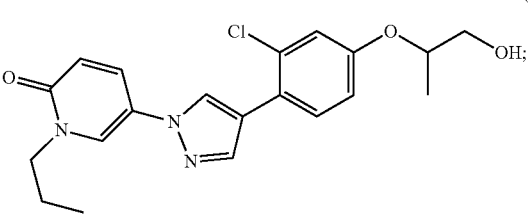
(38)
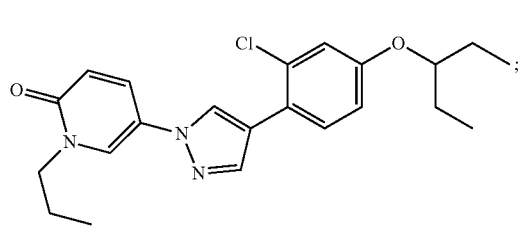
(39)
(40)
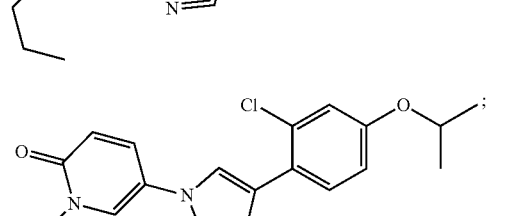
(41)
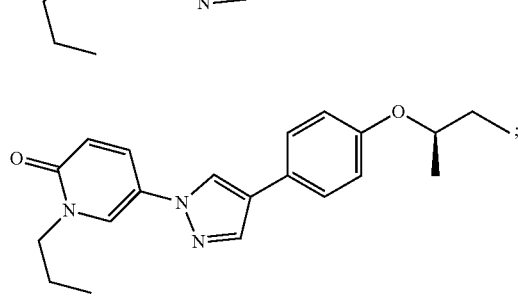

(42) 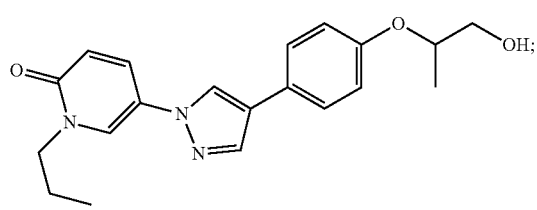
(43) 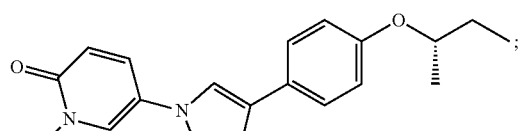
(44) 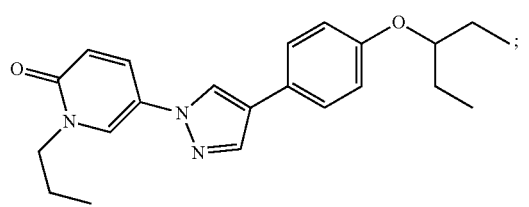
(45) 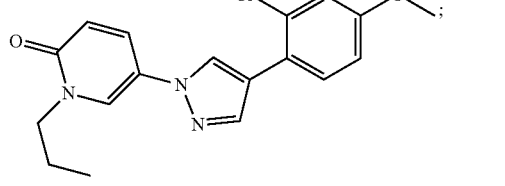
(46) 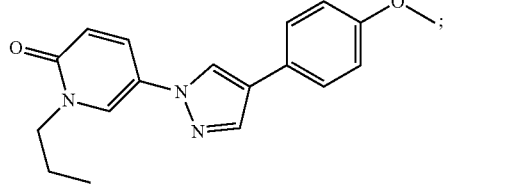
(47) 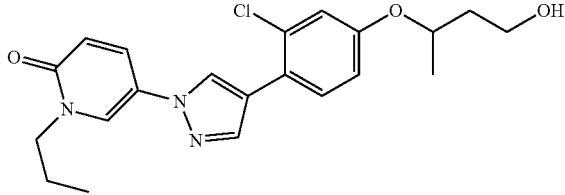
(48) 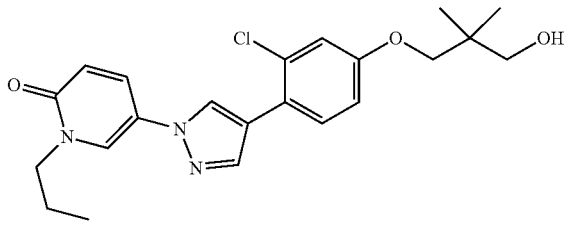
(49) 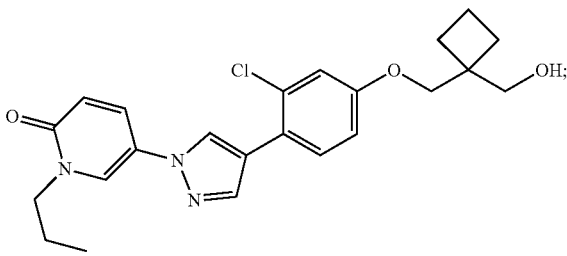
(50) 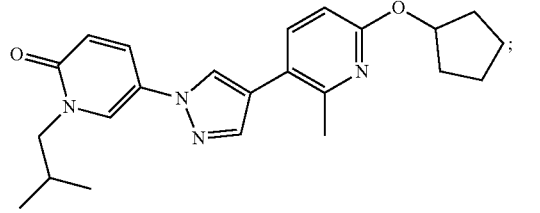
(51) 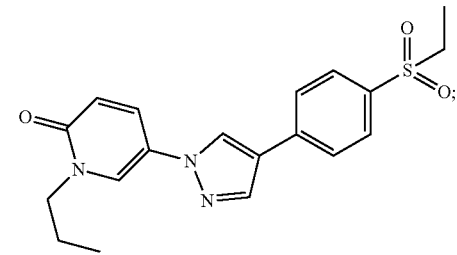
(52) 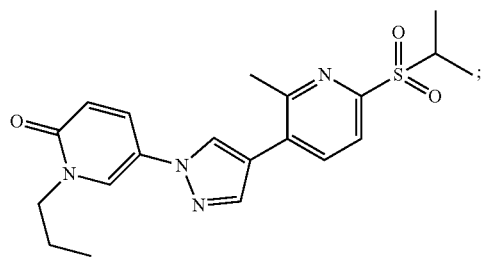
(53) 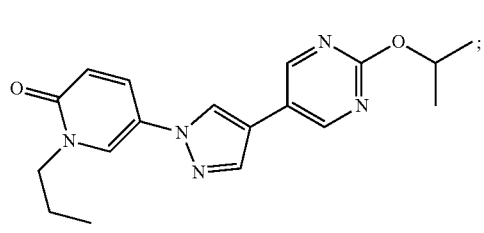
(54) 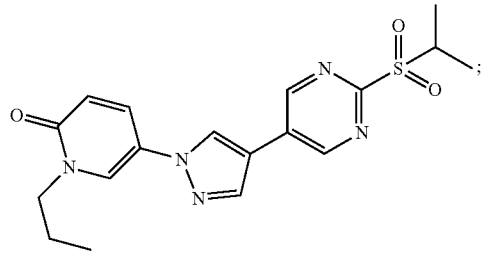

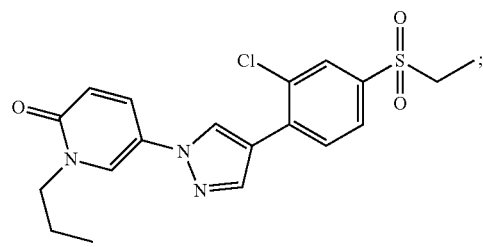
(55)
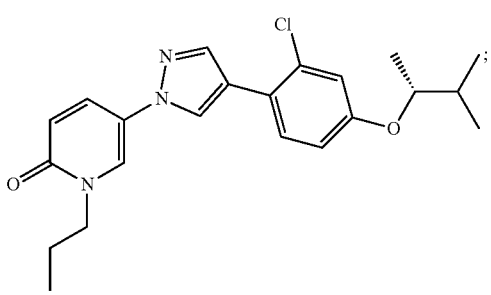
(56)
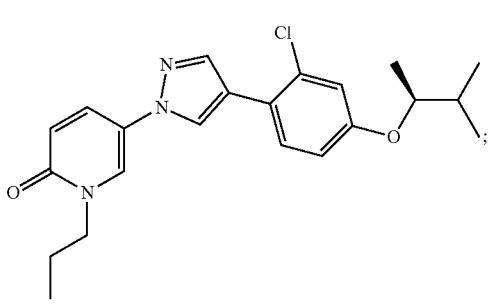
(57)
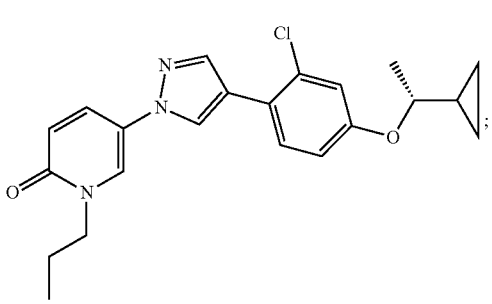
(58)
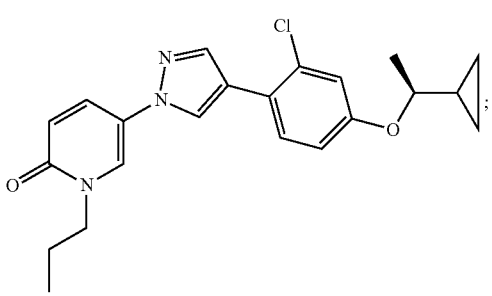
(59)
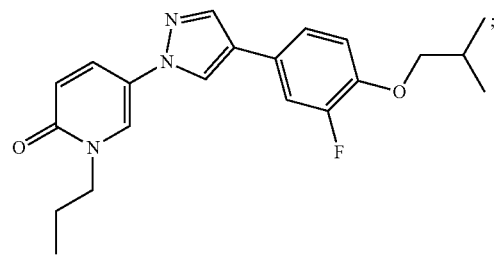
(60)
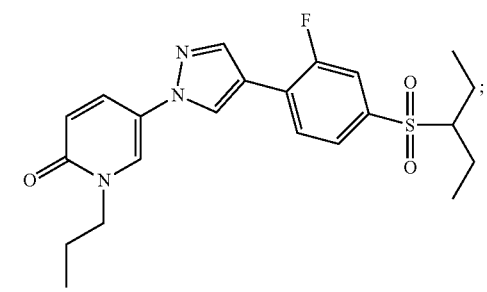
(61)
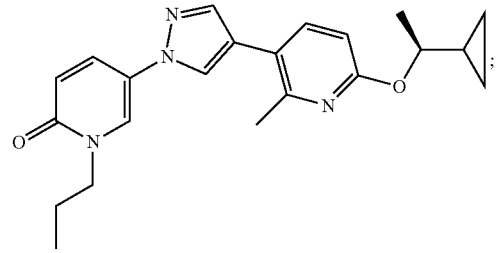
(62)
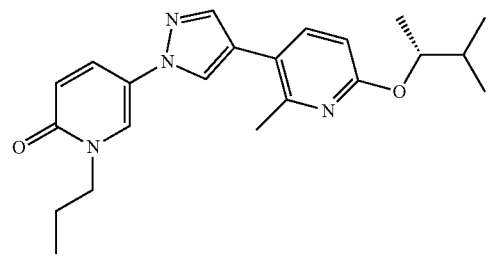
(63)
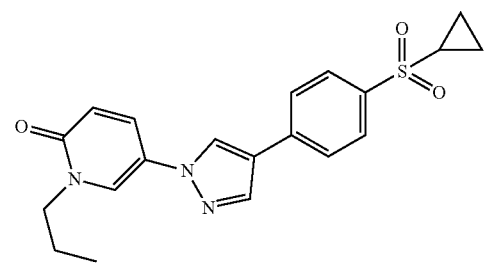
(64)
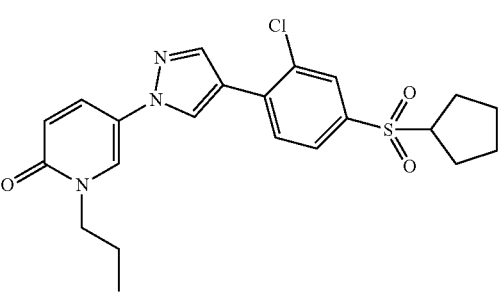
(65)

(66)
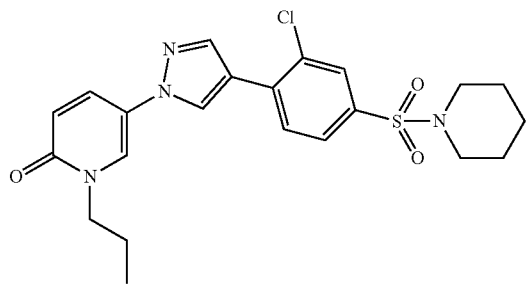
(67)
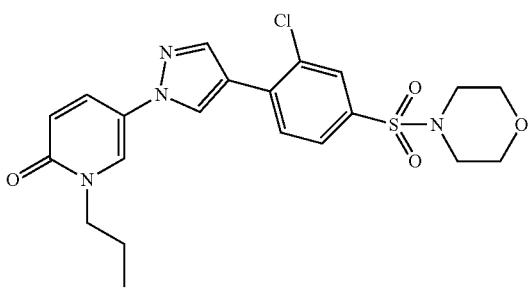
(68)
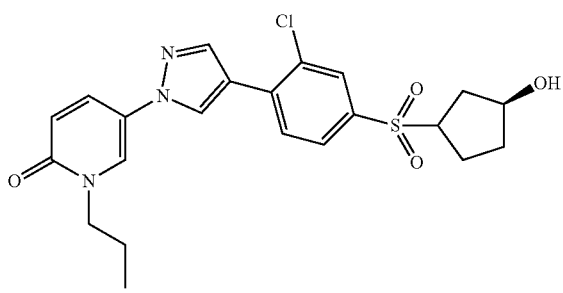
(69)
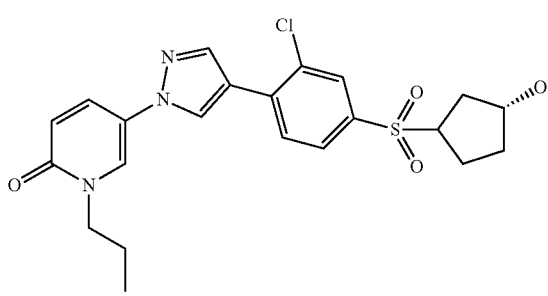
(70)
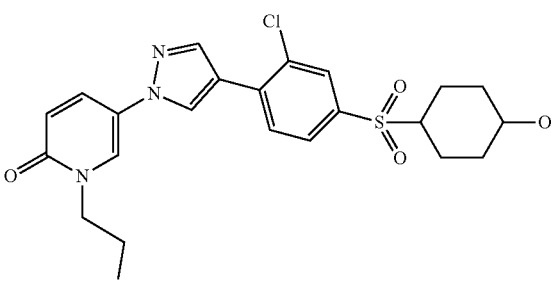
(71)
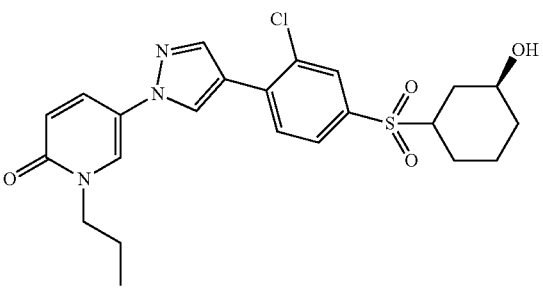
(72)
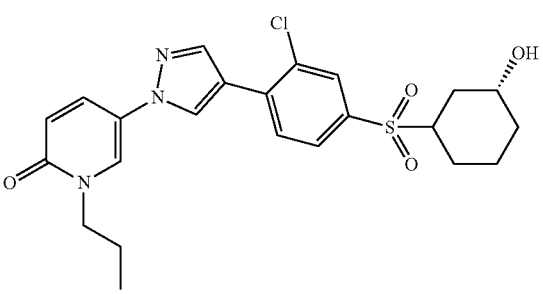
(73)
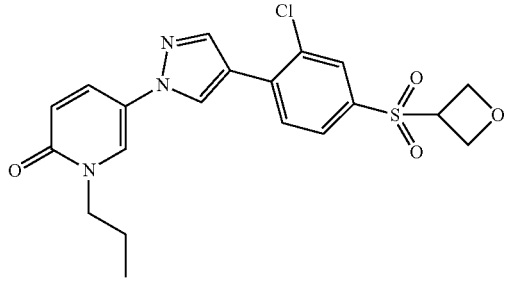
(74)
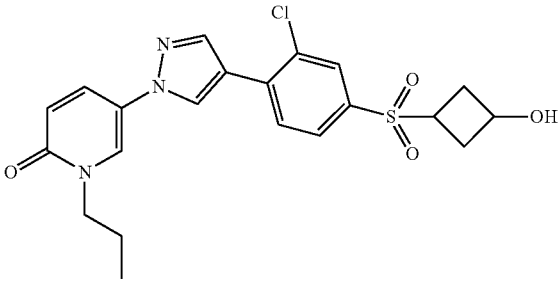
(75)
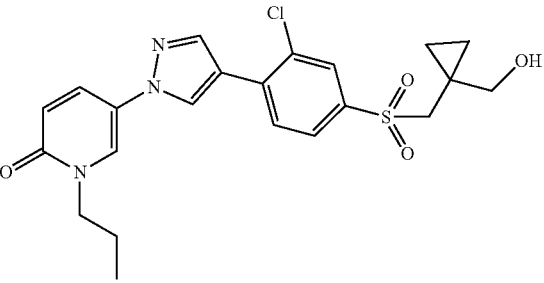

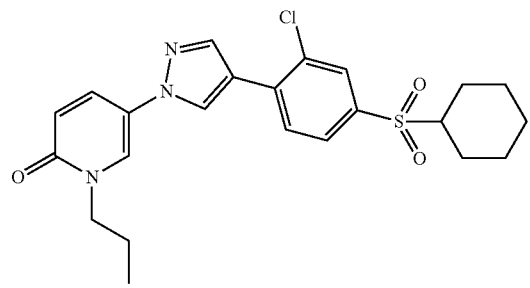
(76)
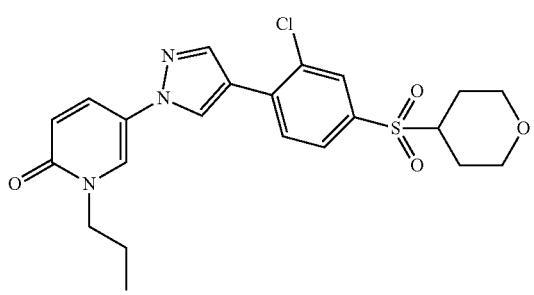
(77)
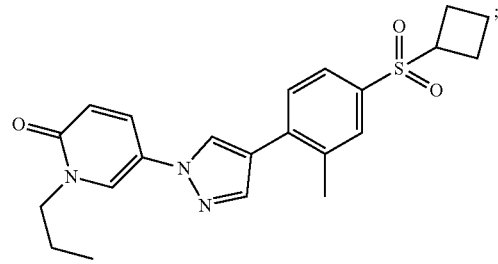
(78)
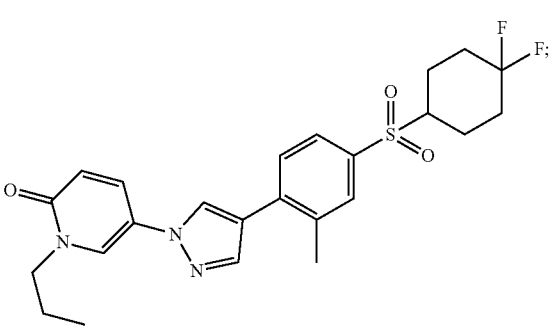
(79)
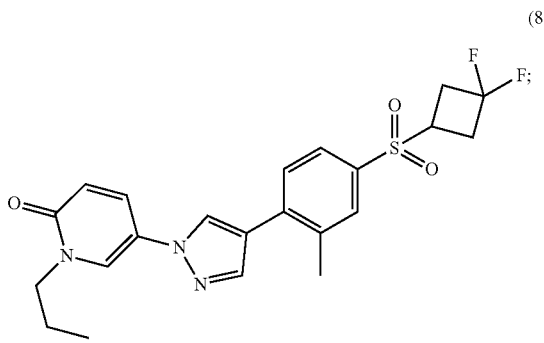
(80)
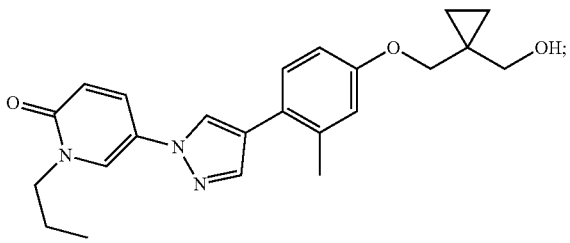
(81)
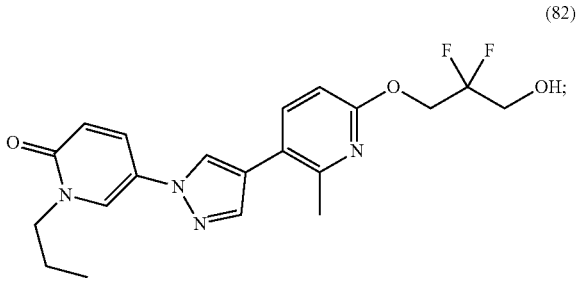
(82)
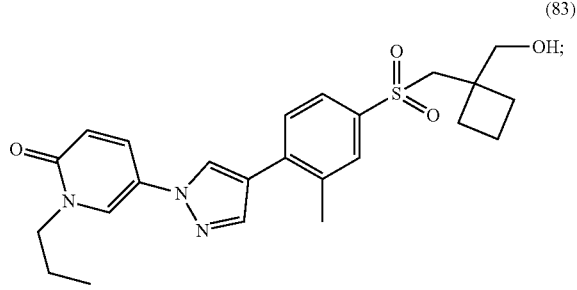
(83)
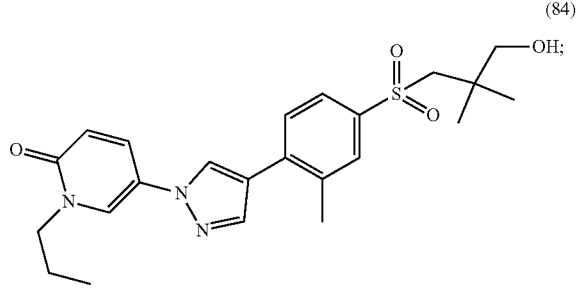
(84)
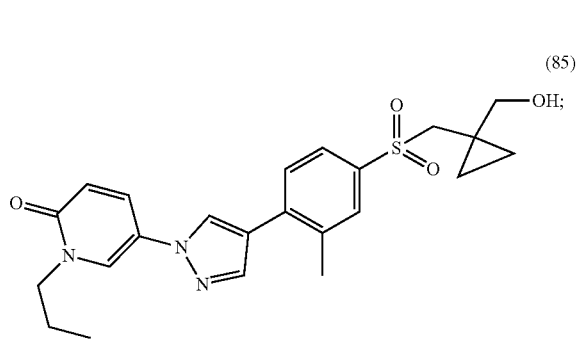
(85)

(86)

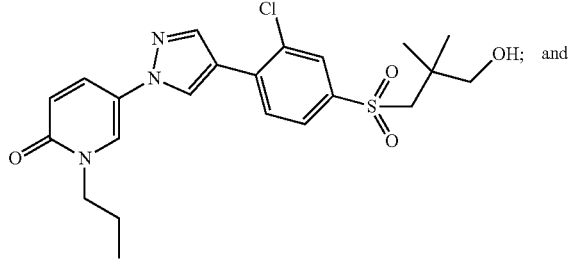

(87)

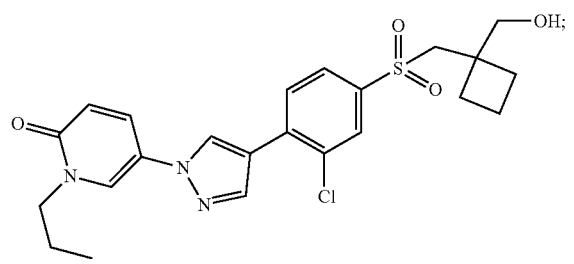

or a stereoisomer, a mixture of stereoisomers, and/or a pharmaceutically acceptable salt thereof.

14. A pharmaceutical composition comprising a Compound of claim 1 or a stereoisomer, a mixture of stereoisomers, and/or a pharmaceutically acceptable salt thereof; and a pharmaceutically acceptable carrier.

15. A method of inhibiting or relieving a condition, disease, or disorder associated with abnormal activation of the SREBP pathway or a method of increasing thermogenesis or reducing body weight in a patient in need thereof, comprising administering to a patient in need thereof an effective amount of the Compound of claim 1 or a stereoisomer, a mixture of stereoisomers, and/or a pharmaceutically acceptable salt thereof; wherein the condition, disease, or disorder is selected from metabolic syndrome, type 2 diabetes, dyslipidemia, obesity, a cell proliferative disease, hyperlipidemia, a lipoprotein related disease, Frederickson Type IIb, familial combined hyperlipidemia, Frederickson Type IV, hyperlipoproteinemia Type V, mixed hyperlipidemia, acquired hyperlipidemia, fatty liver disease, a non-alcoholic steatohepatitis, neutral lipid storage disease, Chanarin-Dorfman Syndrome, diabetic nephropathy, cancer, hepatocellular carcinoma, glioblastoma multiforme, prostate cancer, post-menopausal breast carcinoma, pancreatic adenocarcinoma, ovarian cancer, B-cell lymphoma, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach cancer, gastric cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer.

16. The method of claim 15 where the condition, disease, or disorder is selected from metabolic syndrome, type 2 diabetes, dyslipidemia, obesity, hepatocellular carcinoma, glioblastoma multiforme, prostate cancer, post-menopausal breast carcinoma, pancreatic adenocarcinoma, ovarian cancer, B cell lymphoma, lung cancer, digestive and gastrointestinal cancer, gastrointestinal stromal tumor, gastrointestinal carcinoid tumor, colon cancer, rectal cancer, anal cancer, bile duct cancer, small intestine cancer, stomach cancer, gastric cancer, esophageal cancer, gall bladder cancer, appendix cancer, renal cancer, cancer of the central nervous system, skin cancer, a lymphoma, choriocarcinoma, head and neck cancer, osteogenic sarcoma, and a blood cancer; or wherein the method is for reducing body weight.

17. The method of claim 15, wherein the compound or a stereoisomer, a mixture of stereoisomers, and/or a pharmaceutically acceptable salt thereof is administered in a pharmaceutical composition which additionally comprises a pharmaceutically acceptable carrier.

18. The Compound of claim 1, where $R^{2a}$ is $-OR^5$.

19. The Compound of claim 9 where $R^5$ is cycloalkylalkyl where the cycloalkyl is optionally substituted with 1 or 2 groups independently selected from alkyl, hydroxy, halo, and hydroxyalkyl.

\* \* \* \* \*